US011555698B2

(12) United States Patent
Milligan et al.

(10) Patent No.: US 11,555,698 B2
(45) Date of Patent: Jan. 17, 2023

(54) SYSTEMS AND METHODS FOR ESTIMATING CONCRETE THICKNESS

(71) Applicant: FDH INFRASTRUCTURE SERVICES, LLC, Raleigh, NC (US)

(72) Inventors: David Milligan, Raleigh, NC (US); Armita Mohammadian, Raleigh, NC (US); Joshua Scott, Raleigh, NC (US); Akash Nikam, Raleigh, NC (US); Matthew Sharpe, Raleigh, NC (US); Klarissa Ramos, Raleigh, NC (US); Ethan Loewenthal, Durham, NC (US)

(73) Assignee: FDH Infrastructure Services, LLC, Raleigh, NC (US)

( * ) Notice: Subject to any disclaimer, the term of this patent is extended or adjusted under 35 U.S.C. 154(b) by 0 days.

(21) Appl. No.: 17/737,645

(22) Filed: May 5, 2022

(65) Prior Publication Data

US 2022/0333919 A1 Oct. 20, 2022

Related U.S. Application Data

(62) Division of application No. 17/605,434, filed as application No. PCT/US2021/024223 on Mar. 25, 2021, now Pat. No. 11,326,876.

(Continued)

(51) Int. Cl.
*G01N 29/07* (2006.01)
*G01N 29/44* (2006.01)
(Continued)

(52) U.S. Cl.
CPC ............ *G01B 17/02* (2013.01); *G01N 29/07* (2013.01); *G01N 29/44* (2013.01); *G01N 33/38* (2013.01);
(Continued)

(58) Field of Classification Search
CPC ........ G01B 17/02; G01N 29/44; G01N 29/07; G01N 33/38; G01N 2291/0232; G01N 2291/02854; G01N 2291/011
(Continued)

(56) References Cited

U.S. PATENT DOCUMENTS

| 4,429,575 | A | | 2/1984 | Akishika |
| 5,996,413 | A | * | 12/1999 | Iyer ..................... G01N 29/045 |
| | | | | 73/598 |

(Continued)

FOREIGN PATENT DOCUMENTS

| JP | H0886775 A | 4/1996 |
| KR | 101012441 B1 | 2/2011 |
| KR | 1020200022342 | 3/2020 |

OTHER PUBLICATIONS

International Search Report and Written Opinion corresponding to International Patent Application No. PCT/US2021/024223, dated Aug. 17, 2021.

(Continued)

*Primary Examiner* — Jacques M Saint Surin
(74) *Attorney, Agent, or Firm* — McAndrews Held & Malloy, Ltd.

(57) ABSTRACT

The present disclosure provides systems and methods for non-destructively estimating the thickness of buried concrete without excavation. An example method may include placing one or more first accelerometers at a plurality of vertical positions below the surface of the ground at an approximate first distance from a vertical edge of the buried concrete each time. The method may further include, for each position in the plurality of vertical positions, generating a dispersive wave in the buried concrete and determining a time of arrival of the dispersive wave at the one or more first accelerometers. The method may further include estimating (Continued)

the thickness of the buried concrete based on at least the times of arrival of the dispersive waves at the one or more first accelerometers.

8 Claims, 37 Drawing Sheets

Related U.S. Application Data

(60) Provisional application No. 62/994,607, filed on Mar. 25, 2020.

(51) Int. Cl.
*G01N 33/38* (2006.01)
*G01B 17/02* (2006.01)

(52) U.S. Cl.
CPC .............. *G01N 2291/011* (2013.01); *G01N 2291/0232* (2013.01); *G01N 2291/02854* (2013.01)

(58) Field of Classification Search
USPC ............................................. 73/597
See application file for complete search history.

(56) References Cited

U.S. PATENT DOCUMENTS

| | | | | |
|---|---|---|---|---|
| 6,105,430 | A * | 8/2000 | Kepler | G01N 29/06 73/598 |
| 7,426,879 | B2 * | 9/2008 | Nozaki | G01N 29/46 73/865.8 |
| 10,877,017 | B2 * | 12/2020 | Radjy | G01N 33/383 |
| 11,326,876 | B1 * | 5/2022 | Milligan | G01N 33/38 |
| 2013/0220017 | A1 | 8/2013 | Kim et al. | |
| 2017/0108456 | A1 | 4/2017 | Alizadeh et al. | |

OTHER PUBLICATIONS

Intellectual Property of India, Examination report for Indian Appl No. 202117053164, dated Dec. 5, 2022 (5 pages).

* cited by examiner

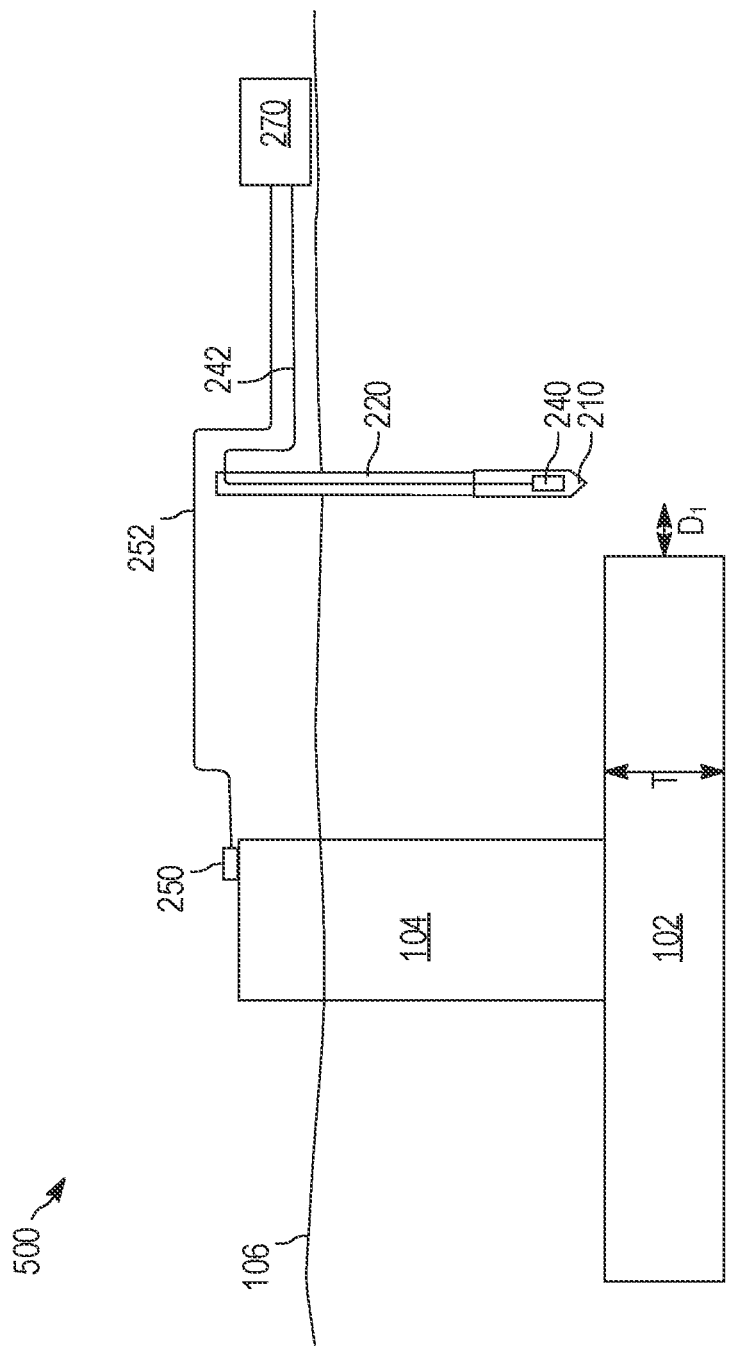

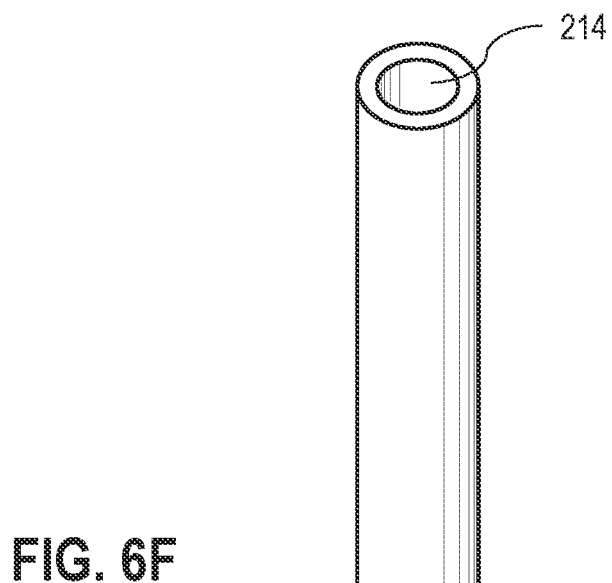
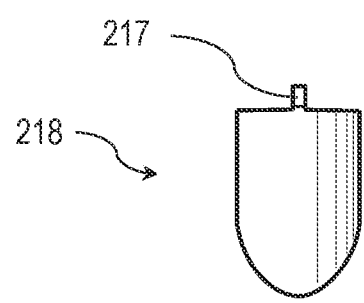
FIG. 6F
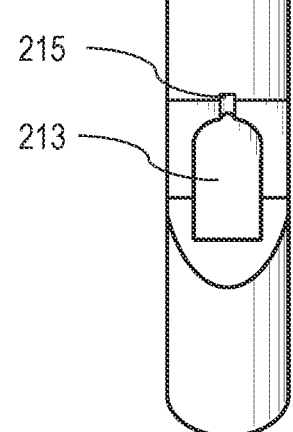
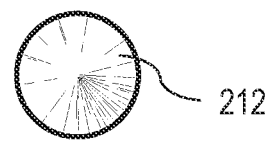
FIG. 6G

SYSTEMS AND METHODS FOR ESTIMATING CONCRETE THICKNESS

CROSS REFERENCE

The present application is a divisional of U.S. patent application Ser. No. 17/605,434, filed Oct. 21, 2021 and titled "Systems and Methods for Estimating Concrete Thickness," which is a U.S. national stage application under § 371 of International Patent Application No. PCT/US2021/024223, filed Mar. 25, 2021, which claims the benefit under 35 U.S.C. § 119(e) of U.S. Provisional Patent Application Ser. No. 62/994,607 filed Mar. 25, 2020 and titled "Systems and Methods for Estimating Concrete Thickness," the disclosures of which are incorporated herein by reference in their entireties and made a part of this specification.

FIELD

The present disclosure generally relates to systems and methods for estimating the thickness of below-grade concrete. More particularly, the disclosure is directed to systems and methods for non-destructively estimating the thickness of below-grade concrete using dry parallel seismic testing.

BACKGROUND

Concrete structures often include both above- and below-grade portions. The above-grade portion is exposed above the surface of the ground (i.e., exposed concrete), while the below-grade portion is buried beneath the surface of the ground (i.e., buried concrete). The exposed concrete is often referred to as a pier or a pedestal, or less commonly, as a column. The buried concrete is often referred to as a pad, a footing, a foundation, or an anchor block. Concrete structures having both above- and below-grade portions are used in many industries for diverse purposes, including to support infrastructures such as cellular telephone towers, transmission line towers, and wind turbines.

In many circumstances, it is desirable to determine or estimate the thickness of the below-grade portion of such concrete structures. This will help to evaluate, for example, whether the concrete structure is suitable for new, updated, or adapted uses as well as any increased load capacity for such uses. Knowing the thickness of below-grade concrete is particularly useful in the telecommunications field because the recently-adopted 5G cellular standard may require different or additional equipment than that required for predecessor technologies. Thus, existing cellular telephone towers may be retrofitted with the different or additional equipment, which could pose different load conditions on the towers.

In some circumstances, the thickness of the below-grade portion of such concrete structures may be unknown. For example, the engineering plans for such structures may be lost, destroyed, or unable to be located. Other times, the structure may not have been built according to design specifications. Uncertainty about the thickness of below-grade concrete is also common in countries that lack rigorous inspection guidelines or regulations.

Current methods for determining or estimating the thickness of below-grade concrete are inefficient. Known methods require excavating around the concrete structure to expose the buried concrete portion, which can lie several feet or more below the surface of the ground. Excavation requires manual labor and/or the use of heavy machinery, both of which are expensive, labor-intensive, time-consuming, and potentially dangerous. Further, excavation is not always practical or possible. When a concrete structure to be investigated is located on a mountain or a hill, it may be difficult or impossible to transport the excavating machinery to the structure. When a concrete structure is located in a rocky area, it may be challenging and expensive to excavate in such areas to expose the concrete.

Another inefficiency in current methods is the risk that while excavating, underground utilities may be inadvertently damaged, causing disruption to nearby residents and business owners. Also, the infrastructure supported by the concrete structures to be excavated, such as cellular telephone towers, often have to be shut down during the excavation, resulting in service disruptions.

A more efficient way of estimating the thickness of below-grade concrete is therefore needed.

SUMMARY

The present disclosure provides systems and methods for non-destructively estimating the thickness of below-grade concrete. The inventive systems and methods disclosed or described herein do not require excavating around a concrete structure, thereby eliminating the inefficiencies and safety hazards of current methods.

These and other features and advantages of the present invention will be apparent from the following detailed description, in conjunction with the appended claims.

DRAWINGS

The foregoing and other objects, features, and advantages of the systems and methods described herein will be apparent from the following description of particular embodiments thereof, as illustrated in the accompanying figures, where like reference numbers refer to like structures. The figures are not necessarily to scale, emphasis instead being placed upon illustrating the principles of the systems and methods described herein.

FIG. 5 is a schematic diagram illustrating an example setup of a system for estimating the thickness of buried concrete.

FIG. 6F is a top perspective view illustrating an example casing and cover.

FIG. 6G is a bottom profile view illustrating an example casing and cover.

FIGS. 20-23, 24A, and 24B are graph diagrams illustrating example plots for estimating the thickness of buried concrete.

Figure 25:
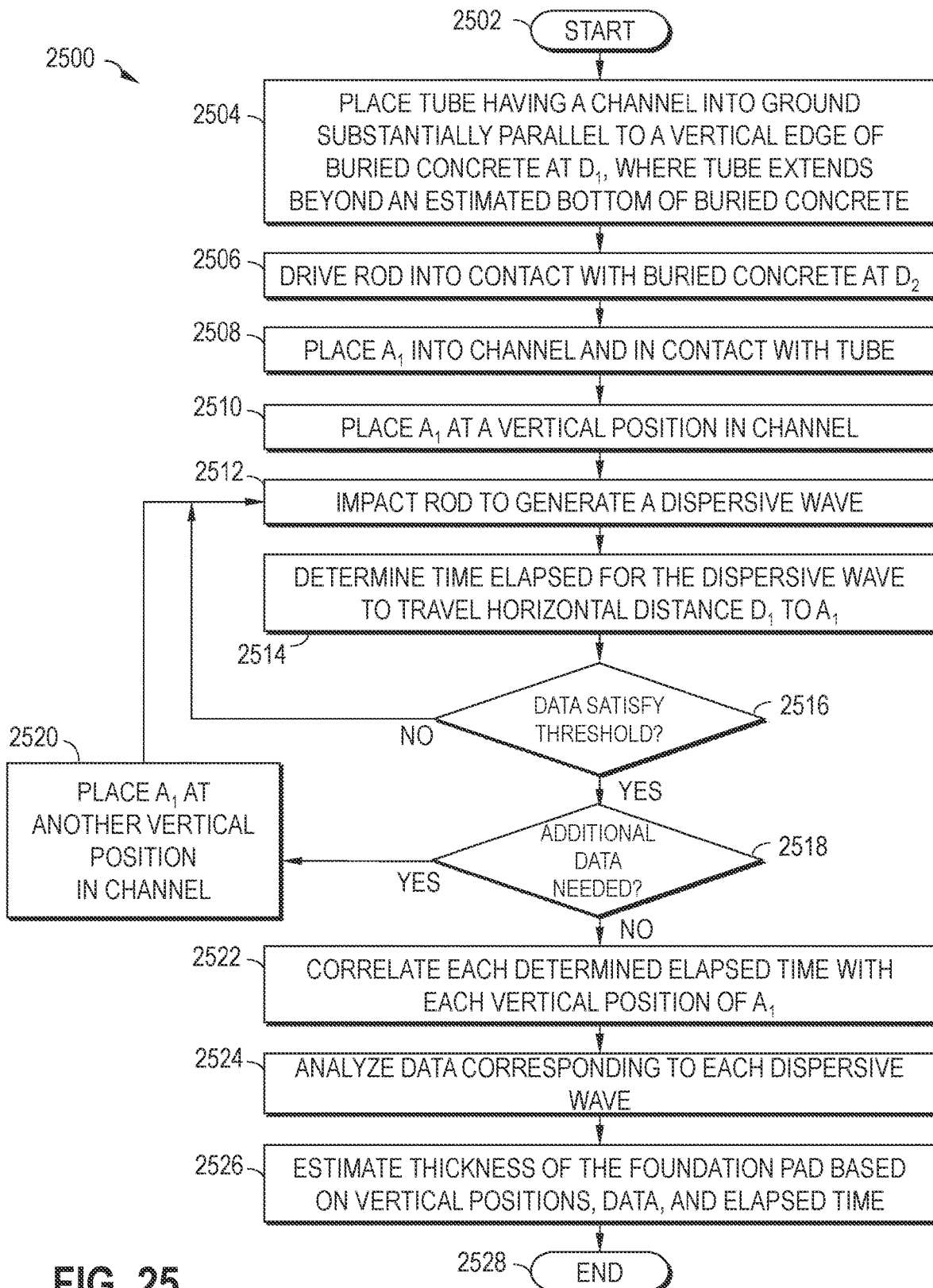
Figure 26:
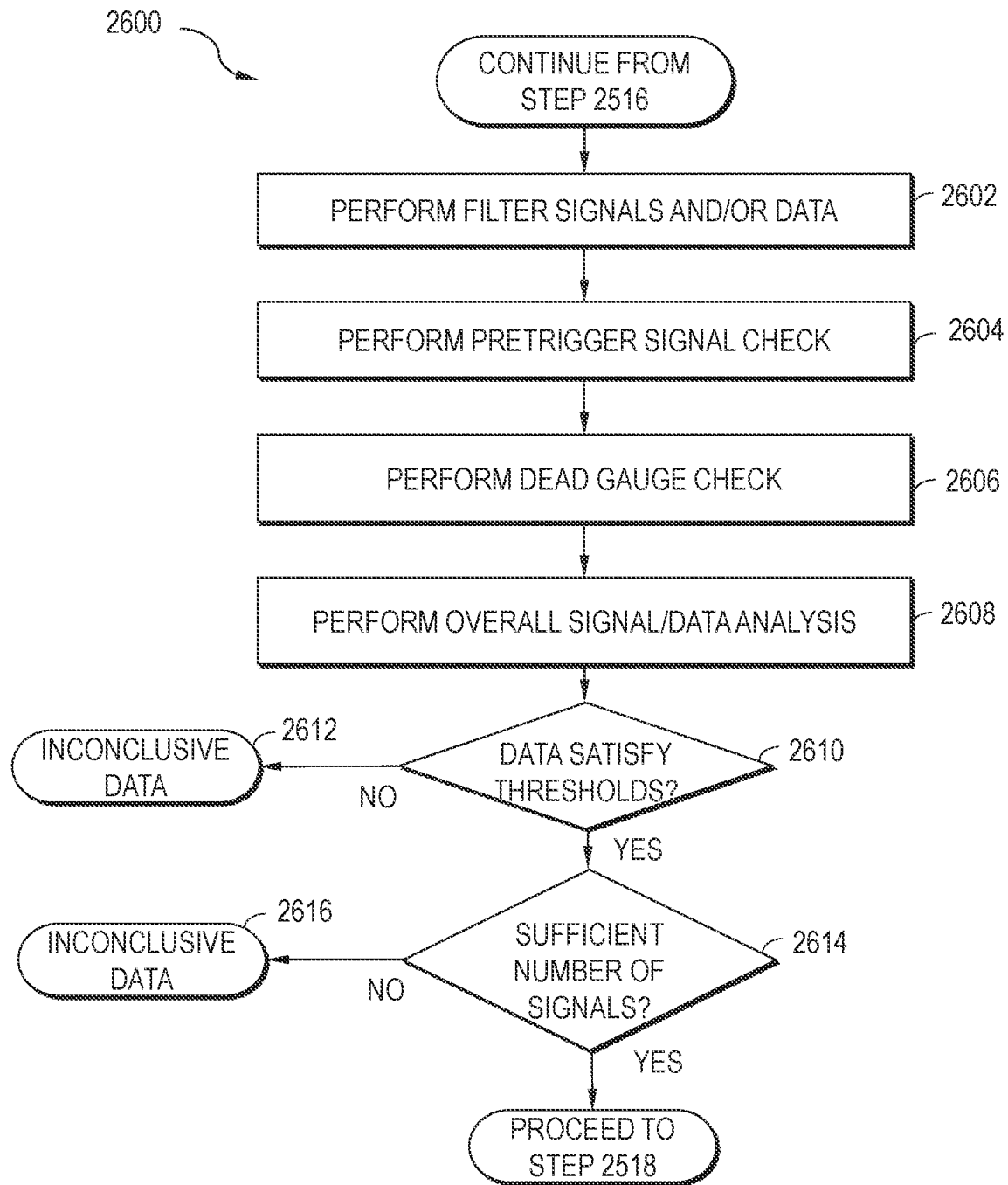
Figure 27:
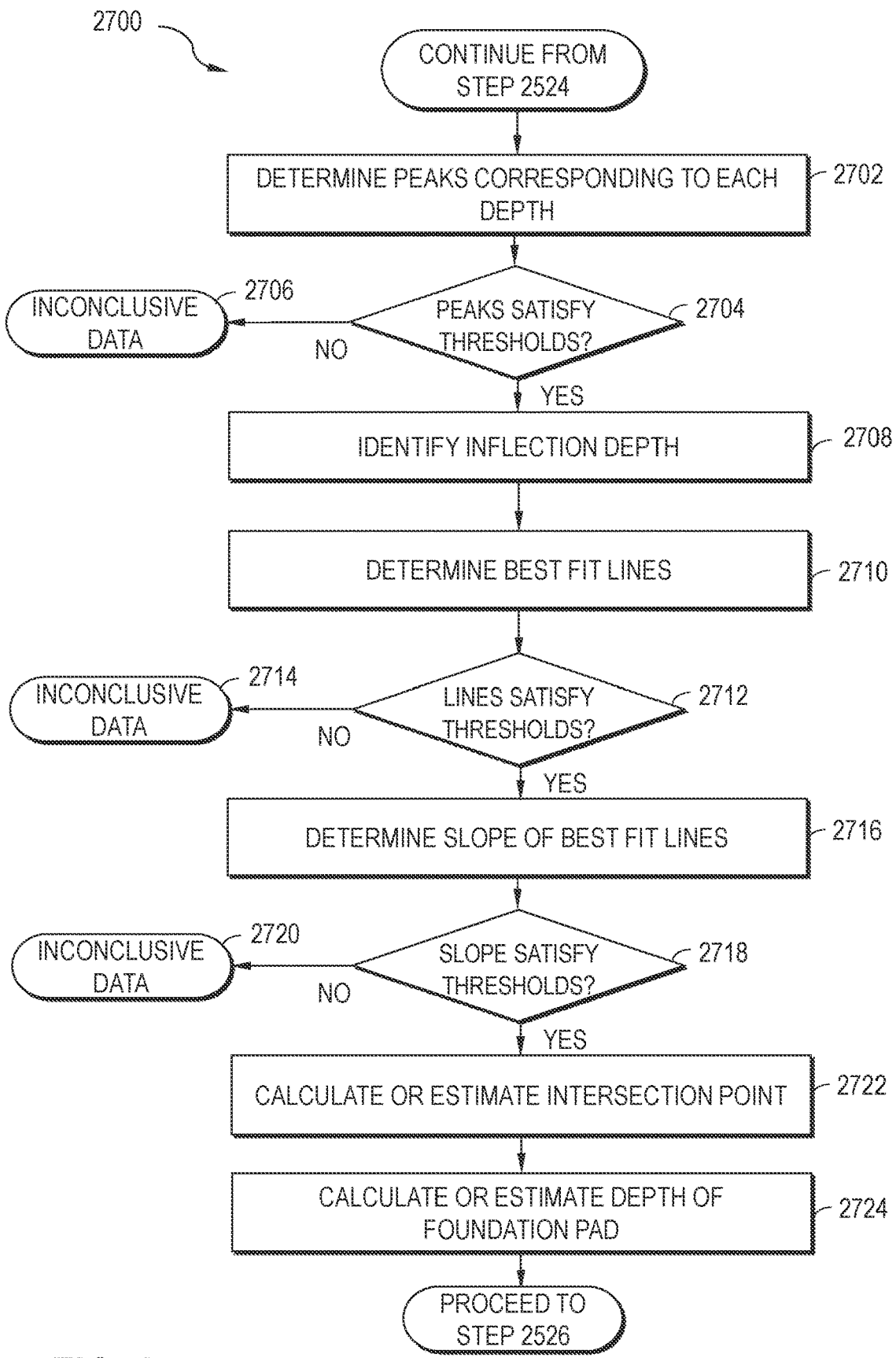

FIGS. 25-27 are flow diagrams illustrating an example method for estimating the thickness of buried concrete.

Figure 28A:
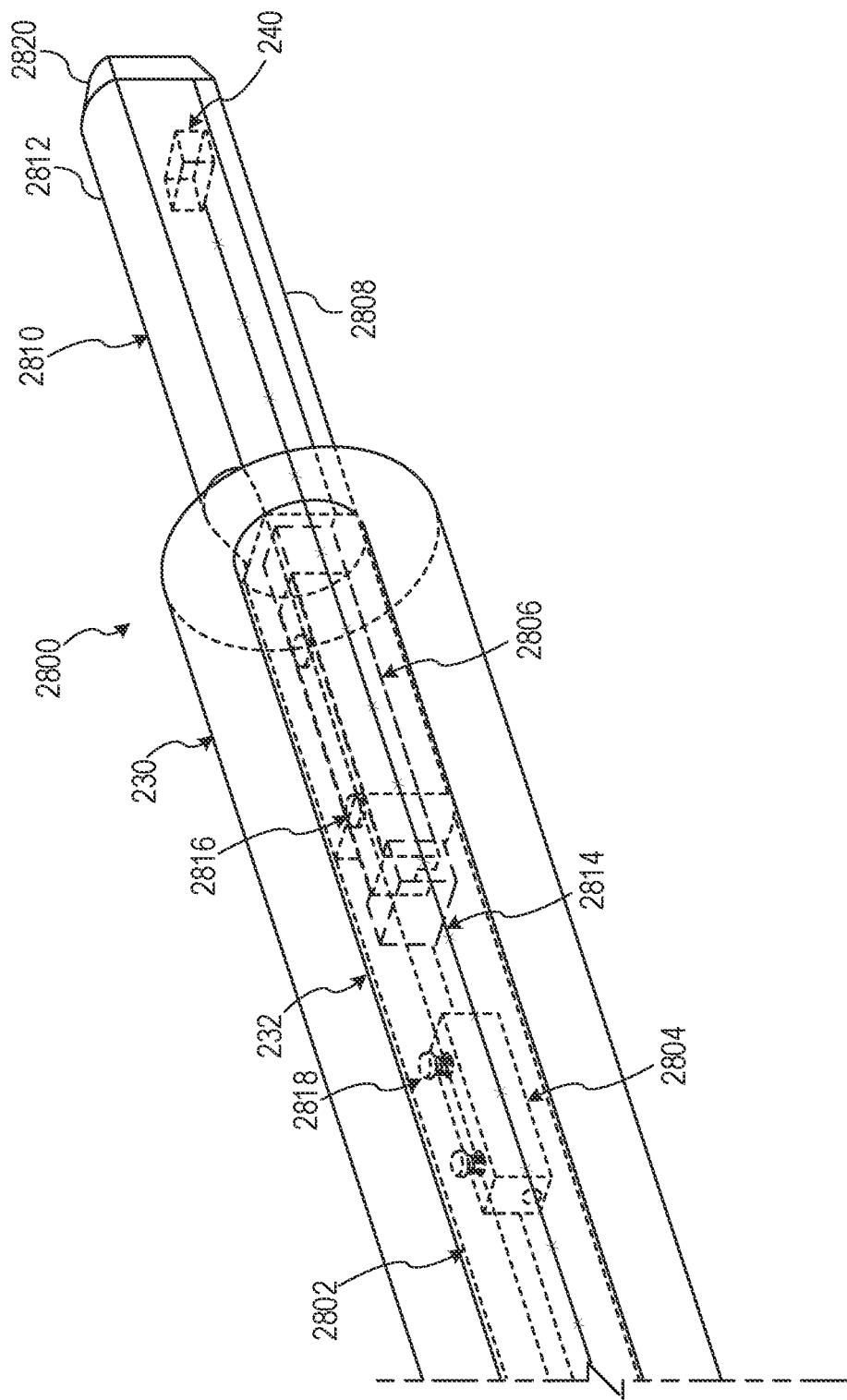
Figure 28B:
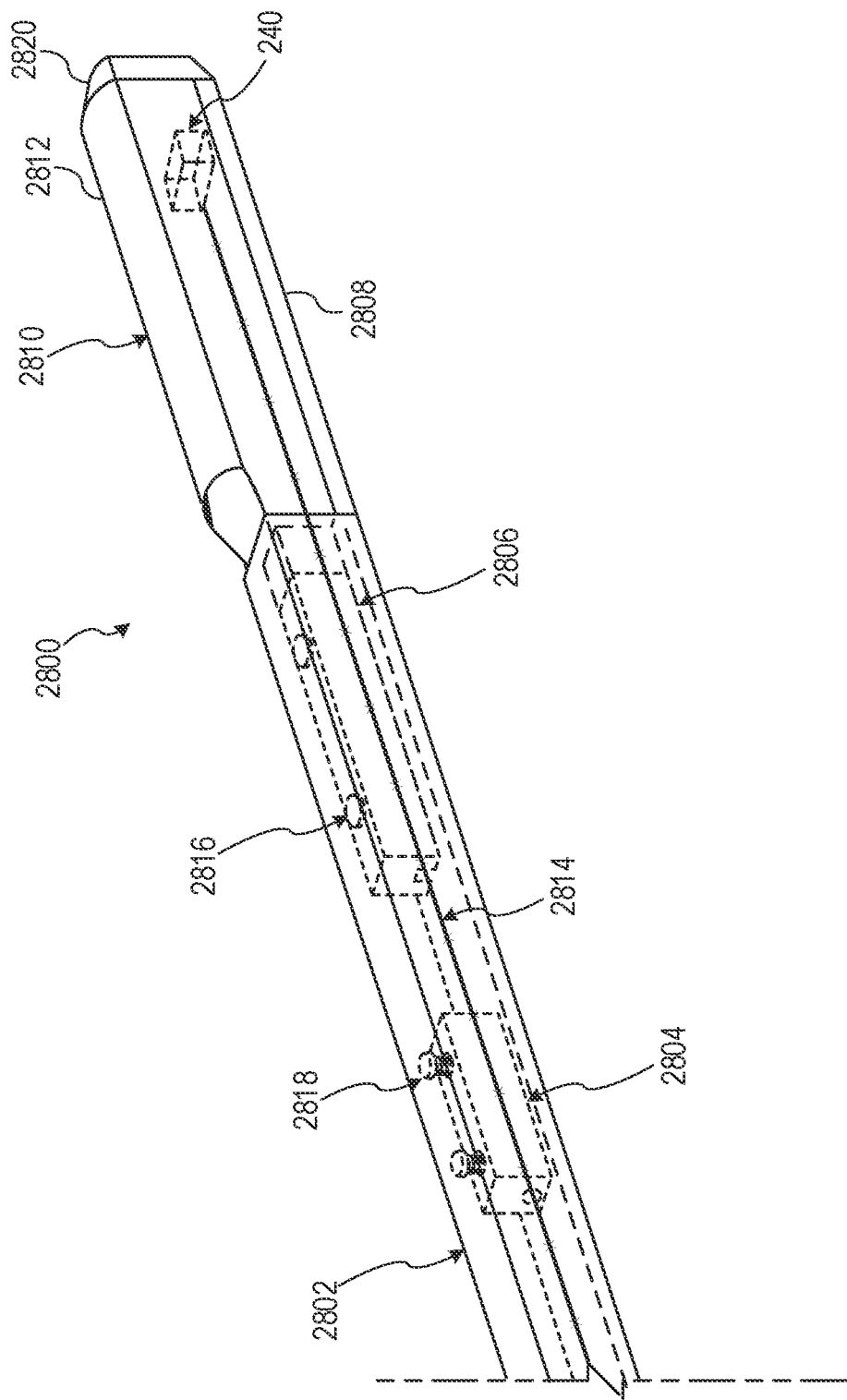

FIGS. 28A and 28B are perspective profile views illustrating an example casing, cover, and conduit.

Figure 29:
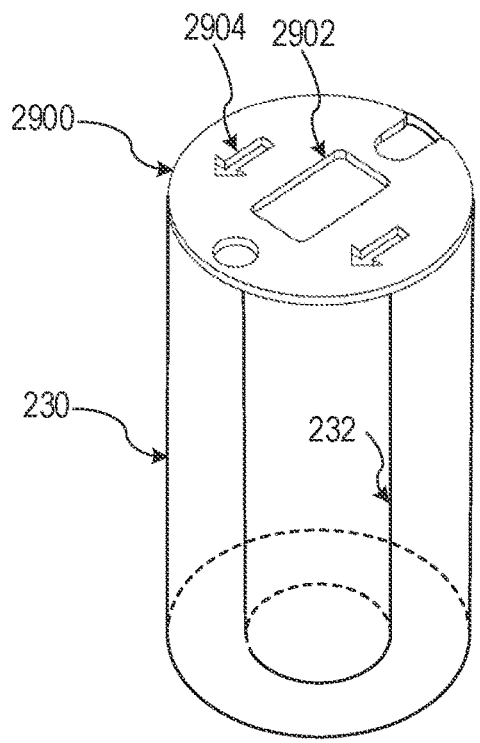

FIG. 29 is a perspective view illustrating an example collar.

Figure 30:
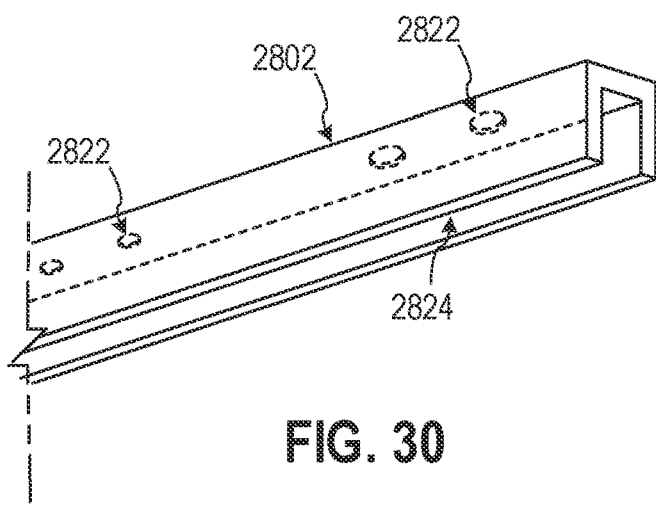

FIG. 30 is a perspective profile view illustrating an example conduit.

Figure 31:
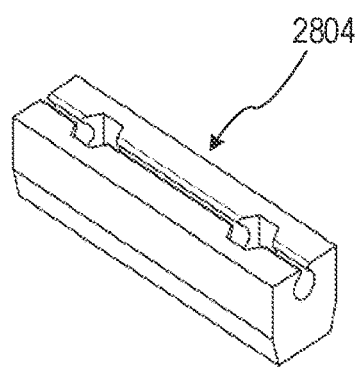

FIG. 31 is a perspective profile view illustrating an example cable tie-down.

Figure 32:
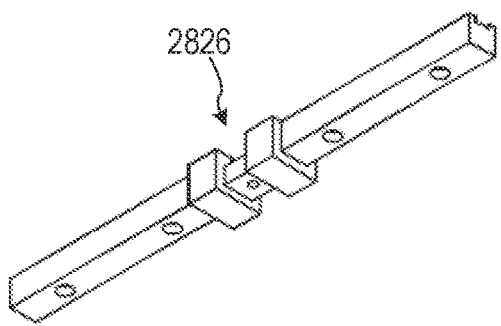

FIG. 32 is a perspective profile view illustrating an example conduit coupler.

DESCRIPTION

References to items in the singular should be understood to include items in the plural, and vice versa, unless explicitly stated otherwise or clear from the text. Grammatical conjunctions are intended to express any and all disjunctive and conjunctive combinations of conjoined clauses, sentences, words, and the like, unless otherwise stated or clear from the context. Recitation of ranges of values herein are not intended to be limiting, referring instead individually to any and all values falling within the range, unless otherwise indicated herein, and each separate value within such a range is incorporated into the specification as if it were individually recited herein. In the following description, it is understood that terms such as "first," "second," "top," "bottom," "side," "front," "back," and the like are words of convenience and are not to be construed as limiting terms unless otherwise stated or clear from context.

As used herein, the terms "about," "approximately," "substantially," or the like, when accompanying a numerical value, are to be construed as indicating a deviation as would be appreciated by one of ordinary skill in the art to operate satisfactorily for an intended purpose. Ranges of values and/or numeric values are provided herein as examples only, and do not constitute a limitation on the scope of the described embodiments. The use of any and all examples, or exemplary language ("e.g.," "such as," or "the like") provided herein, is intended merely to better illuminate the embodiments and does not pose a limitation on the scope of the embodiments. The terms "e.g.," and "for example" set off lists of one or more non-limiting examples, instances, or illustrations. No language in the specification should be construed as indicating any unclaimed element as essential to the practice of the embodiments.

As used herein, the term "and/or" means any one or more of the items in the list joined by "and/or". As an example, "x and/or y" means any element of the three-element set {(x), (y), (x, y)}. In other words, "x and/or y" means "one or both of x and y". As another example, "x, y, and/or z" means any element of the seven-element set {(x), (y), (z), (x, y), (x, z), (y, z), (x, y, z)}. In other words, "x, y, and/or z" means "one or more of x, y, and z."

As used herein, the terms "exemplary" and "example" mean "serving as an example, instance or illustration." The embodiments described herein are not limiting, but rather are exemplary only. It should be understood that the described embodiments are not necessarily to be construed as preferred or advantageous over other embodiments. Moreover, the terms "embodiments of the invention," "embodiments," or "invention" do not require that all embodiments of the invention include the discussed feature, advantage or mode of operation.

As used herein, the term "data" is a broad term and is to be given its ordinary and customary meaning to a person of ordinary skill in the art, and refers without limitation to any indicia, signals, marks, symbols, domains, symbol sets, representations, and any other physical form or forms representing information, whether permanent or temporary, whether visible, audible, acoustic, electric, magnetic, electromagnetic, or otherwise manifested. The term "data" is used to represent predetermined information in one physical form, encompassing any and all representations of corresponding information in a different physical form or forms.

As used herein, the terms "memory" and "memory device" are broad terms and are to be given their ordinary and customary meaning to a person of ordinary skill in the art, and refer without limitation to computer hardware or circuitry to store information. Memory or memory device can be any suitable type of computer memory or other electronic storage means including, for example, read-only memory (ROM), random access memory (RAM), dynamic RAM (DRAM), static RAM (SRAM), ferroelectric RAM (FRAM), cache memory, compact disc read-only memory (CDROM), electro-optical memory, magneto-optical memory, masked read-only memory (MROM), programmable read-only memory (PROM), erasable programmable read-only memory (EPROM), electrically-erasable programmable read-only memory (EEPROM), rewritable read-only memory, flash memory, or the like. Memory or memory device can be implemented as an internal storage medium and/or as an external storage medium. For example, memory or memory device can include hard disk drives (HDDs), solid-state drives (SSDs), optical disk drives, plug-in modules, memory cards (e.g., xD, SD, miniSD, microSD, MMC, etc.), flash drives, thumb drives, jump drives, pen drives, USB drives, zip drives, a computer readable medium, or the like.

As used herein, the term "network" is a broad term and is to be given its ordinary and customary meaning to a person of ordinary skill in the art, and refers without limitation to any communication network including, for example, an extranet, intranet, inter-net, the Internet, local area network (LAN), wide area network (WAN), metropolitan area network (MAN), wireless local area network (WLAN), ad hoc network, wireless ad hoc network (WANET), mobile ad hoc network (MANET), or the like.

As used herein, the term "processor" is a broad term and is to be given its ordinary and customary meaning to a person of ordinary skill in the art, and refers without limitation to processing devices, apparatuses, programs, circuits, components, systems, and subsystems, whether implemented in hardware, tangibly embodied software, or both, and whether or not it is programmable. The term "processor" includes, but is not limited to, one or more computing devices, hardwired circuits, signal-modifying devices and systems, devices and machines for controlling systems, central processing units, microprocessors, microcontrollers, programmable devices and systems, field-programmable gate arrays (FPGA), application-specific integrated circuits (ASIC), systems on a chip (SoC), systems comprising discrete elements and/or circuits, state machines, virtual machines, data processors, processing facilities, digital signal processing (DSP) processors, and combinations of any of the foregoing. A processor can be coupled to, or integrated with, memory or a memory device.

In one aspect, a method of estimating the thickness of buried concrete includes placing one or more first accelerometers at a plurality of vertical positions below the surface of the ground at an approximate first distance from a vertical edge of the buried concrete. The method further includes, for each position in the plurality of vertical positions, generating a dispersive wave in the buried concrete and determining a time of arrival of the dispersive wave at the one or more first accelerometers. The method further includes estimating the thickness of the buried concrete based on at least the times of arrival of the dispersive waves at the one or more first accelerometers.

In another aspect, the step of placing one or more first accelerometers at a plurality of vertical positions below the surface of the ground at a first distance from a vertical edge of the buried concrete can include determining a depth of the top of the buried concrete relative to the surface of the ground. The step can further include placing a substantially-cylindrical tube having a channel into the ground substantially parallel to the vertical edge of the buried concrete. The tube can be placed such that it extends beyond an estimated bottom of the buried concrete. The step can further include placing the one or more first accelerometers into the channel and in contact with the tube. The step can further include moving the one or more first accelerometers to incremental positions within the channel. The incremental positions can include at least a position between the top and the bottom of the buried concrete and a position below the bottom of the buried concrete.

In another aspect, the step of placing the one or more first accelerometers into the channel and in contact with the tube can include placing the one or more first accelerometers into a casing dimensioned to slidably engage the channel and placing the casing into the channel.

In another aspect, the step of generating a dispersive wave in the buried concrete can include placing a rod into contact with the buried concrete at a second distance from the vertical edge of the buried concrete. The step can further include exciting the rod to generate a dispersive wave, which should cause the dispersive wave to be transmitted from the rod to the buried concrete.

In another aspect, the step of determining a time of arrival of the dispersive wave at the one or more first accelerometers can include removably coupling a second accelerometer to the rod and determining the time elapsed for the dispersive wave to travel from the second accelerometer to the one or more first accelerometers.

In another aspect, the step of estimating the thickness of the buried concrete based on at least the times of arrive of the dispersive waves at the one or more first accelerometers can include correlating each time of arrival with each vertical position of the one or more first accelerometers when the time of arrival was determined. The step can further include grouping the times of arrival that are substantially equal and estimating the thickness of the buried concrete based on the vertical positions that correspond to the grouped times of arrival.

In one aspect, a method of estimating the thickness of buried concrete without excavation includes placing a substantially-cylindrical tube having a channel into the ground substantially parallel to, and at a first distance from, a vertical edge of the buried concrete. The tube can be placed such that it extends beyond an estimated bottom of the buried concrete. The method further includes placing a rod into contact with the buried concrete at a second distance from the vertical edge of the buried concrete. The method further includes placing one or more first accelerometers into the channel and in contact with the tube such that the one or more first accelerometers are capable of receiving a dispersive wave transmitted from the tube. The method further includes removably coupling a second accelerometer to the rod. The method further includes placing the one or more first accelerometer at a plurality of vertical positions within the channel. The method further includes, for each position in the plurality of vertical positions, exciting the rod to generate a dispersive wave and determining the time elapsed for the dispersive wave to travel from the second accelerometer to the one or more first accelerometers. The method further includes correlating each time elapsed with each vertical position of the one or more first accelerometers when the elapsed time was determined. The method further includes grouping the elapsed times that are approximately equal and estimating the thickness of the buried concrete based on the vertical positions that correspond to the grouped times.

In another aspect, the step of placing the one or more first accelerometers at a plurality of vertical positions within the channel can include placing the one or more first accelerometers at a first vertical position that is approximately above the top of the buried concrete and incrementally lowering the one or more first accelerometers in the channel to a plurality of positions. The plurality of positions can include a vertical position that is approximately below an estimated bottom of the buried concrete.

In one aspect, a system to determine a thickness of a buried concrete structure includes a computing device configured to receive a first group of motion data from one or more first accelerometers at a first group of vertical positions below a surface of the ground at an approximate first lateral distance from a vertical edge of the buried concrete structure. The computing device is further configured to receive a second group of motion data from one or more first accelerometers at a second group of vertical positions below the surface of the ground at an approximate second lateral distance from the vertical edge of the buried concrete structure. The computing device is further configured to determine a first group of times of arrival at the one or more first accelerometers corresponding to the first group of vertical positions from a first group of dispersive waves emanating from the buried concrete structure. The computing device is further configured to determine a second group of times of arrival at the one or more first accelerometers corresponding to the second group of vertical positions from a second group of dispersive waves emanating from the buried concrete structure. The computing device is further configured to determine an inflection depth from the first and second groups of times of arrival. The computing device is further configured to generate a first best fit line along a first set of data values from the first group of motion data, wherein at least some of the depths corresponding to the first set of data values are above the inflection depth. The computing device is further configured to generate a second best fit line along a second set of data values from the second group of motion data, wherein at least some of the depths corresponding to the second set of data values are below the inflection depth. The computing device is further configured to identify an intersection point between the first and second best fit lines and calculate or estimate a thickness of the buried concrete structure based on the intersection point or the first and second best fit lines.

In another aspect, the one or more first accelerometers generate one or more signals that include the first or second set of data values based on the times of arrival of the first or second groups of dispersive waves and transmit the signals to the computing device. In some aspects, the computing device is further to determine whether a quality of the one or more signals satisfies one or more signal quality thresholds.

In another aspect, the computing device is further configured to determine whether data from the one or more signals satisfies one or more data quality thresholds sufficient to identify an inflection depth.

In another aspect, the computing device is further configured to reject one or more of the first or second sets of data if the signal quality or data fail to satisfy the one or more thresholds.

In one aspect, a system to determine a thickness of a buried concrete structure includes a hollow tube to be driven into the ground adjacent the buried concrete structure. The system further includes a casing to house an accelerometer. The system further includes a conduit configured to extend into the hollow tube and support the casing arranged at a first end of the hollow tube. The system further includes a collar that includes an opening shaped to accept the conduit in one or more distinct orientations, the collar arranged at an opening of the hollow tube at a second end opposite the first end to receive one or more conduits.

In another aspect, the system can further include an accelerometer housed within the casing and configured to generate data associated with a plurality of dispersive waves emanating from the buried concrete structure. The system further can further include a receiver communicatively coupled to the accelerometer. The receiver can include a display, at least one input module to receive data from the accelerometer, a processor, and memory coupled to the processor. In some aspects, the memory stores instructions that, when executed by the processor, cause the processor to receive data from the accelerometer associated with a plurality of dispersive waves and process the received data to determine a thickness of the buried concrete structure.

In another aspect, processing the received data to determine a thickness of the buried concrete structure can include performing one or more quality checks on the received data.

In another aspect, the one or more quality checks can include a pre-trigger noise check on data as it is received from the accelerometer.

In another aspect, the one or more quality checks can include a dead gauge check.

In another aspect, the one or more quality checks can include a pre-trigger noise check on all of the received data.

In another aspect, processing the received data to determine a thickness of the buried concrete structure can include determining an inflection depth.

In another aspect, processing the received data to determine a thickness of the buried concrete structure can further include determining a first best fit line for data above the inflection depth, determining a second best fit line for data below the inflection depth, determining an intersection of the first and second best fit lines, and determining a thickness of the buried concrete structure based on the intersection.

Figure 1:
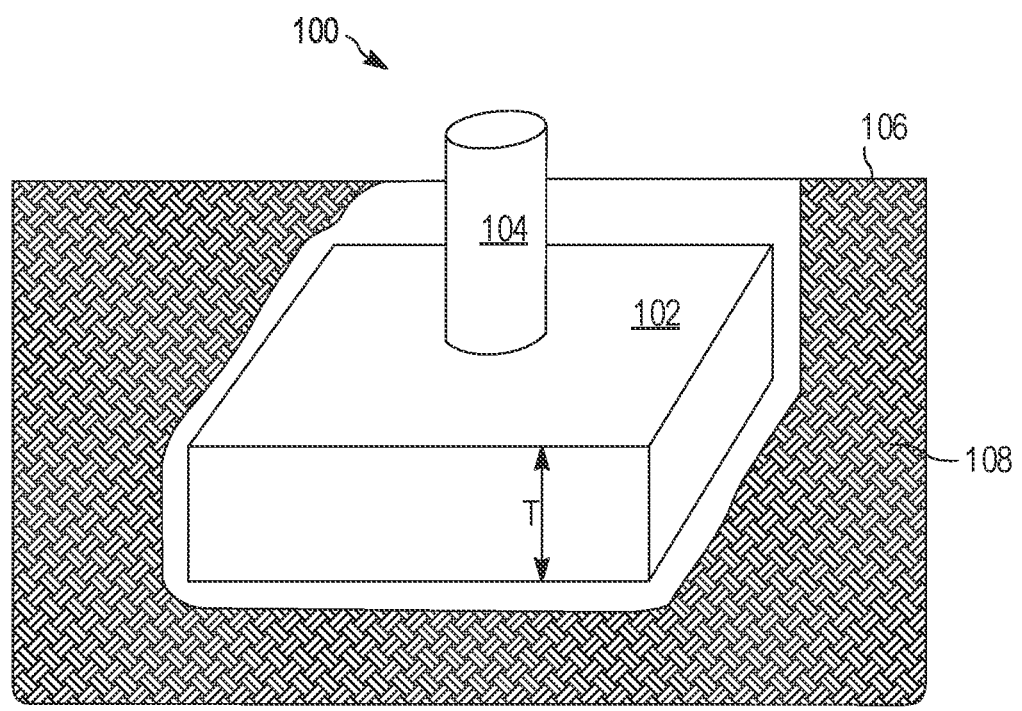
FIG. 1 is a schematic diagram illustrating an example concrete structure.

FIG. 1 is schematic diagram illustrating an example concrete structure 100 to which the inventive systems and methods may be applied. The structure includes a buried concrete portion 102 having a thickness T, and that lies beneath the surface of the ground 106. The structure further includes an exposed concrete portion 104, wherein the top of the exposed concrete portion 104 extends above the surface of the ground 106 and the bottom of the exposed concrete portion 104 is in contact with the buried concrete portion 102. As illustrated, the concrete structure 100 is generally surrounded by Earth 108, which can be any Earth material, including soil, dirt, sand, gravel, clay, rocks, etc. The concrete structure illustrated in FIG. 1 may be used to support a cellular telephone tower, for example. It should be noted, however, that the structure of FIG. 1 is provided for illustrative purposes only. The inventive systems and methods can be applied to any buried concrete and are not limited to the type of structure illustrated in FIG. 1.

Figure 2:
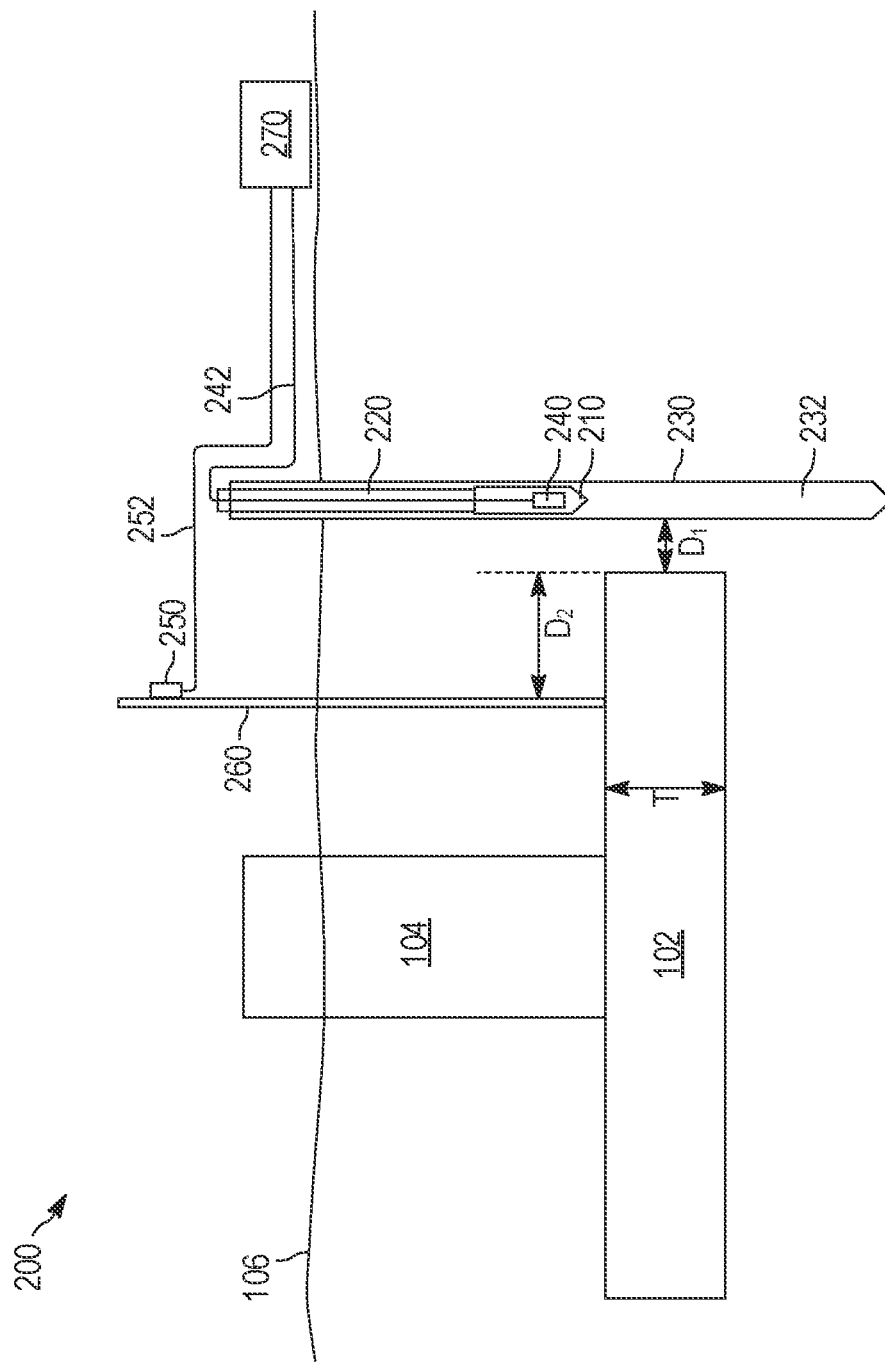
FIG. 2 is a schematic diagram illustrating an example setup of a system for estimating the thickness of buried concrete.

FIG. 2 is a schematic diagram illustrating an example setup of a system 200 for estimating the thickness of buried concrete 102. The system 200 can include a first sensor $S_1$ 240 that can be removably secured in a casing 210, which is explained further below. The system 200 can include a substantially-cylindrical hollow tube 230 having a channel 232 formed by an inner wall of hollow tube 230. Hollow tube 230 is driven into the Earth 108, preferably in a vertical direction, to a depth that is beneath an estimated bottom of the buried concrete 102. Although the depth of the bottom of buried concrete 102 may not be known (as one purpose of the invention is to estimate the thickness of the buried concrete 102), the top of the buried concrete 102 can be determined, for example, by driving a rod through the Earth 108 until it reaches the buried concrete 102 (not shown in FIG. 2). Hollow tube 230 can then be driven a sufficient distance beneath the known distance of the top of buried concrete 102. For example, it may be estimated that the thickness of buried concrete 102 is within the range of one to four feet. Thus, hollow tube 230 can be driven to a depth that is greater than the depth of the surface of buried concrete 102 plus the estimated maximum thickness of buried concrete 102. Preferably, hollow tube 230 is driven to about two feet below the estimated bottom of buried concrete 102.

Hollow tube 230 can be driven parallel to, and at a distance $D_1$ from, a vertical edge of buried concrete 102. Distance $D_1$ can be any distance that permits a dispersive wave to be transmitted from the buried concrete 102 to hollow tube 230. Preferably, distance $D_1$ is within the range of about 6 to 10 inches. Hollow tube 230 can be driven into the Earth 108 using any method familiar to those of ordinary skill in the art. For example, hollow tube 230 can be driven into the Earth 108 by inserting a rod (not shown) into channel 232 and striking the rod to drive hollow tube 230 into the Earth 108. Hollow tube 230 can have a pointed tip as illustrated in FIG. 2 to help facilitate being driven into the Earth 108.

Sensor $S_1$ 240 can be configured to slidably engage hollow tube 230 directly (not shown in FIG. 2) or can be configured to slidably engage hollow tube 230 indirectly, for example, by being encased in casing 210, which can be dimensioned to slidably engage hollow tube 230. For example, hollow tube 230 and casing 210 can be made of plastic, polyvinyl chloride (PVC), metal, or any other suitable material such that casing 210 is capable of sliding within channel 232 to different vertical positions while remaining in contact with hollow tube 230. Casing 210 preferably remains in contact with hollow tube 230 to better enable dispersive waves to be received by sensor $S_1$ 240 as explained further below.

Casing 210 can be positioned at different vertical positions within channel 232 using conduit 220. Conduit 220 can be removably coupled to casing 210, for example, using a male/female interface. Alternatively, conduit 220 can be permanently coupled to casing 210 thereby forming one solid piece. Conduit 220 can have a length generally long enough to extend casing 210 to the bottom of hollow tube 230. Alternatively, and preferably, conduit 220 can comprise sections that can be removably coupled to one another, for example, using male/female interfaces, to extend the length of conduit 220. This may help make it easier to transport conduit 220. Conduit 220 can include a scale having incremental markings that indicate the length of conduit 220. For example, the incremental markings can be spaced one inch apart. The scale can help identify the depth of casing 210.

Figure 6A:
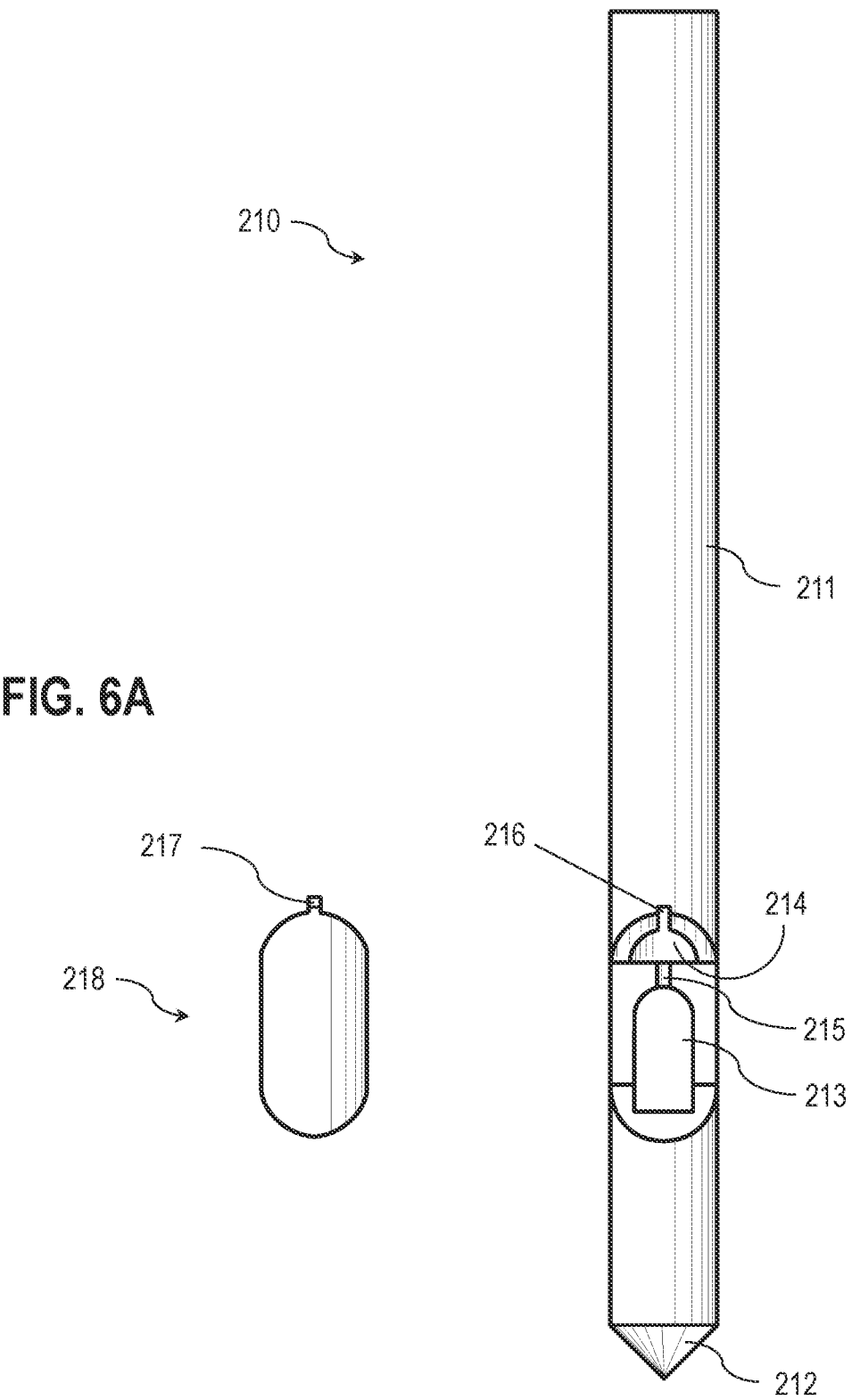
FIG. 6A is a front profile view illustrating an example casing and cover.

FIGS. 6A-6F illustrate different views of an example casing 210 and related cover 218 that can be used, for example, in the system 200. FIG. 6A is a front profile view illustrating casing 210 and cover 218. As illustrated, casing 210 can have a generally cylindrical body 211 and a pointed tip 212. Casing 210 can include a cavity 213 configured to house sensor $S_1$ 240 (not shown). Casing 210 can further include a longitudinal channel 214 to route a transmission line (not shown) from sensor $S_1$ 240 (not shown) through casing 210. Casing 210 can further include a groove 215 to facilitate routing the transmission line from cavity 213 to channel 214. Cover 218 can be used to cover cavity 213 to help protect sensor $S_1$ 240 when casing 210 is in use. Cover 218 can be removably coupled to casing 210, for example, with tab 217, which is configured to engage notch 216 in casing 210. Other means familiar to those of ordinary skill in the art can be used for coupling cover 218 to casing 210.

Figure 6B:
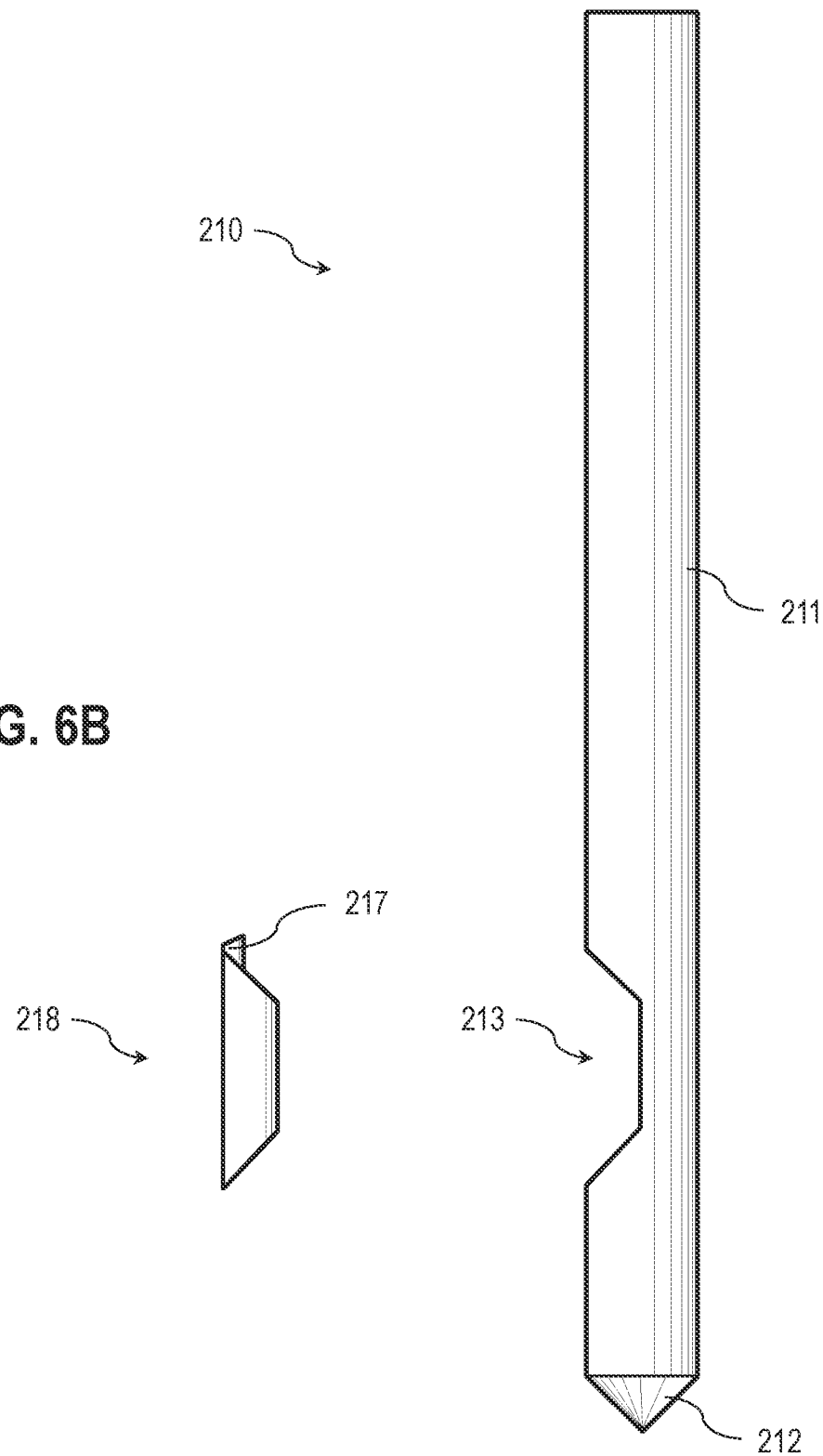
FIG. 6B is a side profile view illustrating an example casing and cover.
Figure 6C:
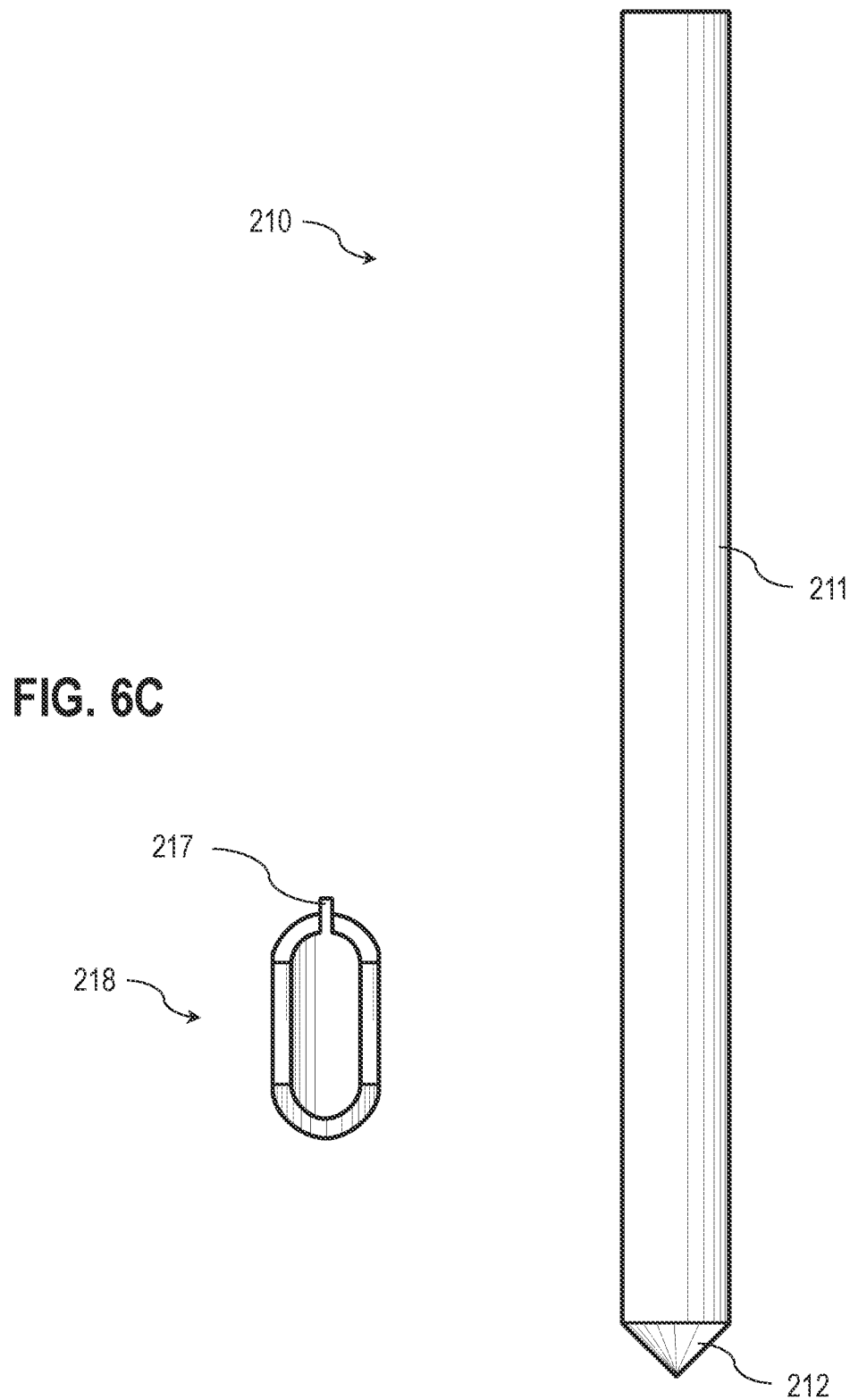
FIG. 6C is a rear profile view illustrating an example casing and cover.
Figure 6D:
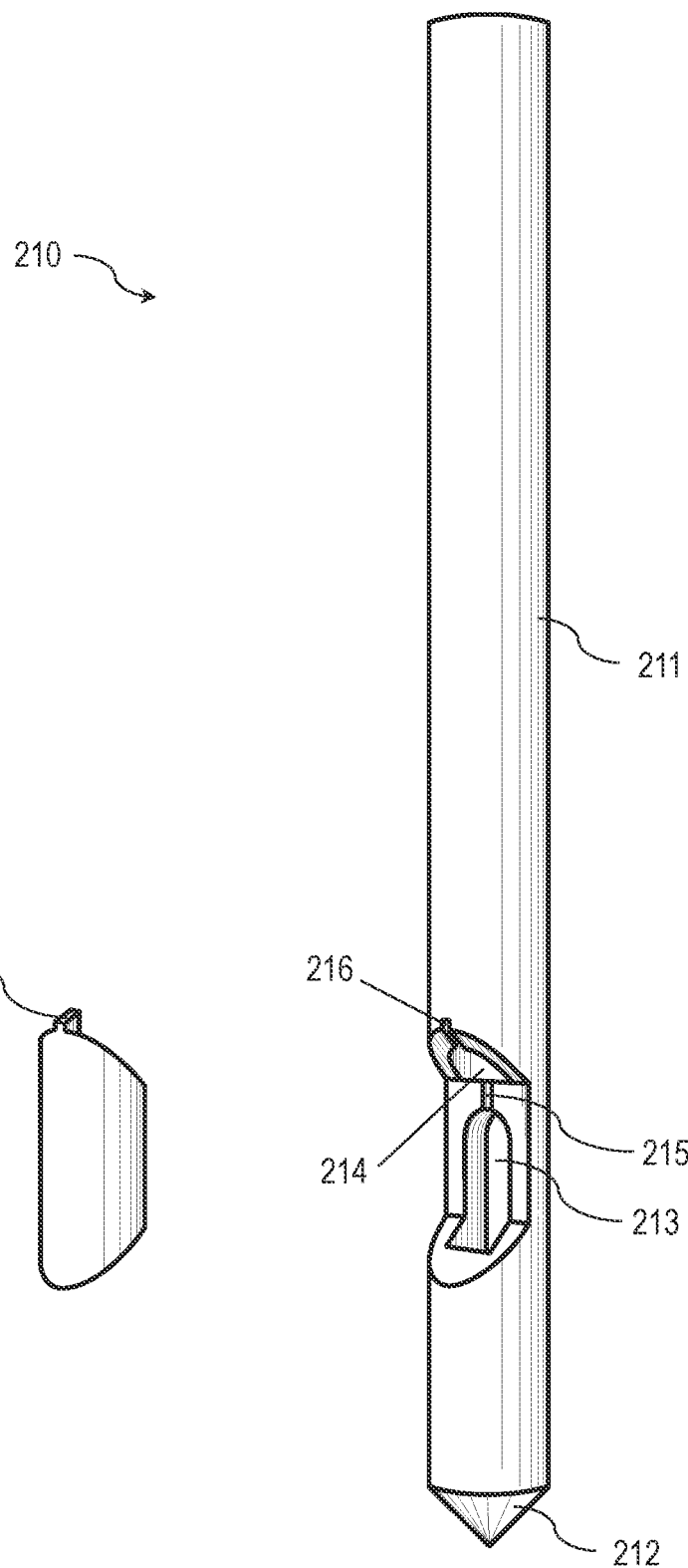
FIG. 6D is a perspective profile view illustrating an example casing and cover.
Figure 6E:
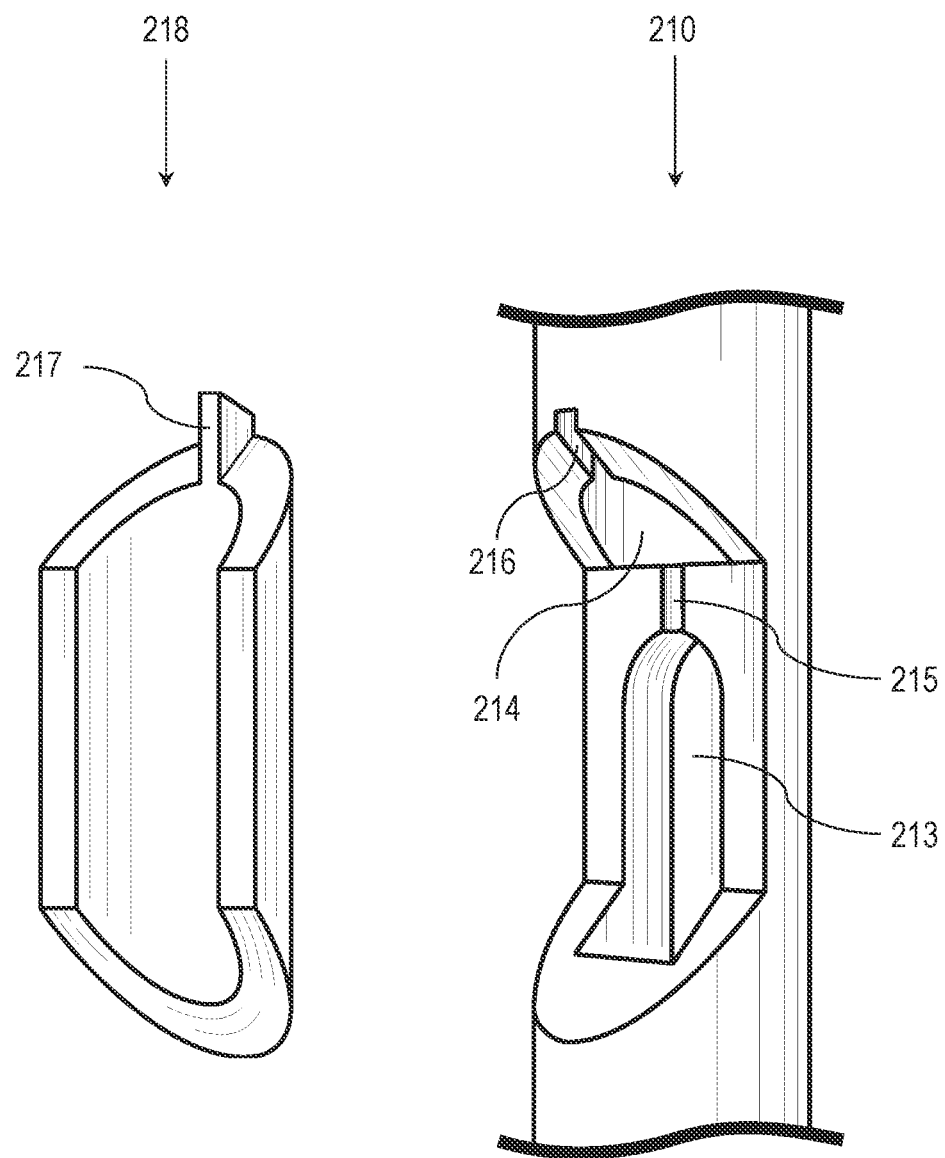
FIG. 6E is a close-up perspective view illustrating an example cover and a partial view of an example casing.

FIG. 6B is a side profile view illustrating casing 210 and cover 218. FIG. 6C is a rear profile view illustrating casing 210 and cover 218. FIG. 6D is a perspective view illustrating casing 210 and cover 218. FIG. 6E is a close-up perspective view illustrating cover 218 and a partial view of casing 210. FIG. 6F is a top perspective view illustrating casing 210 and cover 218. As previously explained, channel 214 can be used to route a transmission line from sensor $S_1$ 240. As illustrated in FIG. 6F, channel 214 can also be used as a female interface for coupling casing 210 to conduit 220. For example, conduit 220 can have a male stem configured to snugly engage channel 214. Other means familiar to those of ordinary skill in the art can be used for coupling casing 210 to conduit 220 such as a threaded male/female interface. For example, channel 214 can have a female threaded portion configured to engage a male threaded stem of conduit 220. Alternatively, casing 210 can have a male threaded stem configured to engage a female threaded portion of conduit 220. FIG. 6G is a bottom profile view of casing 210 and cover 218. As best illustrated in FIGS. 6C, 6E, and 6G, cover 218 can have a half-cylindrical shape, which provides sensor $S_1$ 240 with sufficient room when housed within cavity 213.

FIGS. 28A and 28B illustrate another example system 2800 for providing a sensor $S_1$ 240 through hollow tube 230 to perform a sampling event. As shown, casing 2810 includes a base portion 2808 configured to house sensor $S_1$ 240 and support transmission line 2814 through and out of casing 2810. The transmission line 2814 can extend into a "U" shaped tube or conduit 2802 connected to casing 2810 via a connection extension 2806 with one or more fasteners 2816. Further, two or more conduits 2802 can be coupled together via one or more couplers and/or cable tie-downs 2804, secured by one or more fasteners 2818, to extend the reach of casing 2810 (and therefore sensor $S_1$ 240). Casing 2810 can have a removable cover 2812, which allows access to sensor $S_1$ 240. The cover 2812 can be secured by snap fit, fasteners, adhesive, welding, etc., and can further include one or more gaskets (e.g., foam, rubber, polymer, etc.) to seal the casing interior from moisture, dirt, etc. In some examples, sensor $S_1$ 240 can be molded within casing 2810. In still other examples, sensor $S_1$ 240 can be encased and/or molded within casing 2810 such that no cover 2812 is needed.

Casing 2810 and conduit 2802 can be configured to slidably engage the hollow tube 230 directly, which can be dimensioned to slidably engage hollow tube 230. For example, one or more of hollow tube 230 and casing 2810 can be made of plastic, polyvinyl chloride (PVC), metal, or any other suitable material such that casing 2810 is capable of sliding within channel 232 to different vertical positions. In some examples, casing 2810 remains in contact with hollow tube 230 to enable dispersive waves to be received by sensor $S_1$ 240 housed within.

As disclosed herein, casing 2810 can be positioned at different vertical positions within channel 232 by securing casing 2810 to conduit 2802, and inserting one or more connected conduits into hollow tube 230. One or more such conduits 2802 can include a scale having incremental markings that indicate the length of each conduit. For example, the incremental markings can be spaced one inch apart. The scale can help identify the depth of casing 2810.

In some examples, casing 2810 is fully or partially housed within hollow tube 230, either in advance of driving hollow tube 230 into the ground and/or inserted following driving hollow tube 230 into the ground. In some examples, casing 2810 is configured to extend beyond an end of the hollow tube 230, and can itself be encased in an additional tip or other supportive structure (not shown) to facilitate driving hollow tube 230 and/or casing 2810 into the earth. In some examples, casing 2810 is dimensioned to fit within channel 232 and provided with a pointed tip 2820. In some examples, casing 2810 is dimensioned larger than channel 232, and/or may be fixed relative to hollow tube 230, such that extensions to hollow tube 230 and conduit 2802 together extend the reach of the sensor $S_1$ 240.

Conduit 2802 can further include a longitudinal channel to route a transmission line 2814 from sensor $S_1$ 240 through casing 2810 and to receiver 270. Further, the structure of conduit 2802 (e.g., the "U" shape), allows for directional orientation of sensor $S_1$ 240, even when inserted into hollow tube 230 at a substantial depth. FIG. 28B provides a view of the system 2800 with hollow tube 230 removed, exposing the conduit 2802.

In order to indicate the directionality of the sensor within hollow tube 230, a collar 2900 can be provided at an opening of one or more sections of hollow tube 230, as shown in the example of FIG. 29. Collar 2900 has a rectangular opening 2902 in the center that ensures that the U-shaped conduit 2802 cannot spin inside the tube, thereby ensuring that the orientation of sensor $S_1$ 240 is known and controlled during a sampling event. Collar 2900 includes direction arrows 2904 to orient the operator to place a sensing face of sensor $S_1$ 240 towards the foundation. Although described as a U-shaped conduit and substantially rectangular, any geometry and/or shape can be employed while maintaining the benefits of the disclosed system. For example, a generally cylindrical conduit with one or more flat surfaces can be employed, or a triangle or other shape with a flat or protruding surface to prevent unwanted turning of the sensor, and the shape of the opening 2902 can be adjusted accordingly.

FIG. 30 illustrates another view of the example conduit 2802. As shown, the conduit 2802 has a generally U-shape, with channel 2824 providing access for the transmission line 2814. The transmission line 2814 can be secured within the channel 2824 via one or more cable tie-downs 2804, as shown in FIG. 31. In examples employing multiple conduits 2802, the ends thereof can be joined by a coupler 2826, as shown in FIG. 32. One or more of the cable tie-downs 2804 and/or coupler 2826 can be secured to conduit 2802 via one or more fasteners and/or openings 2822 of the conduit 2802.

Returning to FIG. 2, system 200 can include a second sensor $S_2$ 250. Sensor $S_2$ 250 can be removably coupled to rod 260, which can be driven through the Earth 108 and into contact with buried concrete 102. Sensor $S_2$ 250 can be removably coupled to rod 260 using, for example, a magnet. Other means of removably coupling sensor $S_2$ 250 to rod 260 can be used. For example, adhesives such as tape or glue, or wax can be used. Rod 260 can be driven into contact with buried concrete 102 at a distance $D_2$ from a vertical edge of buried concrete 102. Distance $D_2$ can be any distance that permits a dispersive wave to be transmitted from the buried concrete 102 to hollow tube 230. Preferably, distance $D_2$ is within the range of about 1.5 to 3 feet, though other distances are possible and contemplated herein. The location of the vertical edge of buried concrete 102 can be determined or estimated using any method familiar to those of ordinary skill in the art. For example, although not illustrated, several rods can be driven into the Earth 108 in the proximity of the concrete structure to map out an estimated geometry of buried concrete 102.

Sensors $S_1$ 240 and $S_2$ 250 can be any type of sensors or transducers capable of or suitable for capturing and/or providing data relating to dispersive waves. In some embodiments, sensors 240 and 250 can be accelerometers that output data proportional to acceleration. For example, sensors 240 and 250 can be capacitive micro-electro-mechanical systems (MEMS) accelerometers, piezoresistive accelerometers, piezoelectric accelerometers, or the like, or any combination thereof. In other embodiments, sensors 240 and 250 can be velocity sensors that output data proportional to velocity. For example, sensors 240 and 250 can be moving coil velocity sensors, piezoelectric velocity sensors, or the like, or any combination thereof. In still other embodiments, sensors 240 and 250 can be displacement sensors that output data proportional to positional displacement. For example, sensors 240 and 250 can be capacitive displacement sensors, eddy-current displacement sensors, or the like, or any combination thereof. In still other embodiments, sensors 240 and 250 can include a combination of accelerometers, velocity sensors, and displacement sensors.

As will be appreciated by those of ordinary skill in the art, data output from sensors 240 and 250 can be processed, transformed, or the like. For example, displacement data output from a displacement sensor can be differentiated to provide velocity data, and differentiated a second time to provide acceleration data. Velocity data output from a velocity sensor can be differentiated to provide acceleration data. Similarly, acceleration data output from an accelerometer can be integrated to provide velocity data, and integrated a second time to provide displacement data. Velocity data output from a velocity sensor can be integrated to provide displacement data. The skilled artisan will appreciate that the processing or transforming of data can be achieved with a combination of hardware and/or software.

Figure 7A:
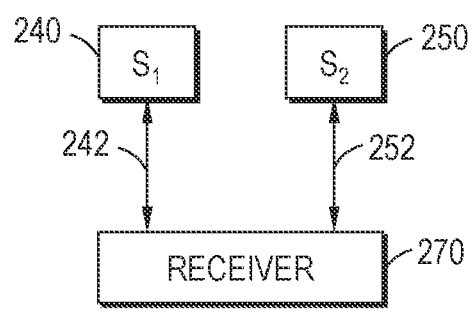
FIG. 7A is a simplified block diagram illustrating sensors in signal communication with a receiver according to some embodiments.

Data from sensors 240 and 250 can be transmitted to a receiver 270. For example, FIG. 7A is a simplified block diagram illustrating sensors 240 and 250 in communication with a receiver 270 according to some embodiments. The output of sensors 240 and 250 can include analog signals, digital signals, pulse-width modulated (PWM) signals, and other types of signals. Data generated by sensors 240 and 250 (i.e., sensor data) can relate to time, voltage, acceleration, velocity, displacement, and other information. Sensor data can be transmitted from sensors 240 and 250 to receiver 270 via wired or wireless connections 242 and 252, respectively. For example, in some embodiments, sensor data can be transmitted to receiver 270 via coaxial transmission lines (e.g., as illustrated in FIGS. 2-5). Other types of wired connections may also be used as will be apparent to those of skill in the art. In other embodiments, sensor data can be transmitted from sensors 240 and 250 to receiver 270 via a suitable wireless technology such as, for example, a radio frequency (RF) technology, near field communication (NFC), Bluetooth, Bluetooth Low Energy, IEEE 802.11x (i.e., Wi-Fi), Zigbee, Z-Wave, Infrared (IR), cellular, and other types of wireless technologies as will be apparent to those of skill in the art. Communication of sensor data from sensors 240 and 250 to receiver 270 can also comprise a combination of both wired and/or wireless connections.

Figure 7B:
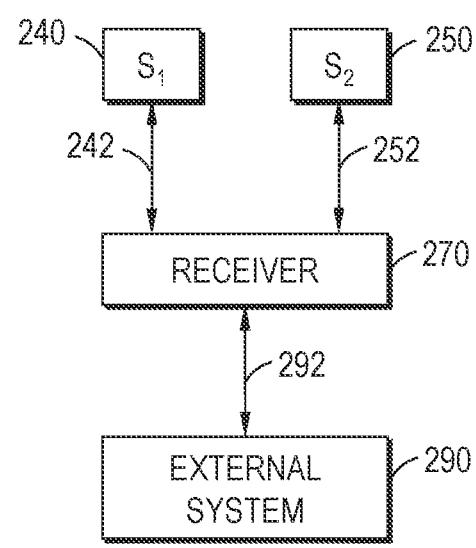
FIG. 7B is a simplified block diagram illustrating sensors in signal communication with a receiver, and a receiver in signal communication with an external system, according to some embodiments.

In some embodiments, such as that illustrated in FIG. 7B, receiver 270 can be in communication with an external system 290. In some embodiments, external system 290 can comprise a computing device such as a tablet, smartphone, laptop computer, desktop computer, or the like. For example, receiver 270 can be a data acquisition device (DAQ) and external system 290 can be a computer. In some embodiments, external system 290 can be a network, such as a private network, the Internet, or the like. It should be noted that external system 290 need not be a single system. Rather, external system 290 can comprise a combination of computing devices, networks, servers, the Internet, or the like. Communication medium 292 can comprise a wired or wireless connection. For example, in some embodiments, communication medium 292 can be a wired connection, such as a coaxial transmission line, USB cable, Ethernet cable, and other types of wired connections as will be apparent to those of skill in the art. In other embodiments, communication medium 292 can be a suitable wireless technology such as, for example, a radio frequency (RF) technology, near field communication (NFC), Bluetooth, Bluetooth Low Energy, IEEE 802.11x (i.e., Wi-Fi), Zigbee, Z-Wave, Infrared (IR), cellular, and other types of wireless technologies as will be apparent to those of skill in the art. In the case of external system 290 comprising multiple systems or devices, communication media 292 can comprise a combination of both wired and/or wireless connections using any of the aforementioned technologies. Further, external system 290 need not be located near receiver 270. Indeed, receiver 270 can be located on a work site while external system 290 can be located elsewhere, such as an office or laboratory.

Figure 7C:
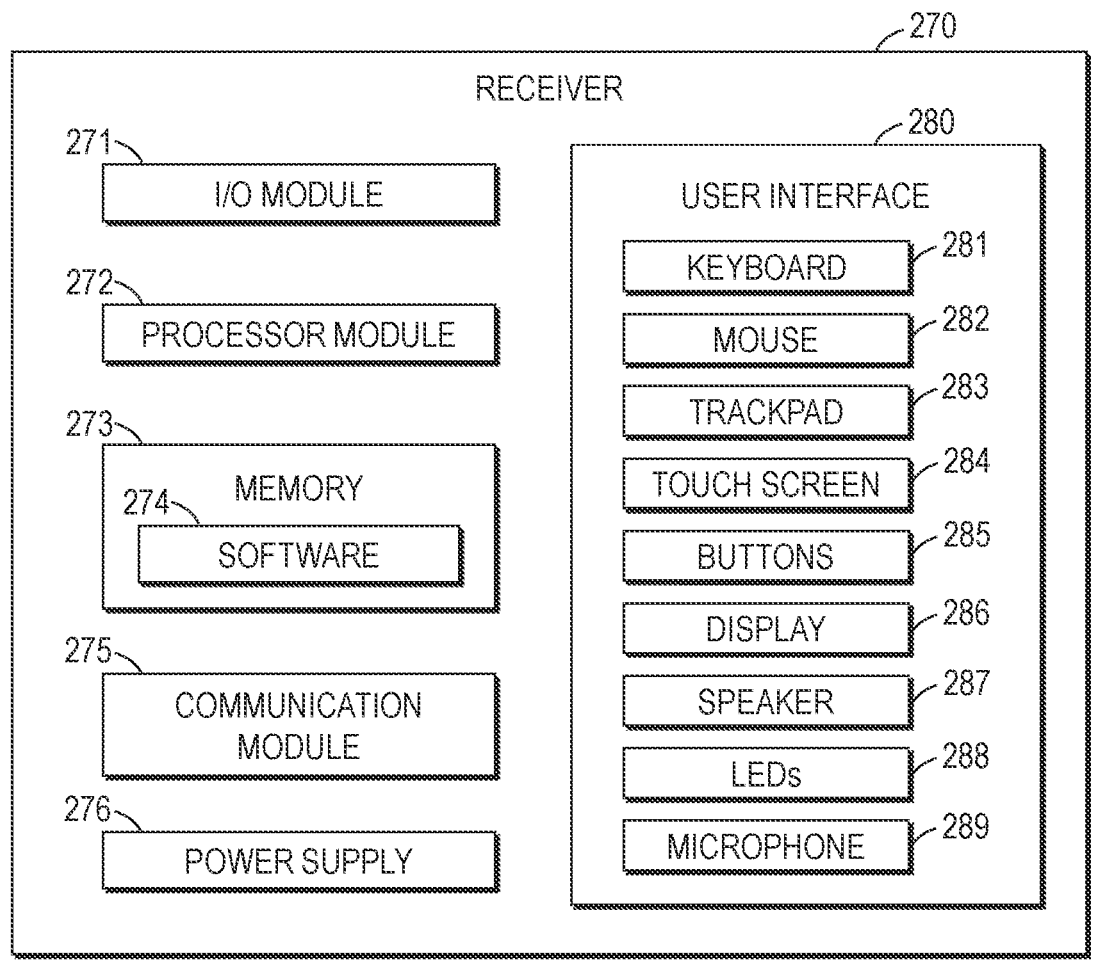
FIG. 7C is a functional block diagram illustrating an example receiver according to some embodiments.

Receiver 270 can include hardware, firmware, and/or software that generally enables a user to interact with the system, to receive data from sensors 240 and 250, to process the data, to analyze the data, to store the data, and/or to transmit the data to external system 290. FIG. 7C is a block diagram illustrating an example receiver 270 according to some embodiments. The receiver 270, which is communicatively coupled to sensors 240 and 250 via communication media 242 and 252, respectively, can receive sensor data from sensors 240 and 250 via an input/output (I/O) module 271. The I/O module 271 can send the data to processor module 272.

Processor module 272 can be coupled to one or more memory devices 273. The one or more memory devices 273 can store data, such as data received from sensors 240 and 250, data received from a user, and data received from an external system 290. The one or more memory devices 273 can also store software 274 (i.e., computer-executable instructions). Processor module 272 can process data, wherein the processing can include, for example, amplifying, converting from analog to digital or digital to analog, conditioning, filtering, and/or transforming the data. Processor module 272 can also serve as a central control unit of receiver 270. For example, software 274 can comprise operating system software, firmware, and other system software for controlling receiver 270 and its components. Software 274 can further include data processing software, application software, or the like, as discussed in more detail below.

Receiver 270 can include a user interface 280 that comprises input and output components configured to allow a user to interact with receiver 270. For example, user interface 280 can include a keyboard 281, mouse 282, trackpad 283, touch-sensitive screen 284, one or more buttons 285, display 286, speaker 287, one or more LED indicators 288, and microphone 289. Processor module 272 can control user interface 280 and its components. For example, processor module 272 can receive data and commands from input components through I/O module 271 and provide data and commands to output components through I/O module 271. Processor module 272 can execute software 274 stored in the one or more memory devices 273 to cause a graphical user interface (GUI) to be displayed on display 286. The GUI can provide the user with an intuitive and user-friendly means for interacting with the system, including to provide output to the user such as prompts, messages, notifications, warnings, alarms, or the like.

The components of the user interface 280 include controls to allow a user to interact with the receiver 270. For example, the keyboard 281, mouse 282, and trackpad 283 can allow input from the user. The touch-sensitive screen 284 can enable a user to interact with the GUI, for example, by inputting information, making selections, or the like. The one or more buttons 285 can provide for quick and easy selection of options or modes, such as by toggling functions on/off. The display 286 can be any type of display, such as an LCD, LED, OLED, or the like. The display 286 can provide the user with visual output. The speaker 287 can provide the user with audible output, such as by alerting the user of notifications, warnings, alarms, or the like. The one or more LED indicators 288 can provide the user with visual indications. For example, one LED indication might represent whether there is sufficient battery power, or whether the receiver is receiving power from an external source. Another LED indication might inform the user whether the receiver 270 is in an active state and measuring data received from sensors 240 and 250. The microphone 289 can provide a user with the capability to control receiver 270 by voice. Although not illustrated, the user interface 280 can include other components, such as a vibrating module to provide a user with tactile signals or alerts, a backlight to facilitate viewing the display in low light conditions, or the like.

As further illustrated in FIG. 7C, receiver 270 can include communication module 275, which can comprise components, such as transceivers, drivers, antennas, and the like, to enable communication with various types of devices and systems. For example, communication module 275 can include Ethernet ports, USB ports, and ports for communicating over RS-232, RS-422, RS-485, and other protocols. Communication module 275 can further include antennas and other components typically used for wireless communication, such analog frontend circuitry, A/D converters, amplifiers, filters, and the like. Communication module 275 can enable communication with an external system 290. For example, an external system 290 may send commands or data to, or receive commands or data from, receiver 270. Communication module 275 may also enable receiver 270 to receive software updates. Thus, communication module 275 is a two-way communication module that enables receiver 270 to communicate with an external system 290 or other devices.

As further illustrated in FIG. 7C, receiver 270 can include a power supply 276, which can include rechargeable or disposable batteries. Power supply 276 may also include circuitry to receive power from an external source and to supply the necessary power to receiver 270, such as through an AC adapter. In some embodiments, the external source can be a computer that supplies power to receiver 270 over a USB cable.

Receiver 270 can support various other functions. For example, in some embodiments, receiver 270 can include the ability to record and playback data events received from sensors 240 and 250, while also permitting for real-time display of the events. In some embodiments, receiver 270 can include the ability to tag events as they occur. For example, receiver 270 can include one or more buttons 285 that enables a user to insert a marker onto data in real-time. In some embodiments, receiver 270 can permit remote control and monitoring. For example, receiver 270 can be communicatively coupled to an external system 290 to enable the external system 290 to view data events in real time and to control receiver 270.

It should be noted that FIG. 7C is a block diagram and not a strict architectural diagram. Thus, FIG. 7C generally illustrates the components in receiver 270, some of which may be combined and some of which may be separated. For example, some or all of the functionality of the I/O module 271 might be combined with some or all of the functionality of the communication module 275 and vice versa. As another example, communication module 275 may comprise several individual modules, some of which may communicate with sensors 240 and 250 via wired or wireless connections, while others may communicate with external system 290 via a wired or wireless connection. As yet another example, processor module 272 may comprise several components, such as discrete processing elements for amplifying, converting, conditioning, filtering, and transforming data, and a microprocessor and/or microcontroller for controlling receiver 270 (in addition to performing other functions, such as further processing data). Further, the blocks illustrated in FIG. 7C are communicatively coupled in an appropriate manner as would be appreciated by one of ordinary skill in the art. For example, the components can be communicatively coupled with a bus. Thus, commands, data, and other information received from the I/O module 271 and communication module 275 could be transmitted to processor module 272 for processing, storing, and or other action. Similarly, processor 272 could transmit commands, data, and other information to I/O module 271 and communication module 272, as appropriate, to be further communicated to other components, such as sensors 240 and 250, external system 290, and user interface 280 and its components.

Software 274 on receiver 270 can be programmed to perform a variety of functions. For example, as explained above, software 274 can comprise instructions that, when executed by processor module 272, cause processor module 272 to generate a graphical user interface (GUI) on display 286. The GUI can allow a user to interact with the system. Software 274 can further comprise instructions that, when executed by processor module 272, cause processor module 272 to receive data from sensors, process the data, and analyze the data to determine whether the data is usable or suitable for calculating a thickness of a buried concrete structure. Software 274 can further comprise instructions that, when executed by processor module 272, cause processor module 272 to analyze data received from sensors and calculate the thickness of a buried concrete structure.

It should be noted that software 274 described herein is not limited to residing on, or being executed by, receiver 270. Instead, some or all of the software may reside on or be executed by external system 290. As one non-limiting example, software 274 on receiver 270 may receive data from a sensor resulting from the sensor being excited by a dispersive wave. Software 274 on receiver 270 can process the sensor data and provide feedback as to whether the sensor data is usable or suitable to calculate a thickness of a buried concrete structure. After a positive determination is made for necessary data, the data can be analyzed in real time to determine the thickness of the buried concrete structure. Alternatively, the data can be stored and analyzed at a later time. As another alternative, the sensor data can be communicated to external system 290, which can include software that analyzes the sensor data (in real time or at a later time) to determine a thickness of the buried concrete structure. Thus, the inventions disclosed herein contemplate a distributed architecture in which sensor data can be procured and analyzed on site, off site, or a combination of both.

Returning to FIG. 2, the general operation of the system 200 for estimating the thickness T of buried concrete 102 is now provided. As disclosed herein, dry parallel seismic (dry PS) testing is a nondestructive method for determining the thickness of structural foundations (e.g., thin concrete) that are below-grade (e.g., buried). Following an impact to the buried concrete portion or pad generating one or more waves, resulting signals are collected as one or more data sets at one or more (e.g., incremental) depths. In conventional methods, after a data set is collected, it is necessary to have a signal analyst review the data set manually before it could be determined conclusive enough to make a prediction about the thickness of concrete. Requiring a signal analyst to manually validate data, such as during a so-called call-off process, poses a variety of problems, including communication when field operators and signal analysts are located in different time zones. The need therefore exists for system and methods to avoid operator signal analysis and data evaluation.

Due to the inaccessibility of the surface of the buried concrete portion, dry PS testing is used to determine thickness of buried structural foundations. The dry PS test employs a rod that is driven into the ground such that the rod comes into contact with the buried concrete portion (e.g., a top surface of the foundation pad). The rod is oriented perpendicular to a plane corresponding to a horizontal surface of the buried concrete portion. An impulse is generated by exciting an exposed portion (e.g., a top) of the rod, such as by employing a striking instrument (e.g., a handheld hammer, a mechanical force mechanism, etc.). The excitation generates one or more waves that travel downward through the rod and then through the concrete or other materials of the buried concrete portion.

Some energy from the excitation is transmitted through the concrete/soil boundary, which radiates outward into the surrounding soil. One or more sensors can be arranged within a conduit, tube, pipe or other physical channel. In some examples, the sensor(s) are oriented relative to the buried concrete portion (e.g., parallel to a vertical edge of the concrete of the structural foundation) to detect arrival of the waves radiating outwardly from the buried concrete portion. The sensor(s) generate signals associated with the waves, which can be transmitted to a receiver 270 (e.g., via a wired or wireless transmission channel) as explained above.

Figure 8:
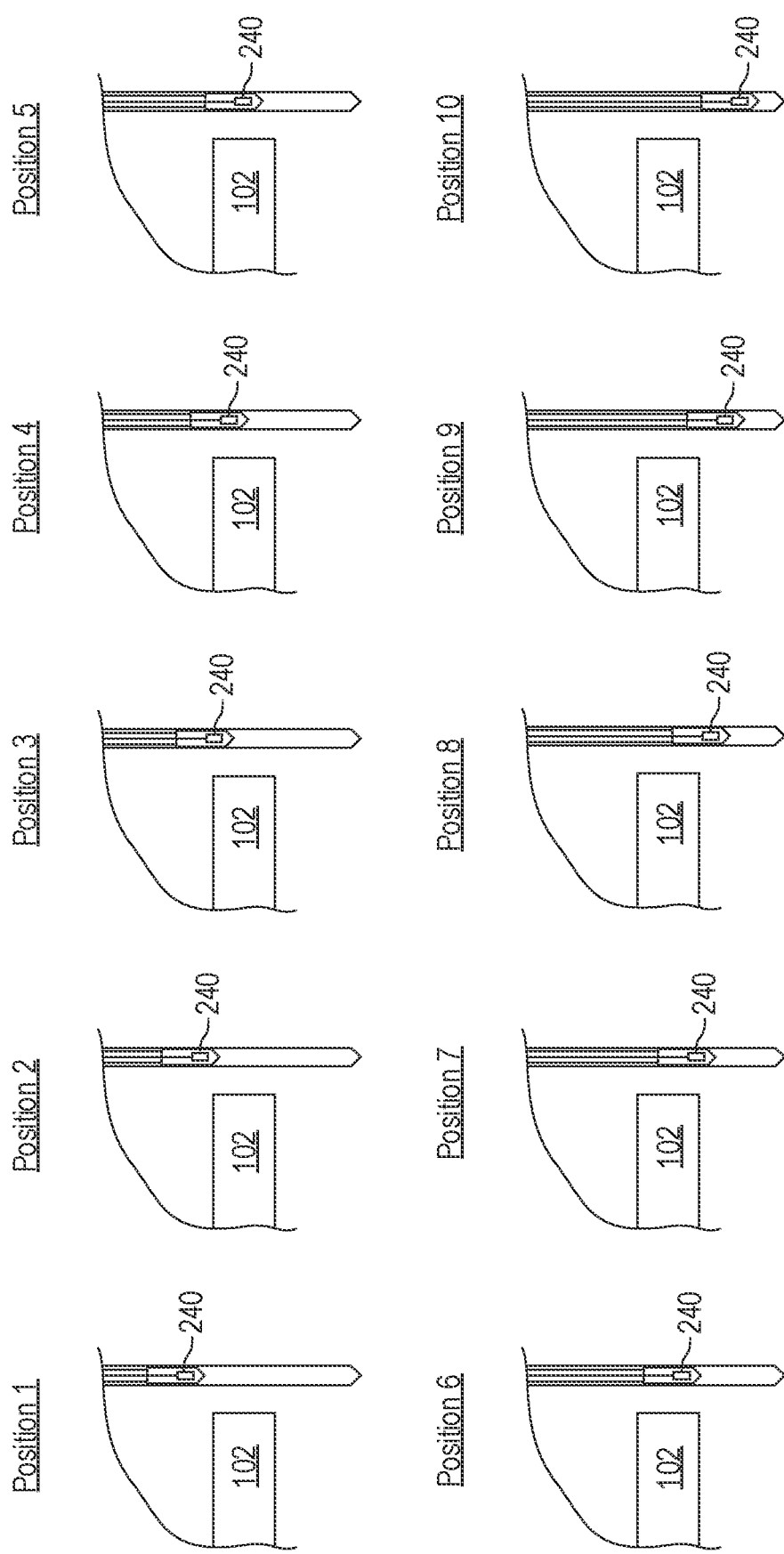
FIG. 8 is a schematic diagram illustrating example positions for an accelerometer near buried concrete.

For example, as shown in FIG. 2, sensor $S_1$ 240 is located in channel 232 at a distance approximately above the top surface of buried concrete 102, a dispersive wave is generated and transmitted down rod 260 to trigger sensor $S_2$ 250, which represents time $T_0$. A dispersive wave can be generated, for example, by striking the top of rod 260. A dispersive wave can be generated by other means, such as with an impact device. The dispersive wave continues down rod 260 and is transmitted to buried concrete 102. At least a portion of the dispersive wave is emanated from the buried concrete 102, transmitted through the Earth 108, and is received by hollow tube 230. The dispersive wave is transmitted from hollow tube 230 to casing 210, which is in contact with hollow tube 230. The wave is then transmitted to sensor $S_1$ 240, which is in contact with casing 210. The time when the dispersive wave triggers sensor $S_1$ 240 can represent time $T_1$. Sensor $S_1$ 240 can then be incrementally lowered to various positions within channel 232, which is illustrated in FIG. 8. At each incremental position, the above process can be repeated until sensor $S_1$ 240 is beneath the bottom of buried concrete 102. The time elapsed from $T_0$ to $T_1$ for each incremental position can be correlated with the location of sensor $S_1$ 240 when each wave was generated to estimate the thickness of buried concrete 102.

Figure 9A:
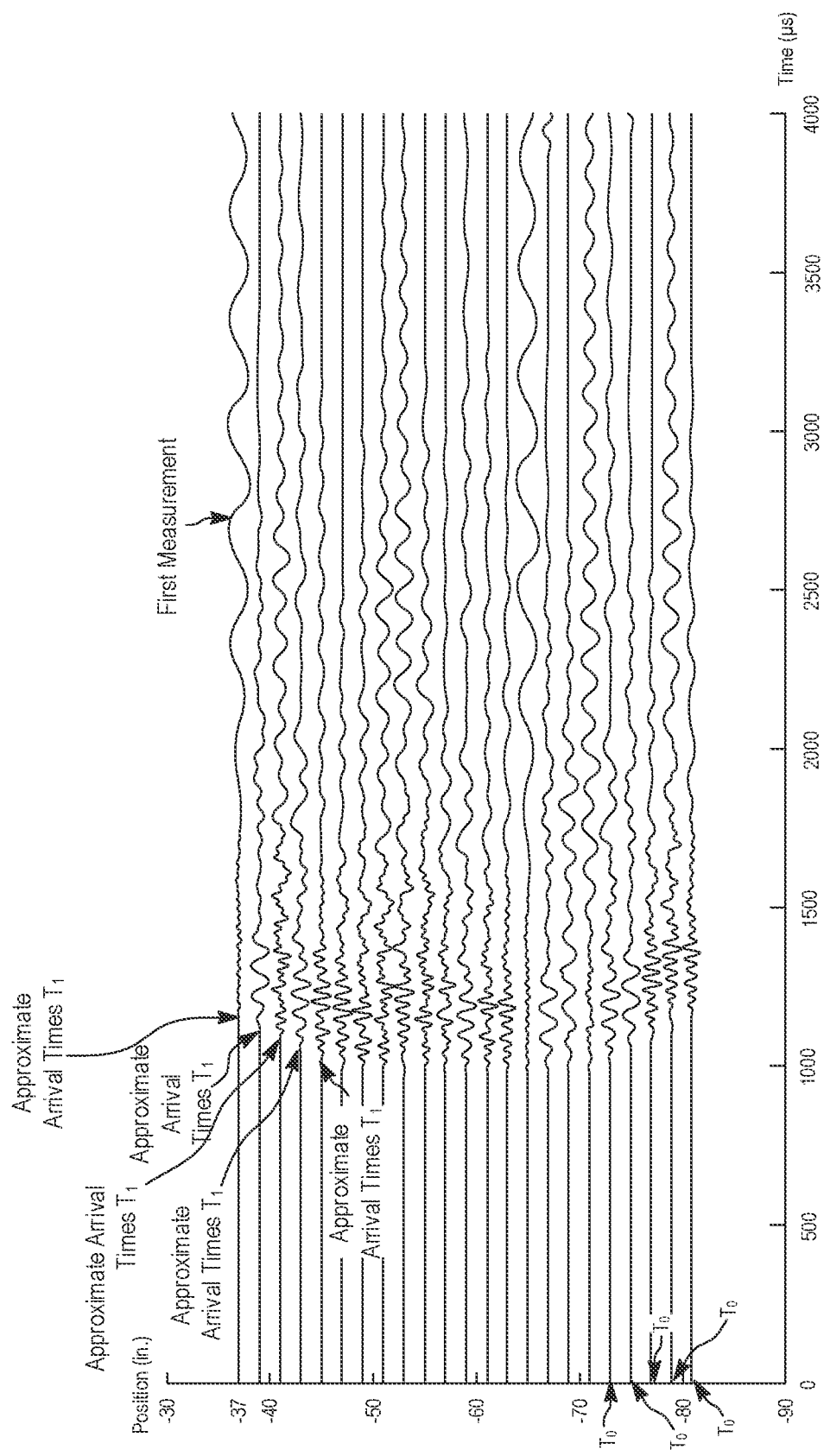
FIG. 9A is a graph diagram illustrating an example plot for estimating the thickness of buried concrete.

For example, FIG. 9A is a graph diagram illustrating an example plot for estimating the thickness of buried concrete 102. In FIG. 9A, time is plotted on the horizontal axis in microseconds and the vertical position of sensor $S_1$ 240 is plotted on the vertical axis in inches. In this example, sensors $S_1$ and $S_2$ comprised accelerometers $A_1$ 240 and $A_2$ 250. In the example graph of FIG. 9A, the arrival times of the dispersive waves at accelerometer $A_2$ 250 (when accelerometer $A_2$ 250 is triggered at time $T_0$) are represented by time=0 for each waveform. The approximate arrival times of the dispersive waves at accelerometer $A_1$ 240 (when accelerometer $A_1$ 240 is triggered at time $T_1$) are represented graphically as the point at which each waveform transitions from an approximate steady state to a non-zero amplitude. In this example, 23 measurements were made (illustrated by the 23 waveforms) beginning with accelerometer $A_1$ 240 placed at −37 inches, which represents the approximate depth of accelerometer $A_1$ 240 below the surface of the ground 106. That depth may have been chosen, for example, by first determining the approximate depth of the surface of the buried concrete, then placing accelerometer $A_1$ 240 a short distance above that depth. Each of the 22 subsequent measurements were made by incrementally lowering accelerometer $A_1$ 240 by approximately 2 inches. Thus, there are 23 values for $T_0$ (all of which are time=0) and 23 values for $T_1$, each corresponding to a different vertical position for accelerometer $A_1$ 240.

Figure 9B:
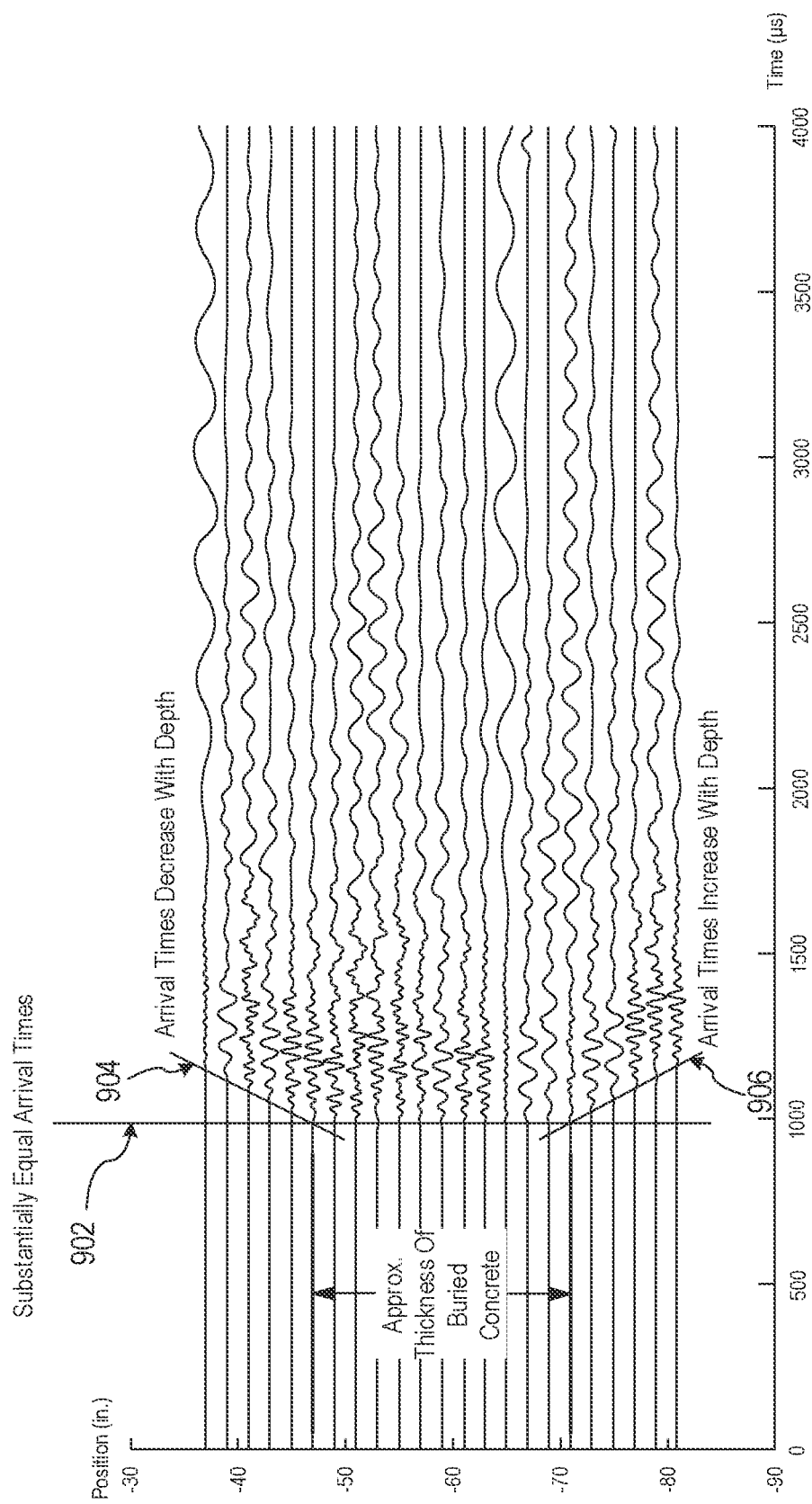
FIG. 9B is a graph diagram illustrating an example plot for estimating the thickness of buried concrete.

FIG. 9B is a graph diagram illustrating how the thickness of buried concrete 102 can be estimated based on at least the times of arrival of the dispersive waves at accelerometer $A_1$ 240. The arrival times for the dispersive waves at accelerometer $A_1$ 240 that are substantially equal may be grouped. This is illustrated by vertical line 902 in the example graph of FIG. 9B. The non-vertical lines 904 and 906 in the example graph of FIG. 9B illustrate arrival times that increase and/or decrease with depth, indicating a spatial relationship between the time it takes the dispersive wave to reach accelerometer $A_1$ 240 and the location of accelerometer $A_1$ 240. In the example graph of FIG. 9B, 12 arrival times at accelerometer $A_1$ 240 are grouped (illustrated by the 12 waveforms between the non-vertical lines 904 and 906). Because each of these 12 arrival times corresponds to a 2-inch incremental vertical displacement of accelerometer $A_1$ 240, it can be estimated that the thickness of buried concrete 102 is approximately 24 inches.

Several items are noted here. First, although the explanation above and FIG. 8 illustrates sensor $S_1$ 240 beginning above buried concrete 102 and being incrementally lowered, the invention is not limited in this fashion. For example, sensor $S_1$ 240 can begin beneath buried concrete 102 and incrementally raised. As another example, sensor $S_1$ 240 can be placed at any position within channel 232 that is above, below, or approximately equal to, the depth of buried concrete 102. The thickness of the buried concrete 102 can still be estimated because there will be a group of waveforms having substantially equal times of arrival at sensor $S_1$ 240, and each waveform corresponds to a vertical position (which can be known, for example, with a scale labeled on connection 242 (if connection 242 is a wired connection) or on conduit 220). Thus, the order in which sensor $S_1$ 240 is placed in different vertical positions is not a limitation of the invention.

Second, the example graphs of FIGS. 9A and 9B illustrate ideal conditions in that the vertical placement of accelerometer $A_1$ 240 was at approximately distance $D_1$ each time a measurement was made. In practice, these ideal conditions may not always occur or be possible to achieve. For example, hollow tube 230 may be driven at a slight angle relative to a vertical edge of the buried concrete 102. As a result, some measurements may be taken at distance $D_1$ while other measurements may deviate from distance $D_1$. Nevertheless, the thickness of buried concrete 102 can still be estimated because the times of arrival at accelerometer $A_1$ 240 should have a definable trend. That is, a group of waveforms should still exhibit approximately equal arrival times with some constant delay factor, whereas the waveforms corresponding to vertical placements for accelerometer $A_1$ 240 that are above or below buried concrete 102 should deviate by a degree greater than the delay factor. As a result, vertical line 902 illustrated in FIG. 9B may be angled.

Third, although the invention described above utilized one sensor that is incrementally displaced below the surface of the ground for each measurement, multiple sensors can be used. For example, similar results can be achieved by serially bundling multiple sensors, such as accelerometers, in a vertical orientation at known distances and incrementally moving the bundle. As one example, two sensors can be bundled 2 inches apart in a vertical direction. In this way, when one dispersive wave is generated, it will trigger two sensors (not including sensor $S_2$ 250, which is triggered at time $T_0$), thereby cutting the amount of measurements in half. As another example, 12 sensors can be bundled 1 inch apart in a vertical direction. Thus, from one dispersive wave, it may be possible to determine 12 times of arrival that correspond to 12 inches. Thus, the invention is not limited to using any particular number of sensors.

Figure 3:
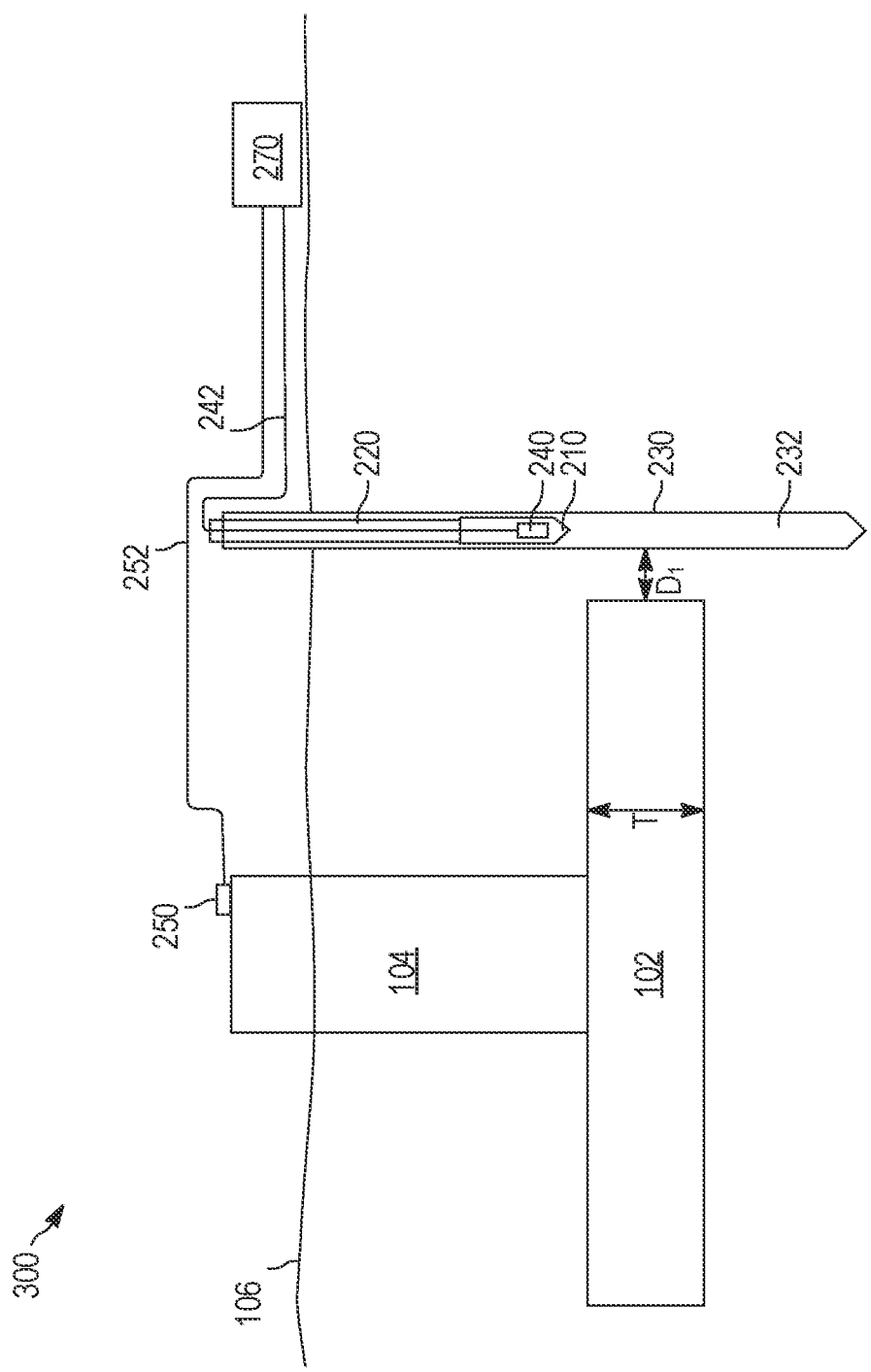
FIG. 3 is a schematic diagram illustrating an example setup of a system for estimating the thickness of buried concrete.

FIG. 3 is a schematic diagram illustrating an alternative example setup of a system 300 for estimating the thickness of buried concrete 102. The primary differences between systems 200 and 300 concern where sensor $S_2$ 250 can be located and how a dispersive wave is generated. As illustrated in FIG. 3, sensor $S_2$ 250 can be removably coupled to exposed concrete 104 instead of to rod 260. Sensor $S_2$ 250 can be removably coupled to exposed concrete 104 using, for example, wax. Other means of removably coupling sensor $S_2$ 250 to exposed concrete 104 can be used. For example, adhesives such as tape or glue can be used. Additionally, a dispersive wave can be generated in system 300 by exciting exposed concrete 104 instead of rod 260. Besides these noted differences, the remainder of the general operation of system 300 is the same as the general operation of system 200. Therefore, it will be appreciated that the other details explained in connection with system 200 illustrated in FIG. 2 apply to system 300 illustrated in FIG. 3 and are therefore not repeated.

Figure 4:
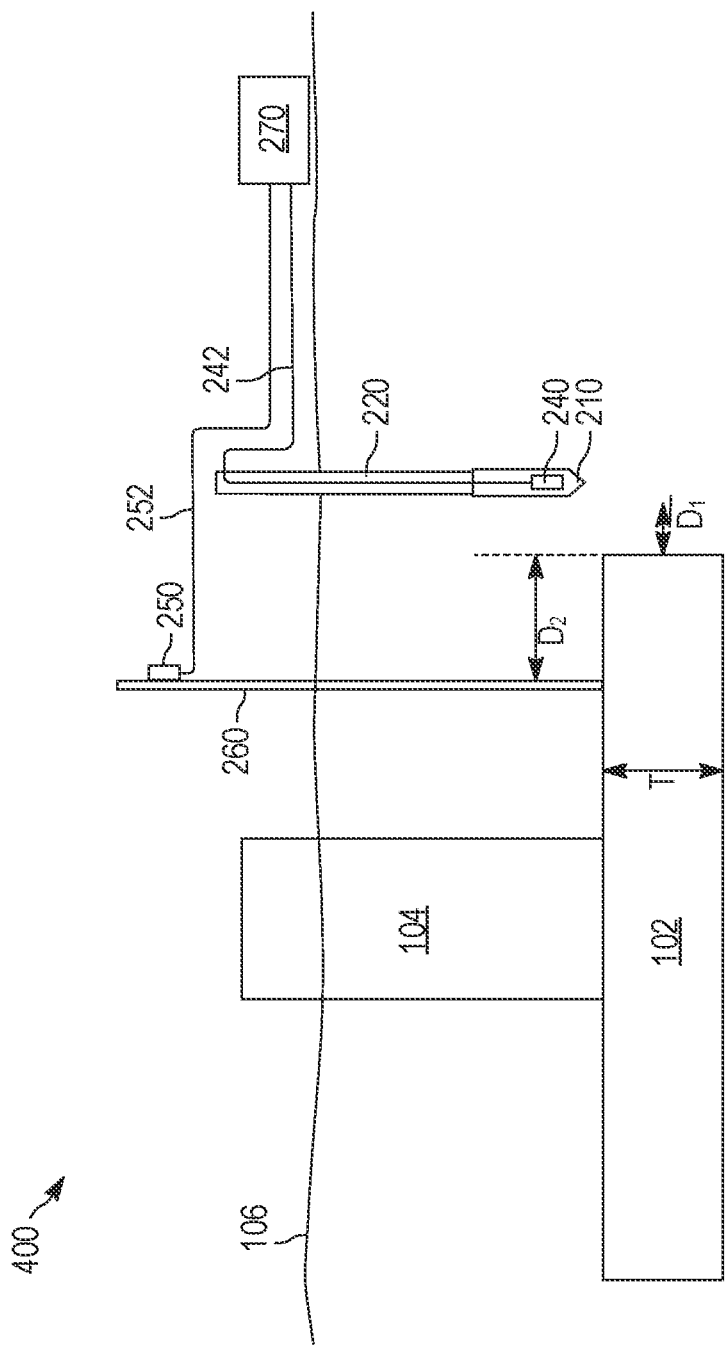
FIG. 4 is a schematic diagram illustrating an example setup of a system for estimating the thickness of buried concrete.

FIG. 4 is a schematic diagram illustrating an alternative example setup of a system 400 for estimating the thickness of buried concrete 102. The primary differences between systems 200 and 400 concern how sensor $S_1$ 240 can be placed at different vertical positions in the Earth 108. As illustrated in FIG. 4, sensor $S_1$ 240 can be placed at different vertical positions by driving casing 210 directly into the Earth 108, for example, by striking conduit 220. This is an alternative to a casing slidably engaging a hollow tube as explained above in connection with FIG. 2.

Figure 10:
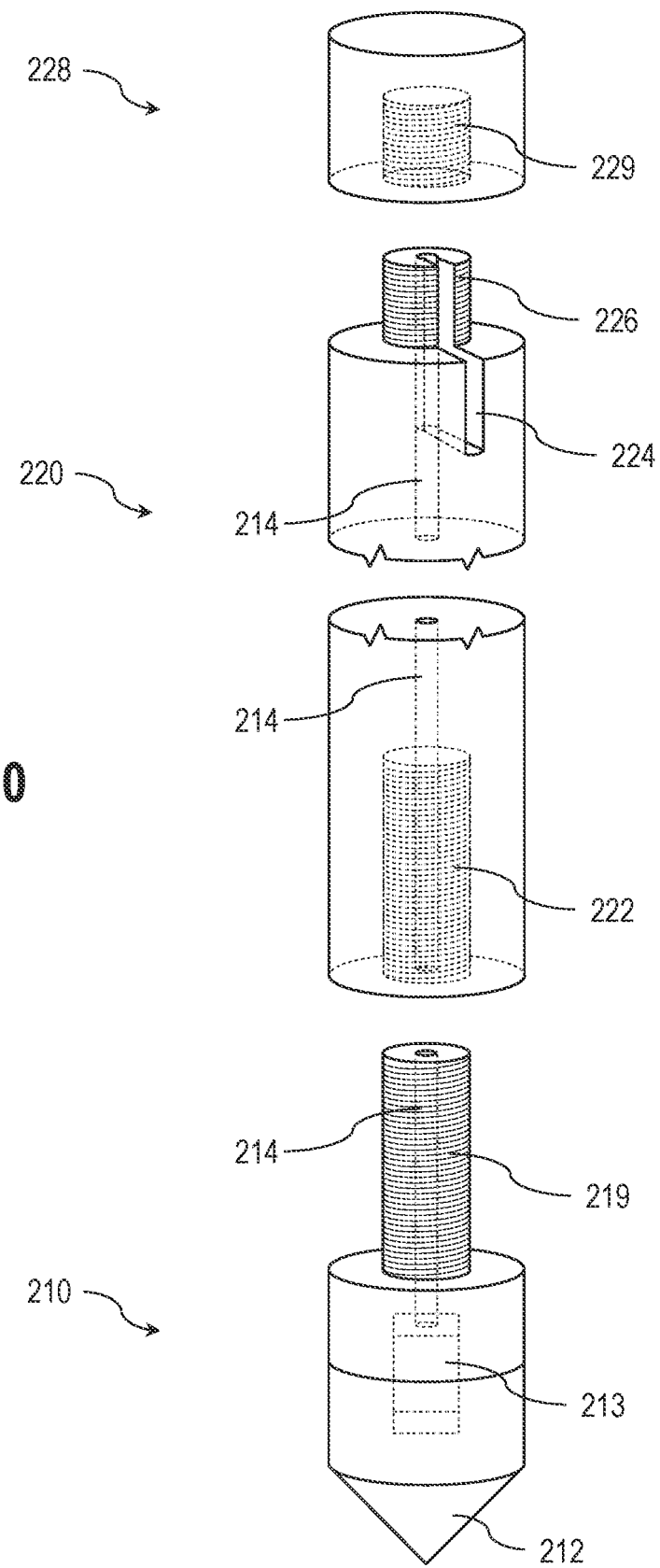
FIG. 10 is a perspective view illustrating an example casing and conduit that can be used to estimate the thickness of buried concrete.

FIG. 10 is a perspective view illustrating an example casing 210 and conduit 220 that can be used in system 400. Casing 210 can include a pointed tip 212 to help facilitate driving casing 210 into the Earth 108. Casing 210 can further include a stem 219 having male threads configured to engage conduit 220. Casing 210 can further include a cavity 213 (shown in phantom in FIG. 10) that is dimensioned to securely house sensor $S_1$ 240 (not shown).

Conduit 220 can include a female threaded portion 222 (shown in phantom in FIG. 10) configured to engage the stem 219 of casing 210. Conduit 220 can further include a slot 224 through which a transmission line 242 (not shown) can be routed. Slot 224 can help protect transmission line 242 from being damaged when casing 210 is driven into the Earth 108. Conduit 220 can further include a stem 226 having male threads configured to engage a cap 228, which cap 228 can include a female threaded portion 229 (shown in phantom in FIG. 10). Cap 228 can be secured to conduit 220 so that conduit 220 may be struck to drive casing 210 into the Earth 108. As previously explained, conduit 220 can comprise one piece of a desired length, or can comprise multiple sections that engage one another, for example, using male/female interfaces (not shown), to extend conduit 220 to a desired length. A longitudinal channel 214 (shown in phantom in FIG. 10) can extend from cavity 213, through stem 219, and through conduit 220 to accommodate routing transmission line 242 (not shown).

Figure 11B:
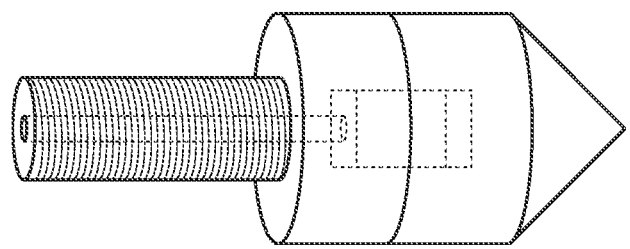
FIGS. 11A and 11B are perspective views illustrating an example casing that can be used to estimate the thickness of buried concrete.
Figure 11A:
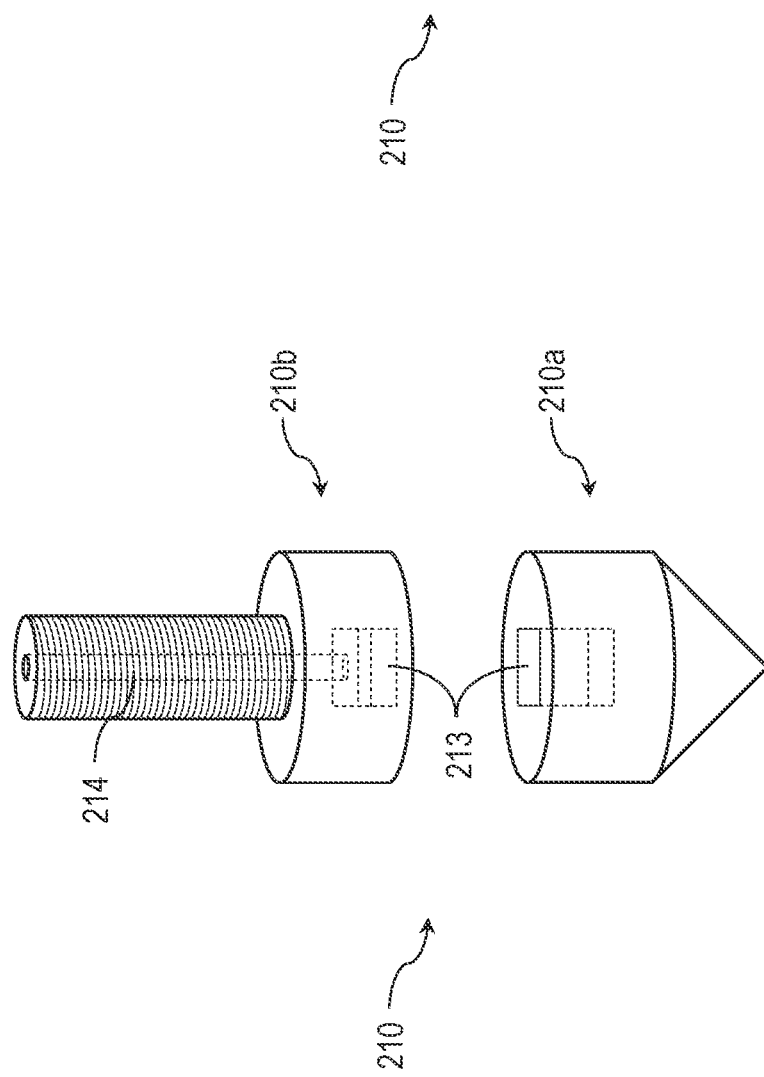
Figure 12A:
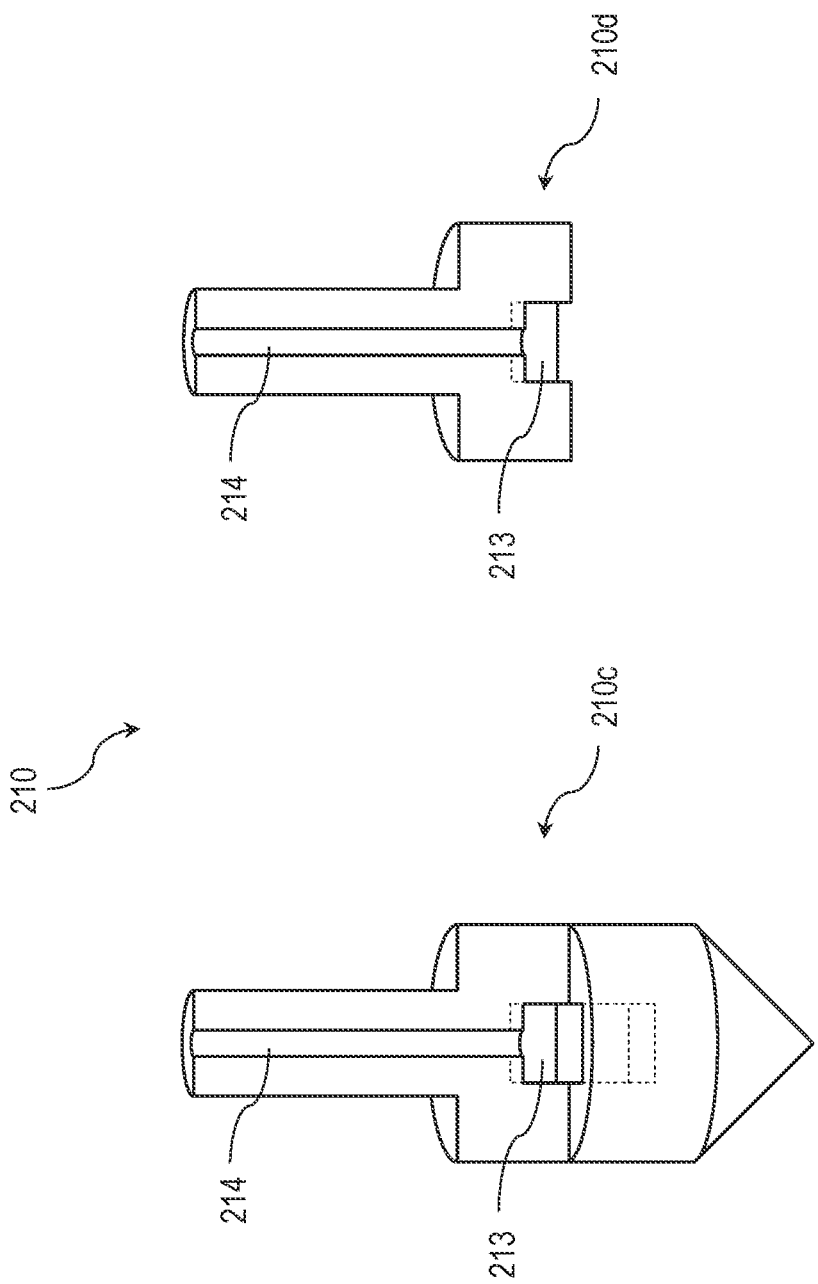
FIG. 12A is a perspective view illustrating an example casing that can be used to estimate the thickness of buried concrete.
Figure 12B:
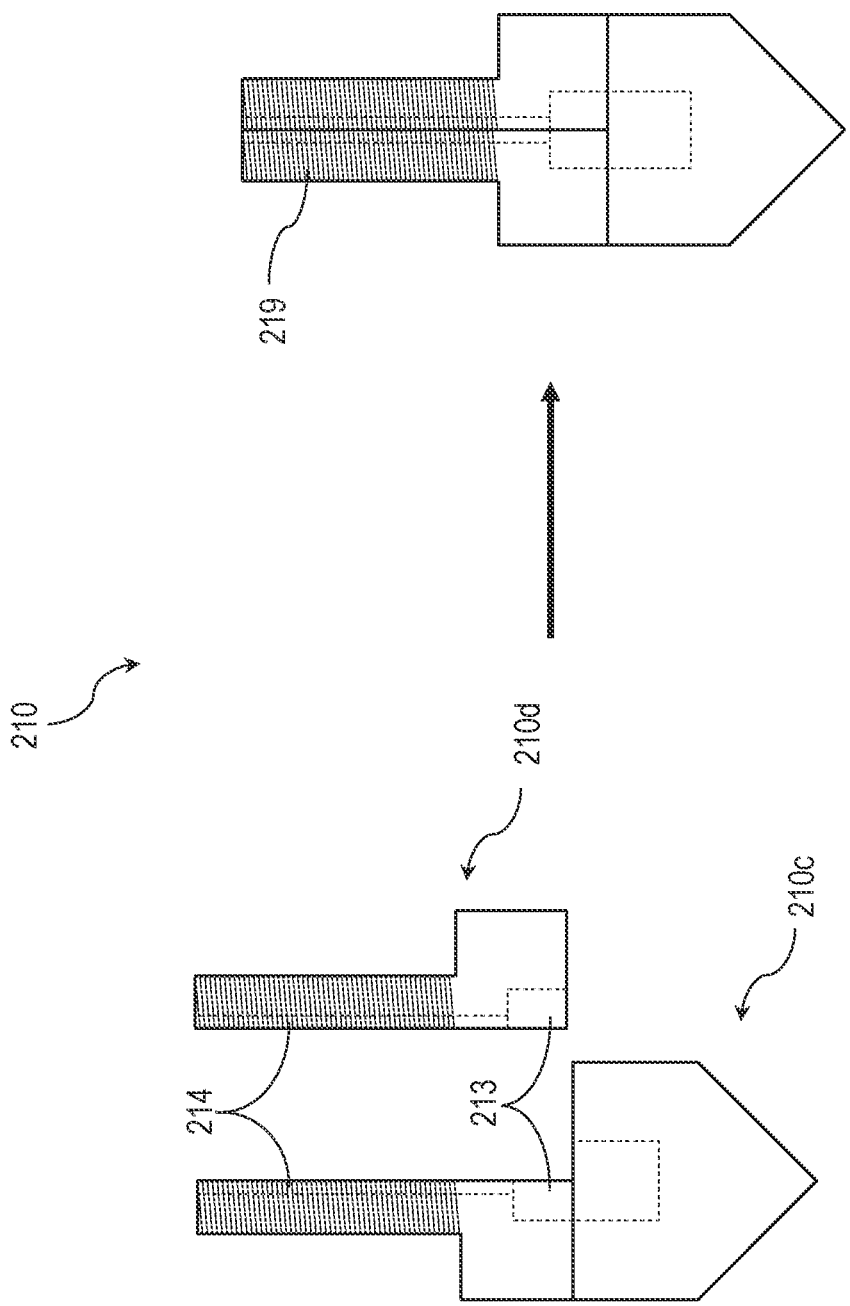
FIG. 12B is a profile view illustrating an example casing that can be used to estimate the thickness of buried concrete.

Casing 210 can comprise one piece or multiple pieces. For example, as illustrated in FIG. 11A, casing 210 can comprise a tip portion 210a and stem portion 210b. Sensor $S_1$ 240 (not shown) can be secured in cavity 213 with transmission line 242 (not shown) routed through longitudinal channel 214. Tip portion 210a can then be permanently joined to stem portion 210b, for example, by welding, to form casing 210 that is effectively one piece as illustrated in FIG. 11B. Alternatively, and preferably, as illustrated in FIG. 12A, casing 210 can comprise a primary assembly 210c and a removable portion 210d. Sensor $S_1$ 240 (not shown) can be secured in cavity 213 with a transmission line 242 (not shown) routed through longitudinal channel 214. Primary assembly 210c can then be joined with removable portion 210d as illustrated in FIG. 12B and held together when conduit 220 engages stem 219. It will be appreciated that other configurations are possible for securing sensor $S_1$ 240 in casing 210 and that the example embodiments shown in FIGS. 11A-12B are for illustration purposes only.

Besides driving casing 210 directly into the Earth 108 instead of using hollow tube 230, the remainder of the general operation of system 400 is the same as the general operation of system 200. Therefore, it will be appreciated that the other details explained in connection with system 200 illustrated in FIG. 2 apply to system 400 illustrated in FIG. 4 and are therefore not repeated.

FIG. 5 is a schematic diagram illustrating an alternative example setup of a system 500 for estimating the thickness of buried concrete 102. As illustrated, sensor $S_2$ 250 can be removably coupled to exposed concrete 104 and a dispersive wave generated by exciting exposed concrete 104 as explained in connection with system 300 of FIG. 3. Also as illustrated, sensor $S_1$ 240 can be placed at different vertical positions by driving casing 210 directly into the Earth 108, for example, by impacting conduit 220 as explained in connection with system 400 of FIG. 4. Thus, the other details and general operation of the system 500 is the same as the other details and general operation of the previous systems and are therefore not repeated.

Figure 13:
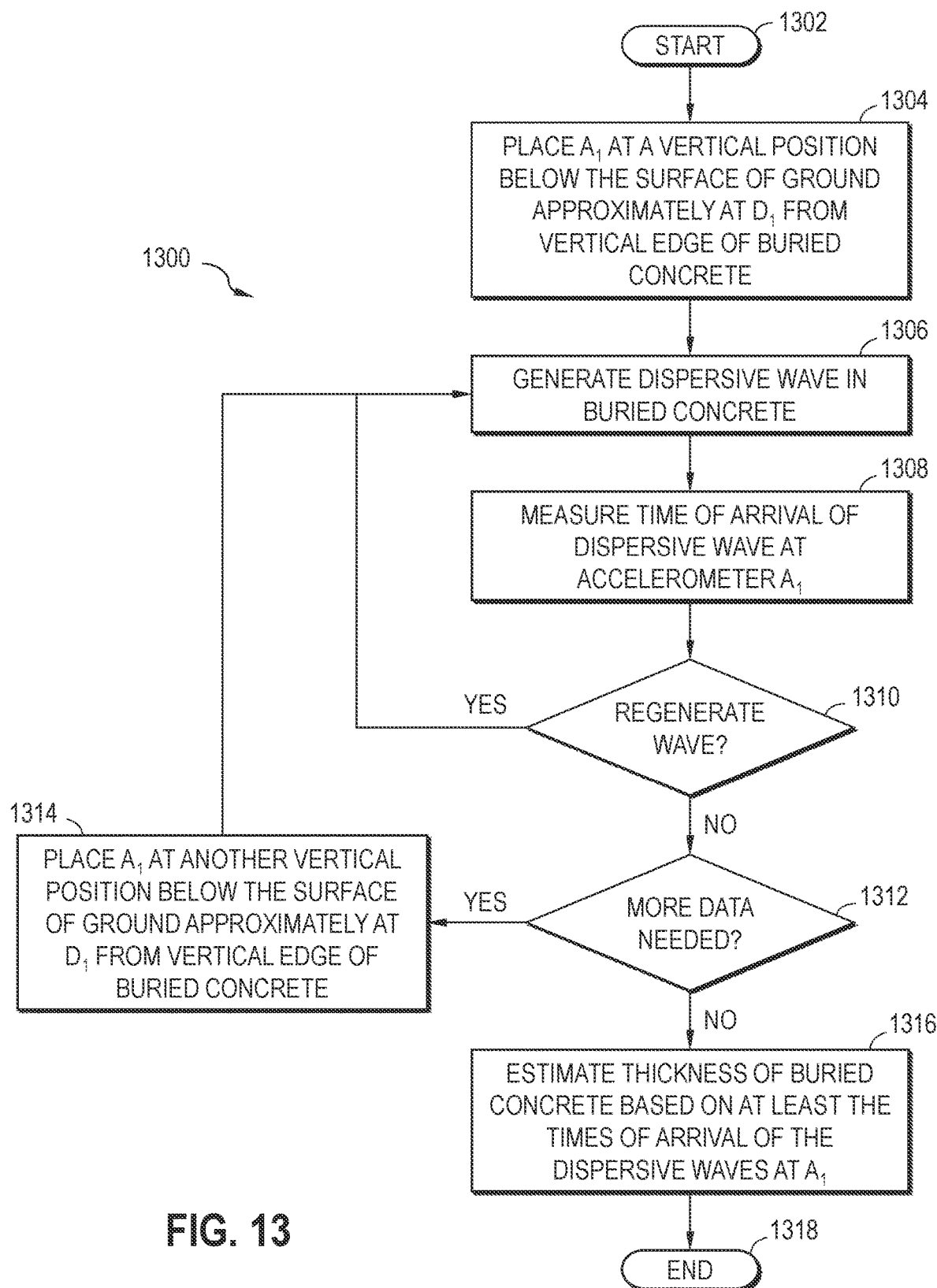
FIG. 13 is a flow diagram illustrating an example method for estimating the thickness of buried concrete.

FIG. 13 is a flow diagram illustrating an example method for estimating the thickness of buried concrete. The method of FIG. 13 will be described with reference to system 200 shown in FIG. 2, but is not so limited. In other examples, additional or alternative systems or components can be used to perform the method of FIG. 13, including, for example, systems 300, 400, or 500. Additionally, for illustration purposes and convenience, sensors $S_1$ and $S_2$ comprise accelerometers $A_1$ 240 and $A_2$ 250 in the example methods provided below. As noted elsewhere in this disclosure, sensors $S_1$ and $S_2$ can be other types of sensors.

Upon starting at step 1302, a first accelerometer $A_1$ 240 is placed at a vertical position below the surface of the ground 106 at step 1304. Accelerometer $A_1$ 240 can be placed approximately at a first distance $D_1$ from a vertical edge of buried concrete 102. At step 1306, a dispersive wave is generated in buried concrete 102. At step 1308, the time of arrival of the dispersive wave at accelerometer $A_1$ 240 is measured. It is possible that, at step 1308, the time of arrival of the dispersive wave cannot accurately be determined. For example, the dispersive wave generated at step 1306 may contain anomalies, for example, due to interference from nearby sources. Other factors can cause difficulty in determining a time of arrival. Therefore, at step 1310, it is determined whether the dispersive wave should be regenerated at the same vertical position for accelerometer $A_1$ 240. If the wave should be regenerated, steps 1306 and 1308 can be repeated.

If the wave does not have to be regenerated, it is determined at step 1312 whether additional data is needed. For example, the accuracy of estimating the thickness of buried concrete 102 may be related to the incremental positions at which accelerometer $A_1$ 240 is placed. Preferably, accelerometer $A_1$ 240 is moved incrementally at distances of one inch and include measurements taken when accelerometer $A_1$ 240 is slightly above the surface of buried concrete 102, slightly below the bottom of buried concrete 102, and in between the top and bottom. Thus, if it determined at step 1312 that additional data is needed, accelerometer $A_1$ 240 can be moved to another vertical position below the surface of the ground at step 1314. Ideally, accelerometer $A_1$ 240 is moved to another vertical position that is approximately at distance $D_1$ from the vertical edge of buried concrete. Steps 1306 through 1312 can then be repeated for the new vertical position. When it is determined at step 1312 that additional data is not needed, at step 1316, the thickness of buried concrete 102 can be estimated based on at least the times of arrival of the dispersive waves at accelerometer $A_1$ 240. The method ends at step 1318.

Figure 14:
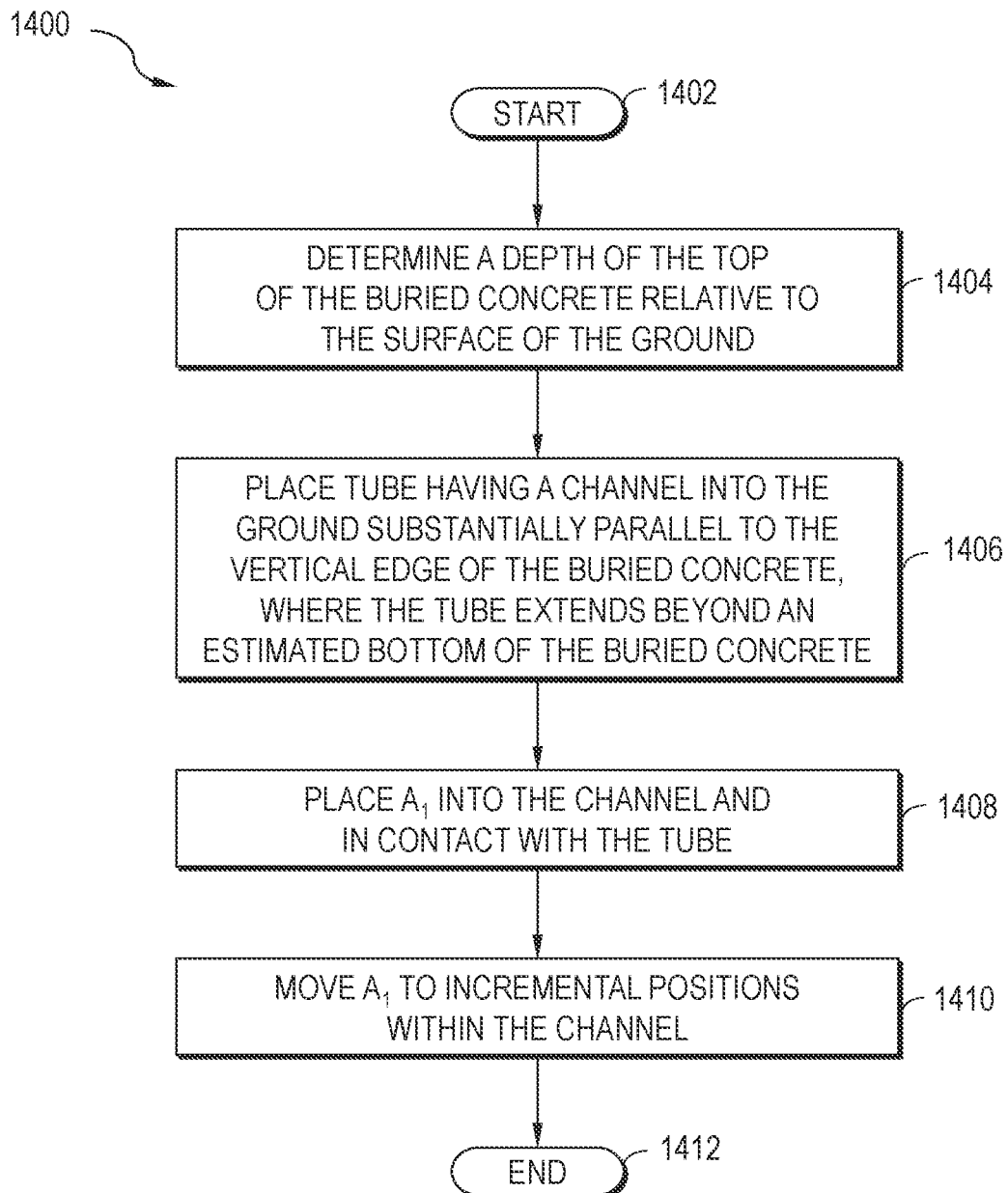
FIG. 14 is a flow diagram illustrating an example method for placing an accelerometer at a plurality of vertical positions below the surface of the ground.

FIG. 14 is a flow diagram illustrating an example method for placing accelerometer $A_1$ 240 at a plurality of vertical positions below the surface of the ground 106. The method of FIG. 14 can be used, for example, in connection with method 1300 of FIG. 13.

Upon starting at step 1402, a depth of the top of the buried concrete 102 can be determined relative to the surface of the ground 106 at step 1404. For example, a rod can be driven into the Earth 108 in the vicinity of where buried concrete 102 is expected to be located. At step 1406, a hollow tube 230 having a channel 232 can be placed substantially parallel to a vertical edge of the buried concrete 102. The hollow tube 230 can be placed such that it extends beyond an estimated bottom of the buried concrete, preferably, approximately 2 feet beyond the estimated bottom. At step 1408, accelerometer $A_1$ 240 can be placed into the channel 232 and in (direct or indirect) contact with hollow tube 230 (e.g., by being placed directly in hollow tube 230 or by being encased in casing 210, which can be in contact with hollow tube 230). At step 1410, accelerometer $A_1$ 240 can be moved to incremental vertical positions within channel 232. The method ends at step 1412.

Figure 15:
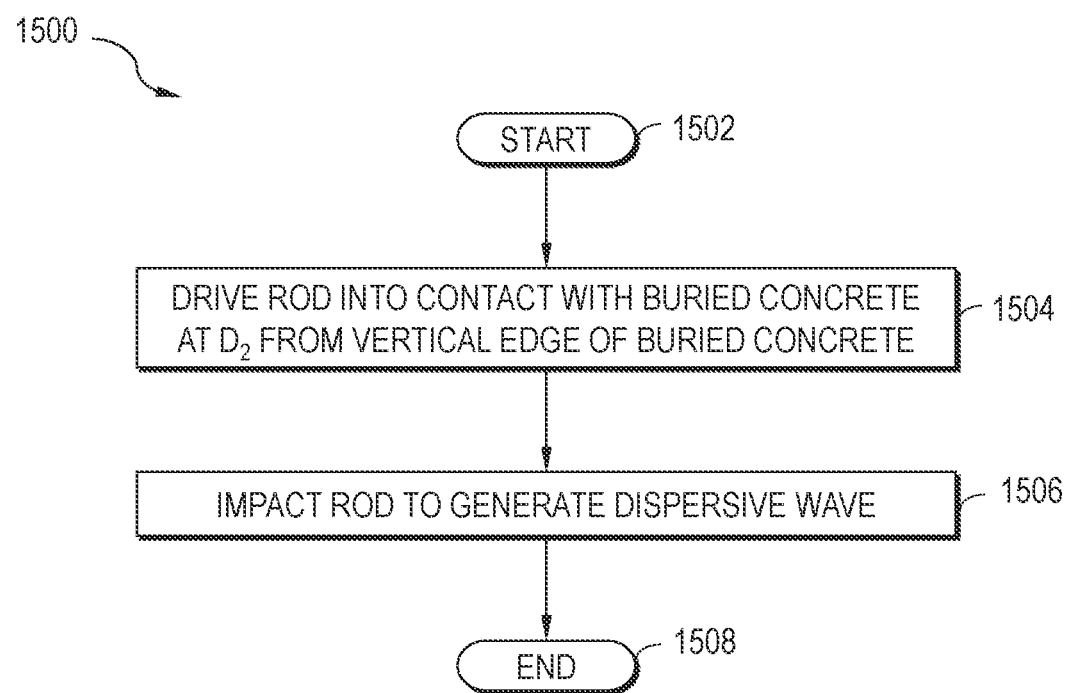
FIG. 15 is a flow diagram illustrating an example method for generating a dispersive wave in buried concrete.

FIG. 15 is a flow diagram illustrating an example method for generating a dispersive wave in the buried concrete 102. The method of FIG. 15 can be used, for example, in connection with method 1300 of FIG. 13.

Upon starting at step 1502, a rod 260 can be placed into contact with the buried concrete 102 at a second distance $D_2$ from a vertical edge of buried concrete 102 (step 1504). Preferably, $D_2$ is within the range of 1.5 to 3 feet. At step 1506, a dispersive wave can be generated by exciting the top of rod 260. This should cause a dispersive wave to travel down rod 260 and to be transmitted to buried concrete 102. The method ends at step 1508.

Figure 16:
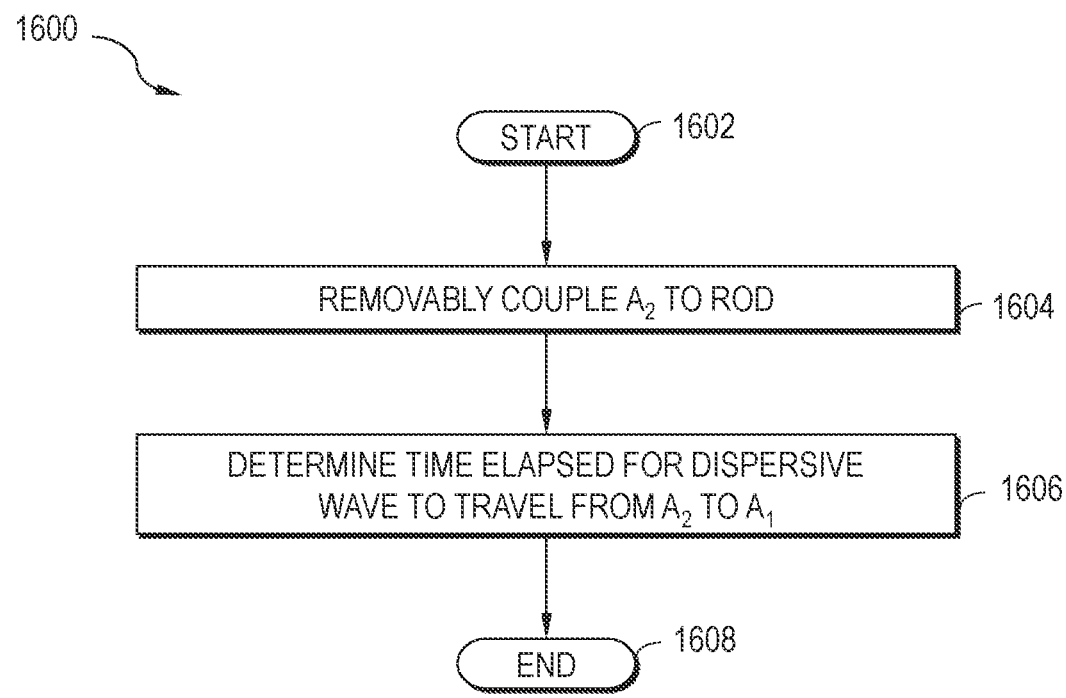
FIG. 16 is a flow diagram illustrating an example method for determining a time of arrival of a dispersive wave at an accelerometer.

FIG. 16 is a flow diagram illustrating an example method for determining a time of arrival of the dispersive wave at accelerometer $A_1$ 240. The method of FIG. 16 can be used, for example, in connection with method 1500 of FIG. 15.

Upon starting at step 1602, a second accelerometer $A_2$ 250 can be removably coupled to rod 260 at step 1604. Accelerometer $A_2$ 250 can be removably coupled to rod 260, for example, with a magnet. Preferably, accelerometer $A_2$ 250 is removably coupled approximately 6 inches from the top of rod 260. However, other distances for removably coupling accelerometer $A_2$ 250 to rod 260 can be used and are contemplated herein. At step 1606, the time elapsed for a dispersive wave to travel from accelerometer $A_2$ 250 to accelerometer $A_1$ 240 can be determined. For example, when the method of FIG. 16 is used in connection with the method of FIG. 15, a dispersive wave can be generated by exciting the top of rod 260. When the dispersive wave reaches accelerometer $A_2$ 250, it can be used as a reference for measuring the time it takes the wave to reach accelerometer $A_1$ 240. For example, the time of arrival at accelerometer $A_2$ 250 can be considered time $T_0$ and the time of arrival at accelerometer $A_1$ 240 can be considered time $T_1$. Thus, the elapsed time from accelerometer $A_2$ 250 to accelerometer $A_1$ 240 can be determined by subtracting $T_1$ from $T_0$. The method ends at step 1608.

Figure 17:
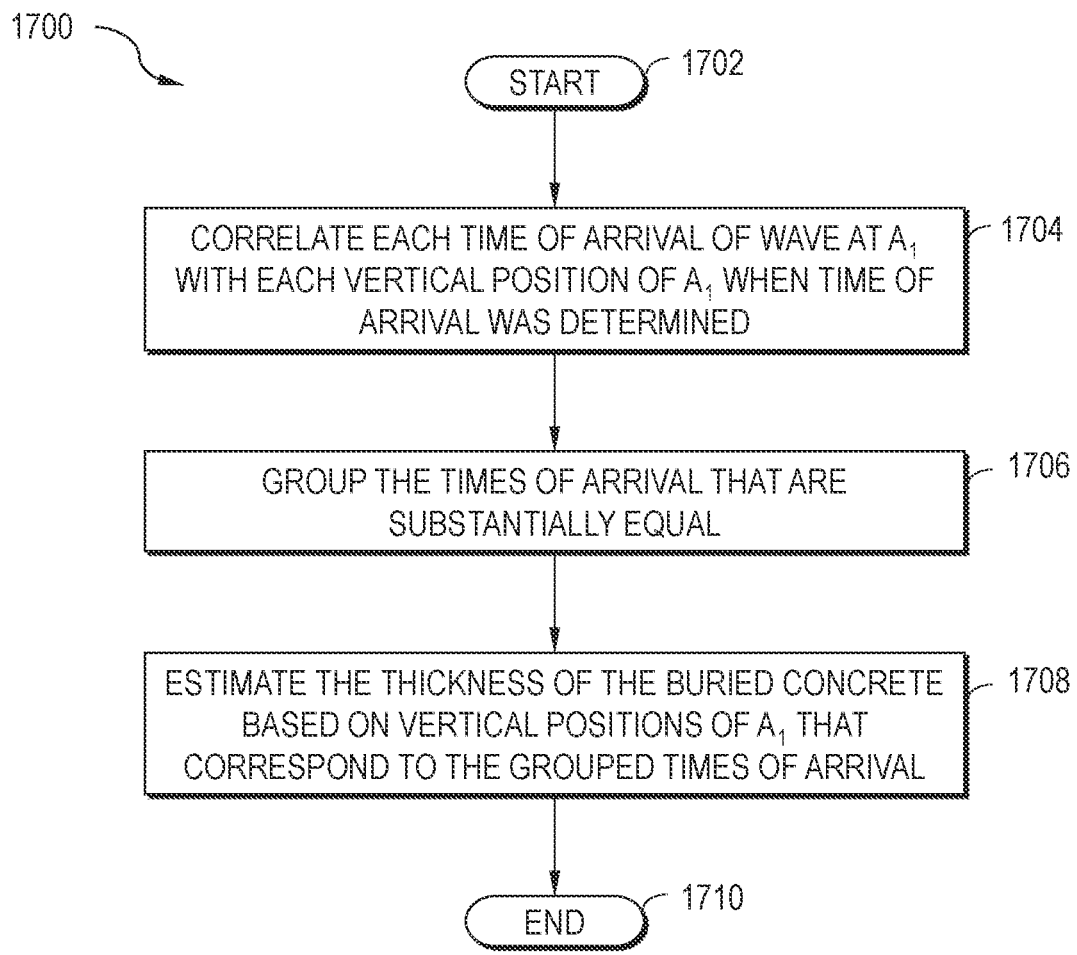
FIG. 17 is a flow diagram illustrating an example method for estimating the thickness of buried concrete based on at least times of arrival of dispersive waves at an accelerometer.

FIG. 17 is a flow diagram illustrating an example method for estimating the thickness of buried concrete 102. The method of FIG. 17 can be used, for example, in connection with method 1300 of FIG. 13.

Upon starting at step 1702, each time of arrival of the dispersive wave at accelerometer $A_1$ 240 can be correlated with each vertical position of accelerometer $A_1$ 240 when the time of arrival was determined (step 1704). This can be achieved, for example, using a graph similar to the graphs illustrated in FIGS. 9A and 9B. At step 1706, the times of arrival that are substantially equal can be grouped as explained above in connection with FIG. 9B. At step 1708, the thickness of buried concrete 102 can be estimated based on vertical positions of accelerometer $A_1$ 240 that correspond to the times grouped in step 1706. The method ends at step 1710.

Figure 18:
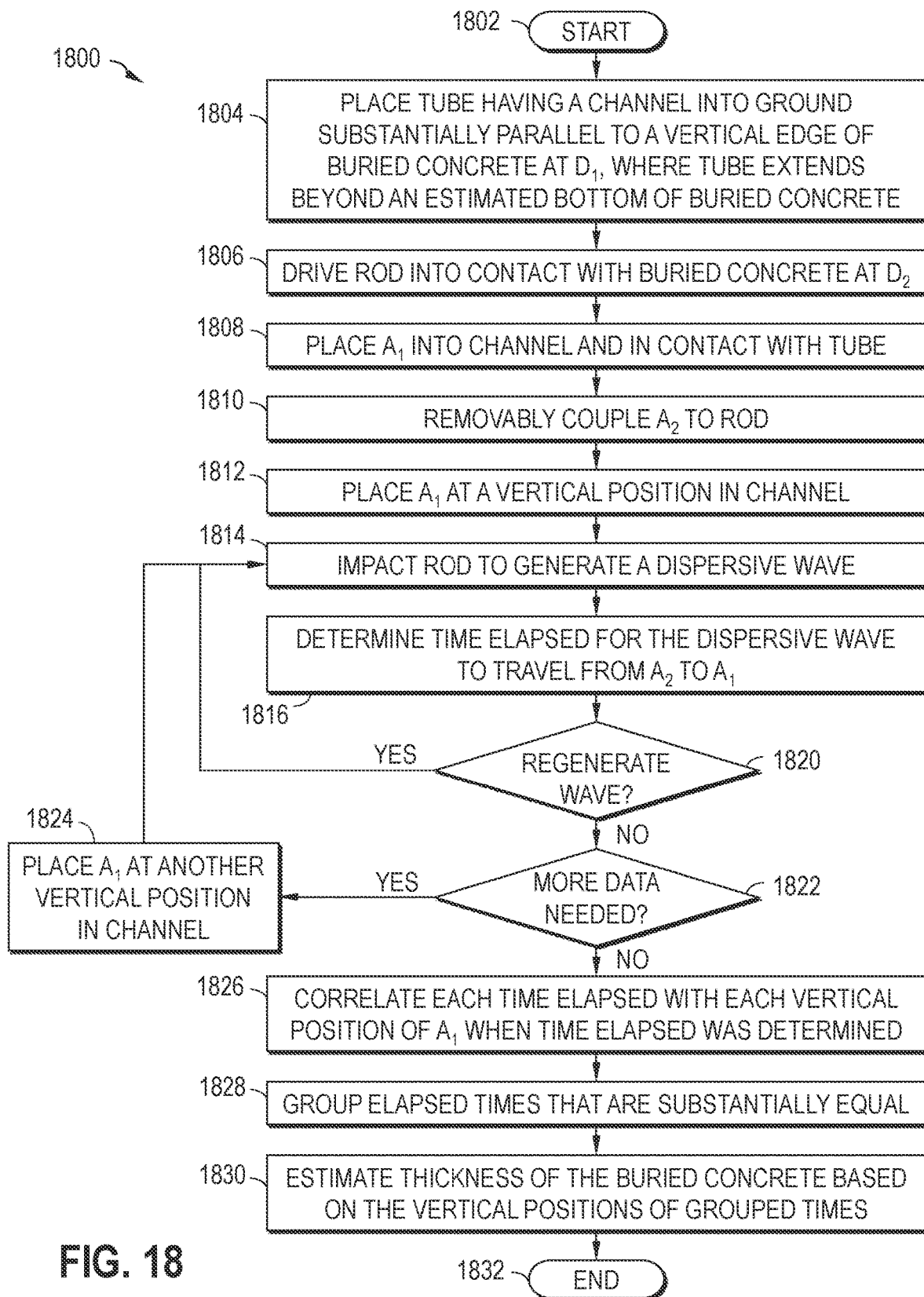
FIG. 18 is a flow diagram illustrating an example method for estimating the thickness of buried concrete.

FIG. 18 is a flow diagram illustrating an example method for estimating the thickness of buried concrete. The method of FIG. 18 will be described with reference to system 200 shown in FIG. 2, but is not so limited. In other examples, additional or alternative systems or components can be used to perform the method of FIG. 18.

Upon starting at step 1802, a hollow tube 230 having a channel 232 can be placed into the ground substantially parallel to a vertical edge of the buried concrete 102 at a distance $D_1$ from the vertical edge (step 1804). The hollow tube 230 can be placed such that it extends beyond an estimated bottom of the buried concrete, preferably, approximately 2 feet beyond the estimated bottom. At step 1806, a rod 260 can be driven through the Earth 108 and into contact with buried concrete 102 at a distance $D_2$. Preferably, distance $D_2$ is within the range of 1.5 to 3 feet. At step 1808, a first accelerometer $A_1$ 240 can be placed into the channel 232 and in (direct or indirect) contact with hollow tube 230 (e.g., by being placed directly in hollow tube 230 or by being encased in casing 210, which can be in contact with hollow tube 230). At step 1810, a second accelerometer $A_2$ 250 can be removably coupled to rod 260. Accelerometer $A_2$ 250 can be removably coupled to rod 260, for example, with a magnet. Preferably, accelerometer $A_2$ 250 is removably coupled approximately 6 inches from the top of rod 260. However, other distances for removably coupling accelerometer $A_2$ 250 to rod 260 can be used and are contemplated herein.

At step 1812, accelerometer $A_1$ 240 can be placed at a first vertical position within channel 232. At step 1814, a dispersive wave can be generated by exciting rod 260. At step 1816, the time elapsed for a dispersive wave to travel from accelerometer $A_2$ 250 to accelerometer $A_1$ 240 can be determined. For example, when the dispersive wave is generated by impacting the top of rod 260 in step 1814, the dispersive wave should travel down rod 260 and trigger accelerometer $A_2$ 250, which can be used as a reference for measuring the time it takes the wave to reach accelerometer $A_1$ 240. For example, the time of arrival at accelerometer $A_2$ 250 can be considered time $T_0$ and the time of arrival at accelerometer $A_1$ 240 can be considered time $T_1$. Thus, the elapsed time from accelerometer $A_2$ 250 to accelerometer $A_1$ 240 can be determined by subtracting $T_1$ from $T_0$.

It is possible that, at step 1816, the time of arrival of the dispersive wave cannot be accurately determined. For example, the dispersive wave generated at step 1814 may contain anomalies, for example, due to interference from nearby sources. Other factors can cause difficulty in determining a time of arrival. Therefore, at step 1820, it is determined whether the dispersive wave should be regenerated at the same vertical position for accelerometer $A_1$ 240. If the wave should be regenerated, steps 1814 and 1816 can be repeated.

If the wave does not have to be regenerated, it is determined at step 1822 whether additional data is needed as explained above in connection with step 1312 of FIG. 13. If additional data is needed, accelerometer $A_1$ 240 can be moved to another vertical position below the surface of the ground 106 at step 1824. Steps 1814 through 1822 can then be repeated for the new vertical position.

When it is determined at step 1822 that additional data is not needed, at step 1826, the time elapsed for the dispersive wave to travel from accelerometer $A_2$ 250 to accelerometer $A_1$ 240 can be correlated with each vertical position of accelerometer $A_1$ 240 when the elapsed times were determined. At step 1828, the elapsed times that are substantially equal can be grouped. At step 1830, the thickness of buried concrete 102 can be estimated based on vertical positions of accelerometer $A_1$ 240 that correspond to the elapsed times that were grouped in step 1828. The method ends at step 1832.

Figure 19:
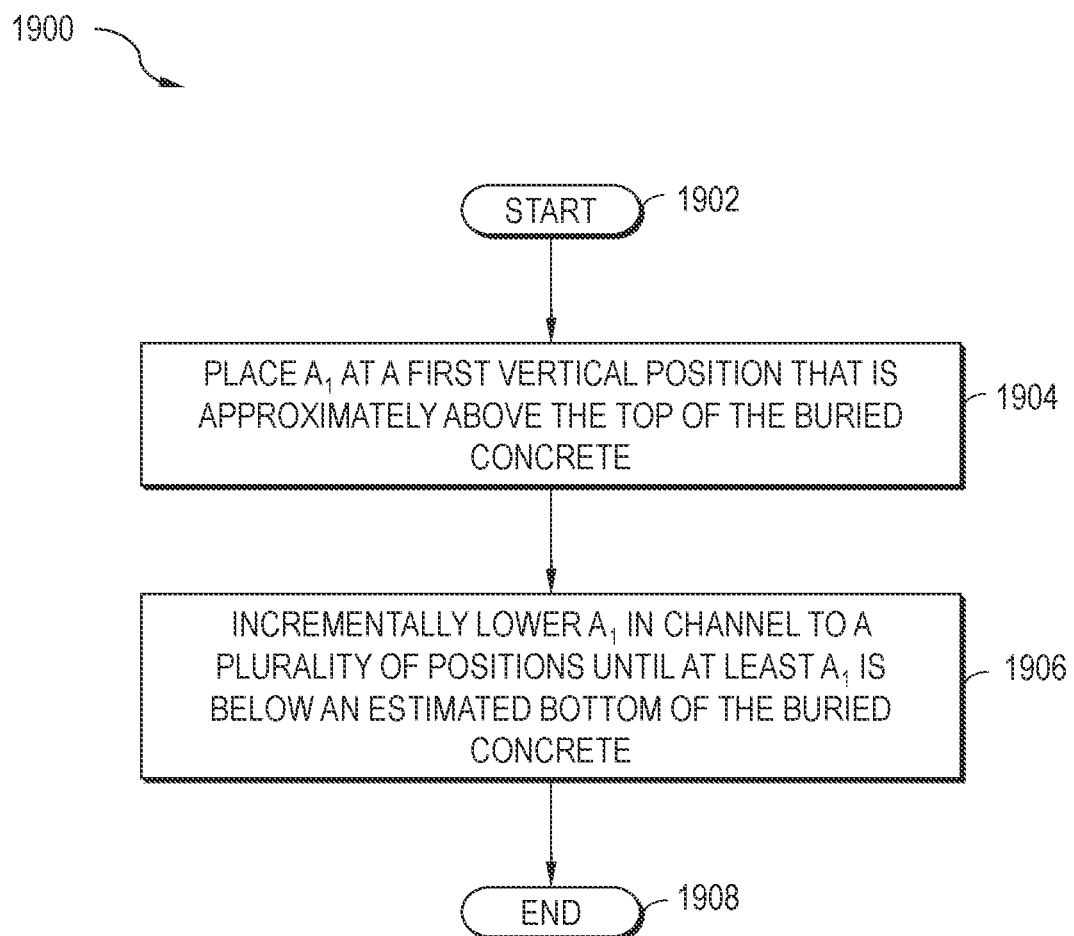
FIG. 19 is a flow diagram illustrating an example method for placing an accelerometer at a plurality of vertical positions.

FIG. 19 is a flow diagram illustrating an example method for placing the first accelerometer $A_1$ 240 at a plurality of vertical positions within channel 232. The method of FIG. 19 can be used, for example, in connection with method 1800 of FIG. 18.

Upon starting at step 1902, accelerometer $A_1$ 240 can be placed at a first vertical position within channel 232 that is approximately above the top of the buried concrete 102 (step 1904). At step 1906, accelerometer $A_1$ 240 can be incrementally lowered in channel 232 to a plurality of positions until accelerometer $A_1$ 240 is below an estimated bottom of the buried concrete. For example, accelerometer $A_1$ 240 can be lowered in channel 232 in increments of one inch. The method ends at step 1908.

Although the inventive methods, including the methods of FIGS. 13-19, are described in terms of vertically displacing a first sensor $S_1$ 240 (in the examples, an accelerometer), as previously explained, the inventive methods are not limited to using one sensor, but rather can employ one or more first sensors. For example, the inventive methods can use two first accelerometers bundled together. As another example, the inventive methods can use four velocity sensors bundled together. As yet another example, the inventive methods can use 3 accelerometers and 3 displacement sensors bundled together.

FIGS. 20-24 illustrate graph diagrams of example plots for alternative or additional systems and methods of estimating the thickness of buried concrete 102. In each example, sensors $S_1$ and $S_2$ comprise accelerometers $A_1$ 240 and $A_2$ 250 for convenience and ease of explanation. As explained elsewhere in this disclosure, sensors $S_1$ and $S_2$ can be other types of sensors. The figures plot time on the horizontal axis (microseconds) and the vertical position of accelerometer $A_1$ 240 on the vertical axis (in inches). In the example graph of FIGS. 20-24, the arrival times of the dispersive waves at accelerometer $A_2$ 250 (when accelerometer $A_2$ 250 is triggered at time $T_0$) are represented by time=0 for each waveform. The approximate arrival times of the dispersive waves at accelerometer $A_1$ 240 (when accelerometer $A_1$ 240 is triggered at time $T_1$) are represented graphically as the point at which each waveform transitions from an approximate steady state to a non-zero amplitude. In this example, 29 measurements were made (illustrated by the 29 waveforms) beginning with accelerometer $A_1$ 240 placed at −36 inches, which represents the approximate depth of accelerometer $A_1$ 240 below the surface of the ground 106. That depth may have been chosen, for example, by first determining the approximate depth of the surface of the buried concrete, then placing accelerometer $A_1$ 240 a short distance above that depth. Each of the subsequent measurements were made by incrementally lowering accelerometer $A_1$ 240 by approximately 2 inches. Thus, initial values for each signal are $T_0$ (all of which are time=0) and values for $T_1$ each correspond to a different vertical position for accelerometer $A_1$ 240. Based on the data sets, a depth-time plot is generated.

In disclosed examples, systems and methods are provided which include a post-processing routine employing software and/or hardware to immediately determine whether the data collected with the dry PS systems and methods is conclusive or inconclusive without the need for an operator to analyze signals and/or to validate data collection. For example, the systems and methods receive signals from an impact to the concrete. In some examples, the sensor(s) may detect the waves at one or more depths relative to the surface of the ground and/or the buried concrete portion. For instance, the sensor(s) can be moved (e.g., incrementally, continuously, to predetermined depths, etc.) between detection events.

Figure 20:
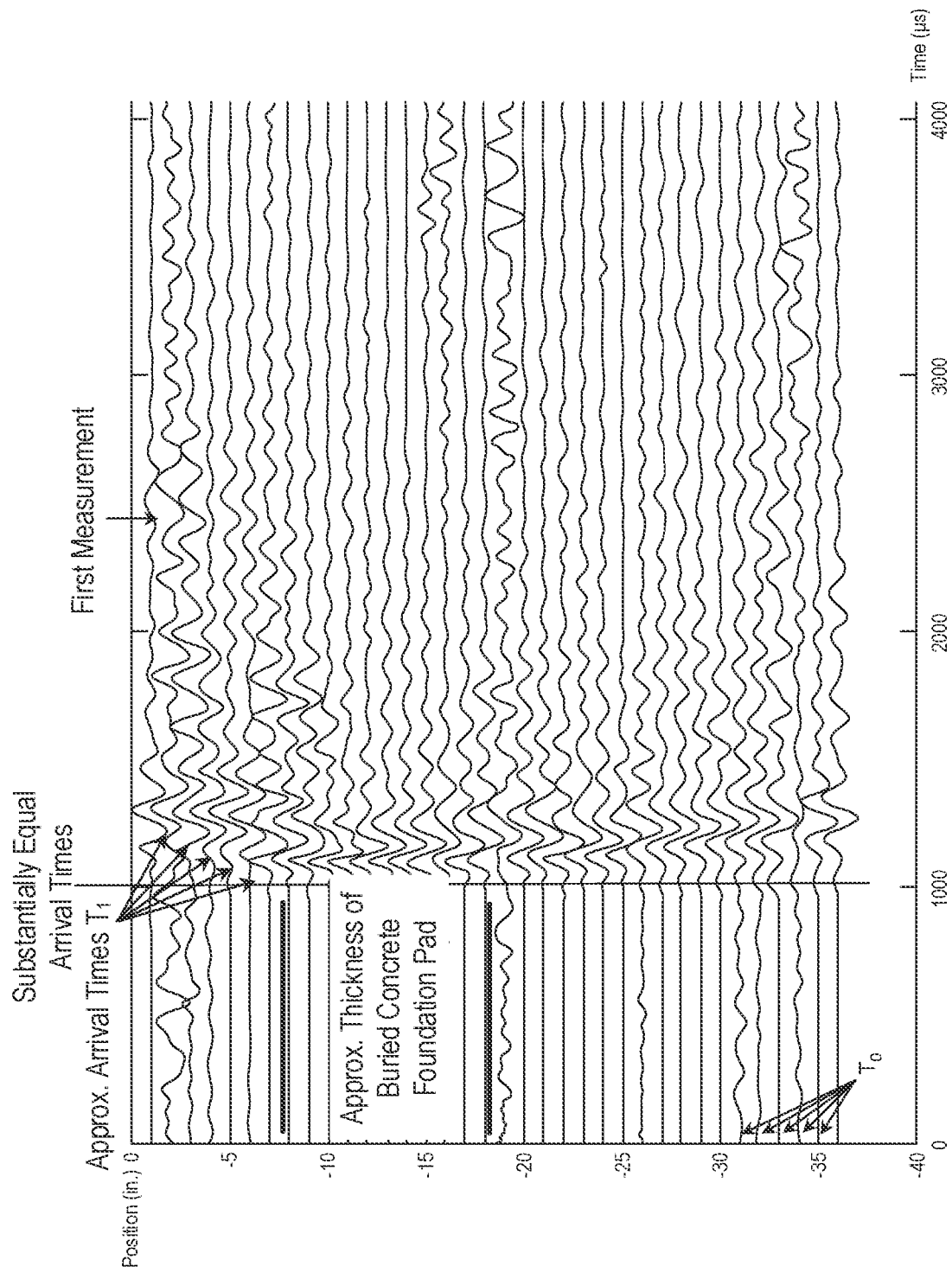
Figure 23:
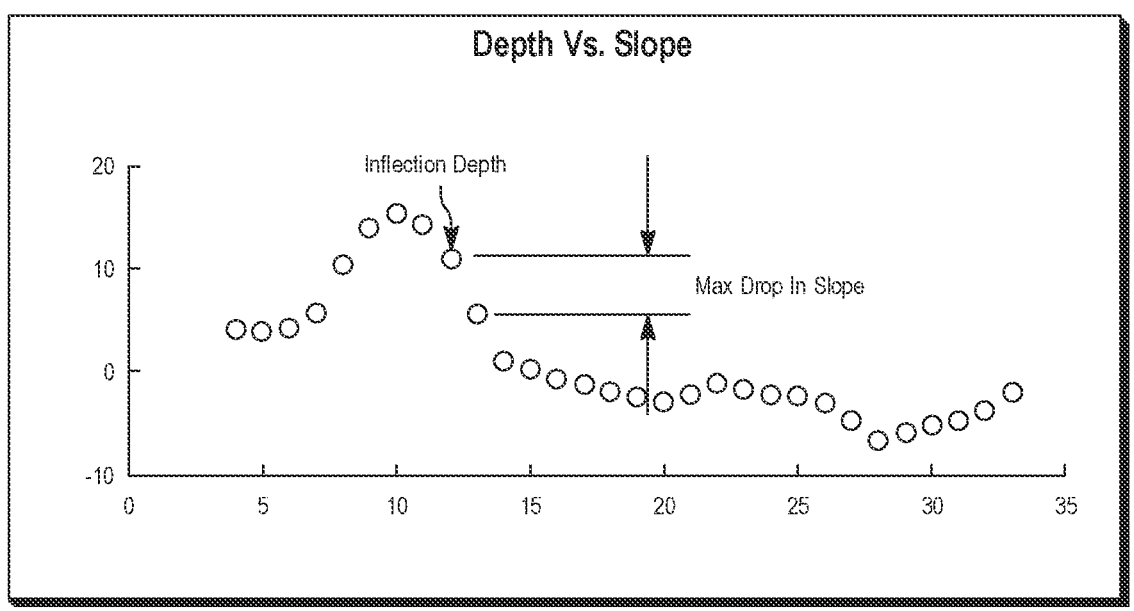

Thus, data based on the signals generated by the sensor in response to detection of the waves can then be plotted to generate a depth vs. time plot, as shown in FIG. 20. The signals are analyzed to provide data used to identify an inflection point at which the arrival time of the waves (e.g., based on the data sets) starts to shift (e.g., beyond a threshold level). Having generated the depth vs. time plot, the receiver 270 (or external system 290) can perform an analysis to identify an inflection point at which the arrival time of the waves starts to shift beyond a threshold level, as shown in FIG. 23.

Figure 22:
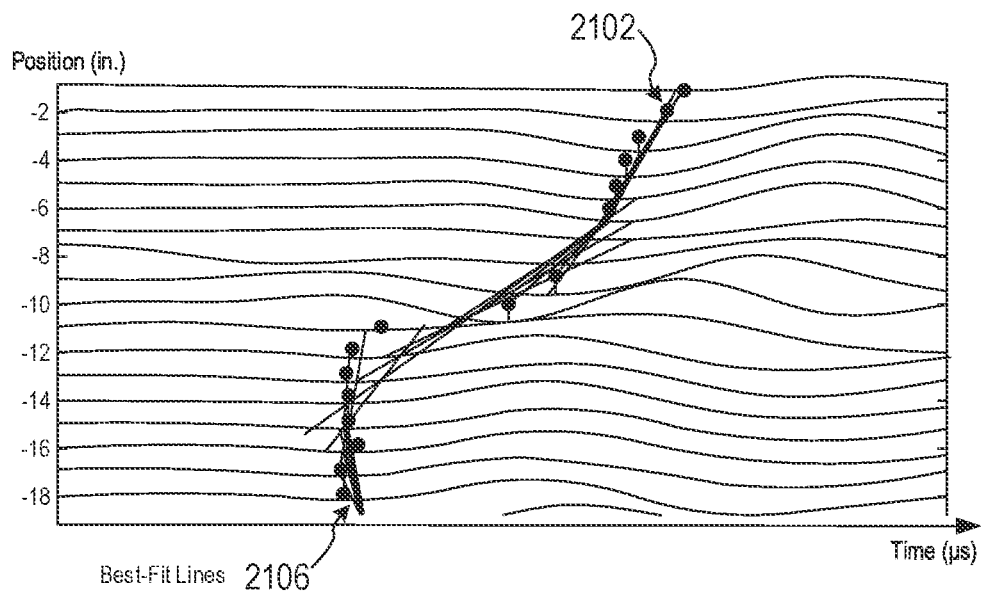
Figure 24A:
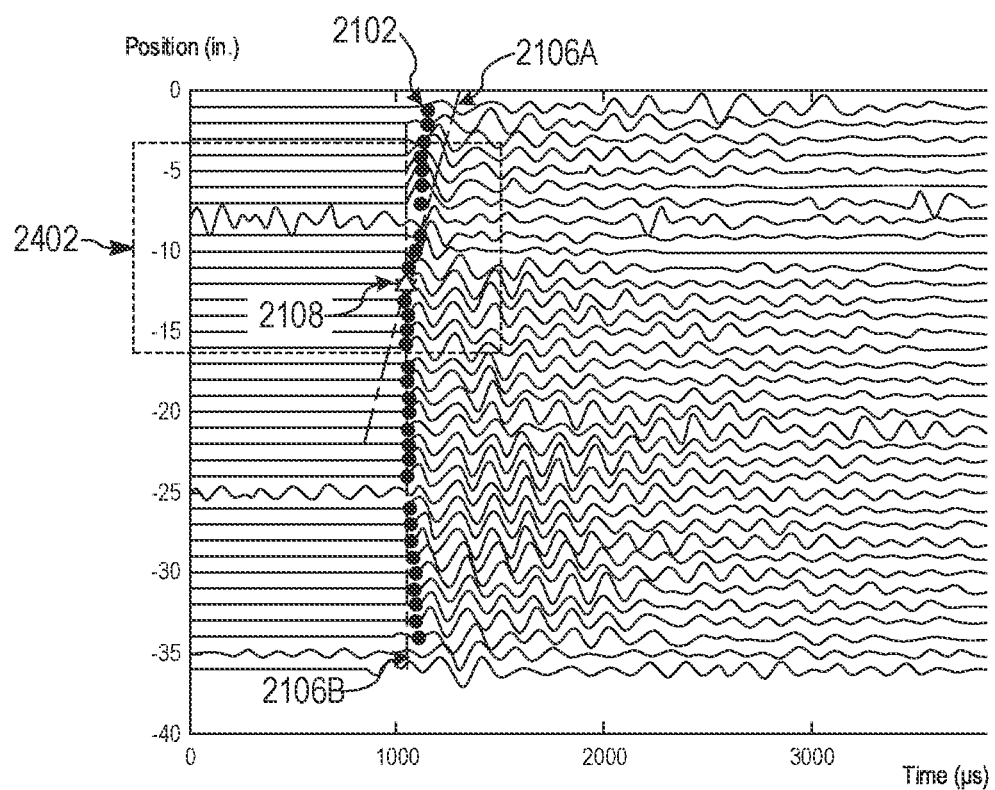
Figure 24B:
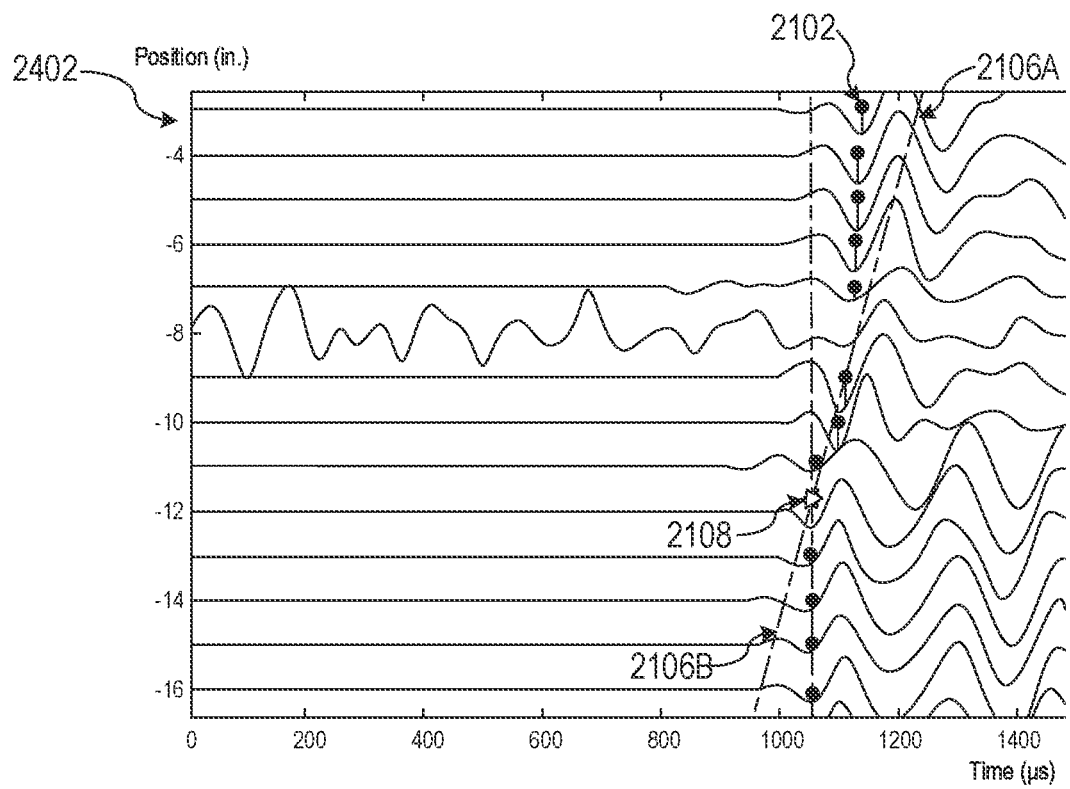

From the inflection point, two or more best fit lines are drawn above and/or below the inflection point along the depth vs. time graph of wave arrival times, as shown in FIG. 22. For example, two or more best fit lines are drawn above and/or below the inflection point along a graph of wave arrival times. An intersection point between two or more of the best fit lines is used to calculate or estimate a depth of the bottom of the buried concrete portion, as shown in FIGS. 24A and 24B. With calculated or estimated depths of the top and bottom of the buried concrete portion, the thickness of the buried concrete pad can be calculated. In some examples, the receiver 270 (or external system 290) additionally or alternatively calculates the value represented by the intersection point without plotting the values of depth and time in a graph.

In disclosed examples, the systems and methods employ one or more quality checks to the signal and/or data sets to ensure the information received from sensors $S_1$ 240 and $S_2$ 250 will provide conclusive results. For instance, an individual check function is performed on each signal (e.g., as the wave is detected and/or when the data is transmitted to the receiver 270 (or external system 290)) to determine signal quality. One or more characteristics of the signal can be compared against one or more signal quality threshold values and, if the characteristics satisfy the one or more thresholds, the receiver 270 (or external system 290) determines the signal quality is sufficient to generate a conclusive result about the thickness of the buried concrete structure.

Figure 21A:
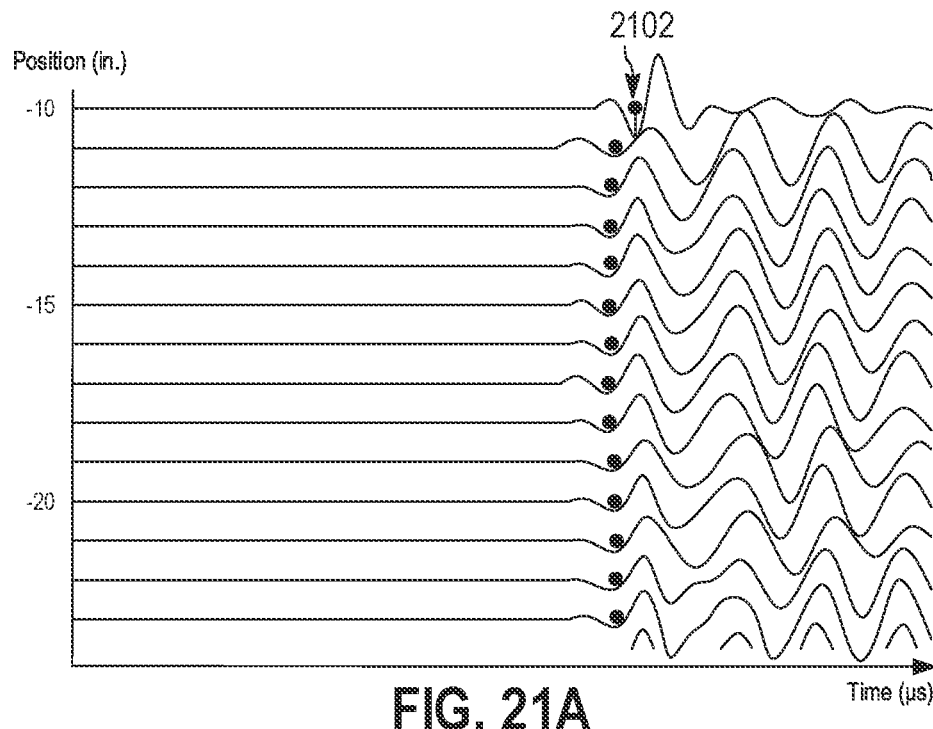
Figure 21B:
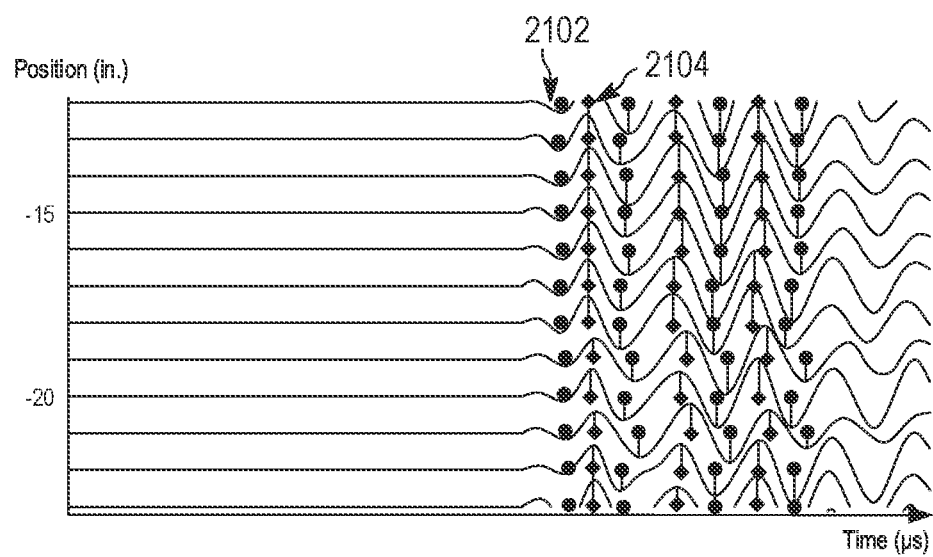

As shown in FIGS. 21A and 21B, the arrival time of the wave at each depth (e.g., a detection event) can be defined by a time stamp of a negative peak 2102 immediately preceding a first positive peak 2104 that exceeds a threshold prominence (e.g., an amplitude, slope, absolute value, etc.). These times stamps are used in calculating, determining, or otherwise estimating an inflection point and/or the best-fit lines.

In some examples, a single time stamp is used to determine arrival time, whereas in other examples multiple time stamps are identified during a detection event. For instance, multiple time stamps may come from positive peaks, negative peaks, or a combination of both.

As shown in FIG. 23, analysis of the data sets and/or the arrival times identifies an inflection depth, which is a depth at which the arrival times increase most rapidly with depth. This depth corresponds to the calculated, determined, estimated and/or plotted inflection point in the data, which is used to calculate or estimate the depth of the buried concrete portion.

The inflection depth can be identified through analysis of one or more groupings of signals. For example, one or more groups of signals collected over a number of sampling events during a depth measurement operation are identified, starting from signals detected at a shallow depth (e.g., least negative), to signals detected at a greater depth. Multiple signals may be detected between the two, as the sensor is moved within the channel (e.g., at predetermined increments). In some examples, a first group may contain a first number of signals, and a second group may contain a second number of signals, which may or may not overlap. In some examples, the first group would include signals from a first depth (e.g., corresponding to a top surface of the pad foundation) to a second depth (e.g., a predetermined depth below the top surface). The second group of signals would include signals from a third depth between the first and second depths to a fourth depth greater than the second depth. A third group of signals would include signals from a fifth depth between the third and fourth depths to a sixth depth greater than the fourth depth, and so on.

In an example, the number of signals in each group does not vary throughout data collection. In some examples, the number of signals in each group can be 2, 3, 4, 5, 6, 7, 8, 9, 10, 15, 20, 30 or more, less, or any intermediate number of signals. In some examples, the number of signals in each group can vary. In some examples, seven signals per group may be used. For example, in a data set with 36 signals, the first group of signals (e.g., at the shallowest depth) includes signals from a depth between 1-7 units (e.g., inches, centimeters, meters, etc.), the second group includes signals from depths between 2-8 units, the third group includes signals from depths between 3-9 units, and so on, until the last group includes signals between depths 30-36. For each group of signals a corresponding slope is calculated based on the arrival times of the dispersive waves, as disclosed herein.

Once the signals are grouped and/or analyzed, a best-fit line 2106 can be calculated for the wave-arrival time stamps for each of the groups of signals, as shown in FIG. 22. Analysis of the line slope identifies a drop, which corresponds to an increase in depth. As the wave arrival times increase with depth, a drop of the slope beyond a threshold amount indicates that the sensor has reached a depth below the bottom of the buried concrete portion. Therefore, the location of the greatest decrease in the slope(s) of the lines is identified as corresponding to the inflection depth or point, as shown in FIG. 23. In some examples, identification of a first drop in the slope beyond a threshold amount may be used to identify the inflection point in addition to or in the alternative of identification of a maximum drop in the slope. In some examples, the depth at which the maximum error or residual of each line occurs is used to identify the inflection point.

In an example employing multiple time stamps for each signal, two or more methods or techniques may be used to calculate an inflection depth. For instance, an algorithm may be used to fit best-fit lines to all possible combinations of time stamps within the group, using just one time stamp from each signal. The best-fit line with the lowest residual would be chosen as the line to use for each group. In some examples, all time stamps, their associated amplitudes, and the known depth of the buried concrete portion may be used in a training dataset for a machine-learning model that will predict buried concrete portion thickness.

Once the inflection depth is determined, first best-fit line 2106A and second best-fit lines 2106B—one above and one below the inflection point—are calculated, estimated, or otherwise determined for a predetermined number of points above and below the inflection depth, as shown in FIGS. 24A and 24B. One or more of the best-fit lines may include the inflection-depth point, or may start some number of points above and/or below the inflection-depth point.

FIG. 24B illustrates a detail view 2402 of FIG. 24A. Within view 2402, an intersection point 2108 of the first and second best-fit lines is calculated, and the depth-coordinate of this intersection is determined as the depth of the bottom of the buried concrete portion. In this example, the first signal was recorded with the sensor at a depth equal to the top surface of the buried concrete portion. Thus, the depth corresponding to the intersection point 2108 is the buried concrete portion thickness.

In some examples, one or more sensors (e.g., the first sensor $S_1$) can monitor for dispersive waves at a variety of depths. For instance, an inflection depth can be determined for a top surface of the buried concrete based on arrival times of dispersive waves. First and second best-fit lines can be determined, and the intersection point calculated or estimated, the value of the intersection point corresponding to a value of the depth of the top surface of the buried concrete. Therefore, the top surface of the buried concrete may be determined in a manner similar to the disclosed examples of determining a depth corresponding to the bottom surface of the buried concrete, in addition to or in the alternative of determining the depth of the top surface physically.

Accordingly, the thickness of buried concrete can be determined in different ways. For example, the depth of the top surface of the buried concrete may be determined physically (e.g., by driving a rod to the top surface and measuring the distance driven), the depth of the bottom surface determined by identifying an inflection depth and the intersection of two best-fit lines, and the thickness of the buried concrete calculated as the distance from the measured depth of the top surface to the intersection of the best-fit lines. As another example, the depth of the top surface of the buried concrete can be determined by identifying a top surface inflection depth and a top surface intersection of two best-fit lines, the depth of the bottom surface determined by identifying a bottom surface inflection depth and a bottom surface intersection of two best-fit lines, and the thickness of the buried concrete calculated as the distance from the top surface intersection to the bottom surface intersection. Further, it will be appreciated that a rough estimate of the thickness of the buried concrete can be determined as the distance between the top surface inflection depth and the bottom surface inflection depth (or the measured depth of the top surface to the bottom surface inflection depth).

In some examples, one or more concrete pads may be arranged below ground, such as a series of layers forming the foundation and/or surrounding features (e.g., bedrock, soil, structural features of the building, etc.).

In some examples, one or more layers of the buried foundation may be constructed of the same material. In some examples, one or more layers of the buried foundation are constructed of different materials, which may be identified separately based on different arrival times, wave characteristics, etc. Accordingly, the disclosed systems may be configured to identify an interface between layers, and therefore identify depths of the interfaces and/or individual layers.

In some disclosed examples, the systems and methods incorporate one or more filtering and/or checks to ensure the collected signals and/or data will yield a conclusive depth measurement. Some of the filtering and/or checks can be performed on individual signals collected from the sensors. Other filtering and/or checks can be performed on the overall signals and/or data collected.

For instance, a pre-trigger noise check function can check each signal in the overall analysis for large amplitudes in the first 600 pings of the signal. A different number of pings may also be used and are contemplated herein. The overall pre-trigger noise check function can include applying a Short Kernel Method (SKM) filter to the raw signals before checking for fluctuations. Also, if the pre-trigger noise exceeds a maximum allowable threshold, the signal is kept but the wave arrival time(s) of that signal is not used in the overall analysis. This check function is mainly for use on legacy data that has noisier signals and may be used a backup check on future data where individual check functions may eliminate this problem.

A depth determination is considered valid once the overall analysis is determined to be conclusive. One or more criteria are applied to the data and/or analysis to determine conclusiveness. A non-limiting list of possible inconclusive events include a high number of missing wave-arrival point; lack of a clear inflection point; a low number of points to generate best-fit lines; plotted points fail to generate a qualifying best-fit line; lack of a clear difference in slope between best-fit lines; or a system failure, as shown in FIG. 27.

Although rare, if a crash occurs in the software or hardware associated with the depth measurement, the results may be rendered inconclusive. A crash may include acquisition of poor signal quality and/or data sets, which would also be considered unacceptable.

As explained elsewhere in this disclosure, sensors $S_1$ 240 and $S_2$ 250 are used to collect impact signals, and are operably connected to receiver 270. The receiver 270 may be connected to or incorporated within an external system 290 (e.g., a remote computer, a portable or hand-held device such as a tablet or smartphone, etc.) via a communications channel (e.g., wireless transmission, wired connection, universal serial bus (USB), etc.) and receives the impact signals traveling from the buried concrete portion. The data collection, transmission, and/or analysis process is controlled by one or more software instructions and/or algorithms, and in some examples, a dry PS post-processing routine is included.

For instance, the post-processing routine can include two or more parts, such as the individual signal checks and an overall signal analysis.

The individual signal checks make sure that each signal is of sufficient quality or fidelity to be analyzed via the overall signal analysis. In some examples, the results from the individual signal checks are provided or otherwise presented to an operator as data is collected. For example, a display or alert can be presented to the operator with receiver 270 to indicate that the signal has failed to satisfy one or more thresholds, and indicate another sampling event and/or detection event is required to proceed with analysis.

In some examples, the overall signal analysis takes some or all signals from the entire data set into account. As a result, data and/or signal validation via a manual call-off process may not require a signal analyst (e.g., a human reviewer or administrator). The overall signal analysis determines whether the data set is conclusive or not. If the data is determined to be conclusive, the systems and methods disclosed herein proceeds to calculate or estimate the depth at the bottom of the buried concrete portion. If the data is determined to be inconclusive, however, the operator may be required to perform a new sampling event and collect new data sets.

FIG. 25 is a flow diagram illustrating an example method for estimating the thickness of a buried concrete portion (e.g., foundation pad). The method of FIG. 25 will be described with reference to system 200 shown in FIG. 2, but is not so limited. In other examples, additional or alternative systems or components can be used to perform the method of FIG. 25. Additionally, for illustration purposes and convenience, sensors $S_1$ and $S_2$ comprise accelerometers $A_1$ 240 and $A_2$ 250 in the example methods provided below. As noted elsewhere in this disclosure, sensors $S_1$ and $S_2$ can be other types of sensors.

Upon starting at step 2502, a hollow tube 230 having a channel 232 can be placed into the ground substantially parallel to a vertical edge of the buried concrete 102 at a distance $D_1$ from the vertical edge (step 2504). The hollow tube 230 can be placed such that it extends beyond an estimated bottom of the buried concrete pad (e.g., approximately 2 feet beyond the estimated bottom). At step 2506, a rod 260 can be driven through the Earth 108 and into contact with buried concrete pad 102 at a distance $D_2$. In some examples, distance $D_2$ is within the range of 1.5 to 3 feet, although other ranges can be used depending on the application. At step 2508, a first accelerometer $A_1$ 240 can be placed into the channel 232 and in (direct or indirect) contact with hollow tube 230 (e.g., by being placed directly in hollow tube 230, or by being encased in casing 210, which can be in contact with hollow tube 230). In additional or alternative examples, a second accelerometer $A_2$ 250 can be removably coupled to rod 260. Accelerometer $A_2$ 250 can be removably coupled to rod 260, for example, with a magnet or other fastener. In some examples, accelerometer $A_2$ 250 is removably coupled approximately 6 inches from the top of rod 260. However, other distances for removably coupling accelerometer $A_2$ 250 to rod 260 can be used and are contemplated herein.

At step 2510, accelerometer $A_1$ 240 can be placed at a first vertical position within channel 232. At step 2512, a dispersive wave can be generated by impacting rod 260. At step 2514, the time elapsed for a dispersive wave to travel from the approximately horizontal distance $D_1$ from the concrete pad to accelerometer $A_1$ 240 can be determined. For example, when the dispersive wave is generated by impacting the top of rod 260 in step 2512, the dispersive wave should travel down rod 260 and trigger accelerometer $A_2$ 250, which can be used as a reference for measuring the time it takes the wave to reach accelerometer $A_1$ 240. For example, the time of arrival at accelerometer $A_2$ 250 can be considered time $T_0$ and the time of arrival at accelerometer $A_1$ 240 can be considered time $T_1$. Thus, the elapsed time from accelerometer $A_2$ 250 to accelerometer $A_1$ 240 can be determined by subtracting $T_1$ from $T_0$.

At step 2516, one or more filters and/or function checks may be applied to the signals and/or data sets to determine whether the signals and/or data sets are of sufficient quality to calculate or estimate a conclusive depth measurement. For instance, it is possible that, at step 2516, the time of arrival of the dispersive wave cannot be accurately determined. For example, the dispersive wave generated at step 2514 may contain anomalies, for example, due to interference from nearby sources. Other factors can cause difficulty in determining a time of arrival. The process of filtering and/or determining the quality of a received signal and/or data set is described in greater detail in FIG. 26.

If the data does not satisfy the applied criteria or meet the required data quality thresholds, the method can return to step 2512 to repeat the impact and again detect the signals and/or data from the impact. Therefore, at step 2518, it is determined whether the dispersive wave should be regenerated at the same vertical position for accelerometer $A_1$ 240. If the wave should be regenerated, steps 2514 and 2516 can be repeated.

If the signals and data are sufficient to provide a conclusive depth calculation, the wave does not have to be regenerated, it is determined at step 2518 whether additional data is needed. In particular, if additional data is needed, at optional step 2520 accelerometer $A_1$ 240 can be moved to another vertical position below the surface of the ground 106. The method then returns to step 2512, such that steps 2512 through 2518 can then be repeated for the new vertical position.

When it is determined at step 2518 that additional data is not needed, at step 2522, the time elapsed for the dispersive wave to travel from accelerometer $A_2$ 250 to accelerometer $A_1$ 240 can be correlated with each vertical position of accelerometer $A_1$ 240 when the elapsed times were determined. At step 2524, the data corresponding to each dispersive wave can be analyzed, as provided in greater detail in FIG. 27. At step 2526, the thickness of buried concrete 102 can be estimated based on data collected by the accelerometer $A_1$ at the one or more vertical positions an corresponding elapsed times for each wave. The method ends at step 2528.

FIG. 26 is a flow diagram illustrating an example method for applying filters and/or threshold values to the signals and/or data sets. The method of FIG. 26 will be described with reference to system 200 shown in FIG. 2, but is not so limited. In other examples, additional or alternative systems or components can be used to perform the method of FIG. 26. In practice, the method of FIG. 26 may be implemented with a combination of hardware and software, such as hardware and software in receiver 270 and/or external system 290.

Continuing from block 2516 of FIG. 25, step 2602 initiates one or more filter and/or check routines on the signals and/or data (e.g., received at the receiver 270 (or external system 290)). For example, the signals and/or data may be subjected to filtering (e.g., for one or more signal characteristics) and/or one or more criteria thresholds to determine whether the signals and/or data are of sufficient quality to provide a conclusive result. For example, all waves detected by the accelerometer(s) are subjected to one or more of a pre-trigger noise check function and/or a dead gauge check function.

As provided in step 2604, a pre-trigger signal check can be performed on all incoming signals. An example pre-trigger noise check function analyzes raw signal characteristics for fluctuations that exceed one or more thresholds (e.g., positive or negative) within a predetermined sampling period (e.g., within a given time, a threshold number (600) of pings, etc.).

In some examples, a dead gauge check can be performed on incoming signals in step 2606. For instance, the signals can be subjected to a dead-gauge check function check to determine whether the signal(s) have a sufficient amplitude (e.g., as compared to one or more threshold amplitudes) to provide a conclusive result.

In some examples, an overall analysis can be performed on incoming signals and/or data sets in step 2608. Accordingly, additional or alternative filtering can be performed to reduce or eliminate noise in the signal and/or reduce or eliminate values outside a predetermined range or threshold. For instance, one or more of the detected signals is filtered using a Short Kernel Method (SKM) filter, which removes frequencies greater than one or more threshold filter frequencies. The filter frequency, which is typically in the range of 500 to 1000 Hz, may be hard-coded in an algorithm implementing the pad thickness, or the range may be adjustable (e.g., determined by an algorithm based on one or more conditions, selected by an operator, etc.).

In step 2610, the system can determine whether the signals and/or data that have been subjected to analysis satisfy the applied criteria and/or thresholds. If not, the data is deemed inconclusive in step 2612, and the sampling event may be repeated (such as returning to step 2512 of FIG. 25). If the data does satisfy the applied criteria and/or thresholds, the method proceeds to step 2614, where the system determines whether a sufficient number of signals have been accepted. For example, a smaller number of signals may have satisfied the thresholds than is needed to conclusively calculate or estimate the depth measurement. If the number of signals is insufficient, the data is deemed inconclusive in step 2616, and the sampling event may be repeated (such as returning to step 2512 of FIG. 25). If the number of signals is sufficient, the data is deemed conclusive, and the method may proceed to step 2518 of FIG. 25 to determine whether additional data is needed.

As disclosed herein, if a signal (or data set) fails one of these functions, the signal may be ignored and/or the particular detection event (e.g., at the particular depth) may be repeated until the signal(s) and/or data satisfy all required conditions. If a large enough number of the signals and/or data sets fail these functions (e.g., beyond a threshold amount), the entire sampling event may need to be repeated.

FIG. 27 is a flow diagram illustrating an example method for analyzing data corresponding to each dispersive wave. The method of FIG. 27 will be described with reference to system 200 shown in FIG. 2, but is not so limited. In other examples, additional or alternative systems or components can be used to perform the method of FIG. 27. In practice, the method of FIG. 27 may be implemented with a combination of hardware and software, such as hardware and software in receiver 270 and/or external system 290.

Continuing from block 2524 of FIG. 25, step 2702 analyzes the signals to determine one or more peaks (e.g., a positive and/or negative peak) corresponding to each depth where a sampling event occurred. At step 2704, the method compares the peaks to one or more threshold values to determine whether the signal characteristics are sufficient to provide a conclusive result.

In some examples, after filtering and/or function checks, a number of wave-arrival points may be eliminated. As a result, a number of wave-arrival-time time stamps for those signals is missing. For instance, if a number of adjacent points exceed a threshold value, or if a proportion of a given group of adjacent signals' arrival-time points are missing, the results may be rendered inconclusive.

If not, the data is deemed inconclusive in step 2706, and the sampling event may be repeated (such as returning to step 2512 of FIG. 25). If the number and/or quality of the peaks are sufficient, the data is deemed conclusive, and the method may proceed to step 2708 to identify an inflection depth. If the magnitude of the greatest negative-change in slope of the group best-fit lines does not exceed a minimum threshold value, there is no clear inflection point, and the results may be rendered inconclusive.

In step 2710, one or more best-fit lines can be determined (e.g., by drawing a best fit line on a plotted graph, and/or calculating based on peak values). For example, a first best-fit line can be determined on a first side (e.g., corresponding to shallower depths than the inflection depth) of a point on the plotted graph corresponding to the inflection depth (e.g., the inflection point), and a second best-fit line can be determined on a second side (e.g., corresponding to deeper depths than the inflection depth) of the point corresponding to the inflection depth. The first and second best-fit lines are fit to wave-arrival points immediately above and immediately below the inflection point. If a number of points missing in these areas exceeds a threshold number, there are not enough points to accurately calculate the best-fit lines, and the results may be rendered inconclusive.

Once the best-fit lines are determined, the lines are compared with one or more threshold values in step 2712. For example, if plots of peaks do not result in a line sufficient to provide a conclusive result (e.g., insufficient number of peaks, variations between adjacent peaks exceed a threshold amount), the data is deemed inconclusive in step 2714, and the sampling event may be repeated (such as returning to step 2512 of FIG. 25).

If the plotted points fail to generate a qualifying best-fit line on one or both of the first and second best-fit lines, the results may be rendered inconclusive.

If the best-fit lines do satisfy the applied thresholds, the method proceeds to step 2716 to determine first and second slopes corresponding to the first and second best-fit lines, respectively. At step 2718, the first and second slopes are compared to a threshold amount. If the difference between the slopes does not exceed a threshold amount, the data is deemed inconclusive in step 2720, and the sampling event may be repeated (such as returning to step 2512 of FIG. 25).

Once plotted, the slopes of the first and second best-fit lines may be too close (e.g., their slopes do not differ greater than a threshold amount). As the depth-coordinate of the intersection point is sensitive to the location of each line, even slight adjustments of the slope of one or both lines would produce a large change in the predicted depth. Therefore, if the difference between the slopes does not exceed a threshold amount, the slopes are considered too close, and the results may be rendered inconclusive.

If the slope does exceed the threshold amount, the method proceeds to step 2722 to calculate or estimate an intersection point between the first and second best-fit lines. At step 2724, the depth of the buried concrete 102 (e.g., a bottom surface) is calculated or estimated based on the intersection point. The process then proceeds to step 2526 of FIG. 25 to estimate the thickness of buried concrete 102.

Any number of peaks (positive and/or negative) may be utilized in determining one or more slopes of one or more of the best-fit lines (or group lines). In some examples, best-fit lines may be replaced with an entirely different system and/or method of calculating or estimating buried concrete portion depth.

In some examples, the systems and/or methods are executed on a predetermined routine (e.g., algorithms and/or instructions stored on a memory device) and/or circuit pathways (e.g., hardware or firmware, printed circuit boards, etc.). In some examples, one or more routines are informed and/or implemented via machine-learning techniques to calculate or estimate the buried concrete portion depth. For instance, a machine-learning model may be trained using a library of datasets consisting of known buried concrete portion depths, numerous peaks (e.g., time stamps and/or amplitudes) corresponding to each signal, and/or the signals themselves. This model (or application) may utilize best-fit lines from the post-processing routine, time-stamps and/or amplitudes of peaks extracted from each signal or data set, or a combination of one or more features.

While particular embodiments have been shown and described, it will be apparent to those skilled in the art that various changes and modifications in form and details may be made therein without departing from the spirit and scope of this disclosure and are intended to form a part of the invention as defined by the following claims, which are to be interpreted in the broadest sense allowable by law. Further, the sequence of steps for the example methods described or illustrated herein are not to be construed as necessarily requiring their performance in the particular order described or illustrated unless specifically identified as requiring so or clearly identified through context. Moreover, the example methods may omit one or more steps described or illustrated, or may include additional steps in addition to those described or illustrated. Thus, one of ordinary skill in the art, using the disclosures provided herein, will appreciate that various steps of the example methods can be omitted, rearranged, combined, and/or adapted in various ways without departing from the spirit and scope of the inventions. Additionally, while the disclosed systems and methods have been explained in terms of measuring dispersive waves in concrete, it is contemplated that the systems and methods can be applied to other dispersive media.

What is claimed is:

1. A system to determine a thickness of a buried concrete structure, the system comprising:
   a hollow tube configured to be driven into a ground adjacent the buried concrete structure;
   a casing configured to house an accelerometer;
   a conduit configured to extend into the hollow tube and support the casing arranged at a first end of the hollow tube; and
   a collar comprising an opening shaped to accept the conduit in one or more distinct orientations, the collar arranged at an opening of the hollow tube at a second end opposite the first end to receive one or more conduits.

2. The system of claim 1 further comprising:
   an accelerometer housed within the casing and configured to generate data associated with a plurality of dispersive waves emanating from the buried concrete structure; and
   a receiver communicatively coupled to the accelerometer, wherein the receiver comprises:
      a display;
      at least one input module configured to receive data from the accelerometer;
      a processor; and
      memory coupled to the processor, wherein the memory stores instructions that, when executed by the processor, cause the processor to:
         receive data from the accelerometer associated with a plurality of dispersive waves; and
         process the received data to determine a thickness of the buried concrete structure.

3. The system of claim 2, wherein processing the received data to determine a thickness of the buried concrete structure comprises performing one or more quality checks on the received data.

4. The system of claim 3, wherein the one or more quality checks comprises a pre-trigger noise check on data as it is received from the accelerometer.

5. The system of claim 3, wherein the one or more quality checks comprises a dead gauge check.

6. The system of claim 3, wherein the one or more quality checks comprises a pre-trigger noise check on all of the received data.

7. The system of claim 2, wherein processing the received data to determine a thickness of the buried concrete structure comprises determining an inflection depth.

8. The system of claim 7, wherein processing the received data to determine a thickness of the buried concrete structure further comprises:
   determining a first best fit line for data above the inflection depth;
   determining a second best fit line for data below the inflection depth;
   determining an intersection of the first and second best fit lines; and
   determining a thickness of the buried concrete structure based on the intersection.

* * * * *